US012659197B2

(12) United States Patent
Patil et al.

(10) Patent No.: US 12,659,197 B2
(45) Date of Patent: Jun. 16, 2026

(54) ULTRASOUND BEAM QUALITY TEST APPARATUS AND METHODS

(71) Applicant: Aronix LLC, Peachtree Corners, GA (US)

(72) Inventors: Arun Narayan Patil, Winder, GA (US); Anand Raghunath Bhave, Pune (IN); Sunanda Narayan Patil, Pune (IN); Pratibha Narayan Patil, Pune (IN); Jesus Ovirne Lopez, Winder, GA (US)

(73) Assignee: Aronix LLC, Peachtree Corners, GA (US)

( * ) Notice: Subject to any disclaimer, the term of this patent is extended or adjusted under 35 U.S.C. 154(b) by 404 days.

(21) Appl. No.: 18/510,962

(22) Filed: Nov. 16, 2023

(65) Prior Publication Data

US 2024/0121137 A1 Apr. 11, 2024

Related U.S. Application Data

(63) Continuation-in-part of application No. 18/111,519, filed on Feb. 17, 2023, now Pat. No. 11,863,355, which is a continuation-in-part of application No. 18/074,222, filed on Dec. 2, 2022, now Pat. No. 11,771,398, and a continuation-in-part of application No. 17/962,812, filed on Oct. 10, 2022, now Pat. No. 11,892,326.

(51) Int. Cl.
*H04L 7/027* (2006.01)
*A61B 5/024* (2006.01)
*H03K 19/007* (2006.01)
*H04L 25/02* (2006.01)

(52) U.S. Cl.
CPC ...... *H04L 25/0272* (2013.01); *A61B 5/02411* (2013.01); *H03K 19/007* (2013.01); *A61B 5/02438* (2013.01)

(58) Field of Classification Search
CPC combination set(s) only.
See application file for complete search history.

(56) References Cited

U.S. PATENT DOCUMENTS 5,158,536 A * 10/1992 Sekins .............. A61M 16/0404
604/20
5,844,140 A * 12/1998 Seale ................. G01N 29/2456
73/620

(Continued)

*Primary Examiner* — Sanjay Cattungal
(74) *Attorney, Agent, or Firm* — H. Brock Kolls

(57) ABSTRACT

The present invention relates to an ultrasound beam quality test apparatus and methods of use. In this regard, fetal heart rate (FHR) transducer is placed for test and interconnected with fetal monitors. Phantoms of different heights can be placed on the FHR transducer. A computer system includes a beam control circuit. A plurality of hydrophone piezo-electric crystal (PZT) discs are placed on top of the phantom and interconnected with the beam control circuit. The computer system analyzes the ultrasound beam quality, of the FHR transducer, as it passes through the phantom. The beam control circuit can also control the oscillating motion of a metal plate to simulate a fetal heart beat by way of a linear actuator. The FHR transducer registered heartbeat, by way of the fetal monitor, is then compared to the simulated fetal heart beat to determine if the FHR transducer is working correctly.

24 Claims, 35 Drawing Sheets

(56) References Cited

U.S. PATENT DOCUMENTS

| | | | | |
|---|---|---|---|---|
| 7,819,806 | B2 * | 10/2010 | Yang | A61B 8/467 |
| | | | | 600/443 |
| 8,150,128 | B2 * | 4/2012 | Konofagou | A61B 8/485 |
| | | | | 600/437 |
| 9,066,679 | B2 * | 6/2015 | Beach | A61B 8/08 |
| 10,441,820 | B2 * | 10/2019 | Konofagou | A61N 7/00 |
| 10,517,564 | B2 * | 12/2019 | Konofagou | A61B 8/02 |
| 10,524,762 | B2 * | 1/2020 | Kent | G16H 40/63 |
| 11,559,287 | B2 * | 1/2023 | McLaughlin | A61B 8/14 |
| 11,771,398 | B1 * | 10/2023 | Patil | B06B 1/0215 |
| | | | | 600/459 |
| 2015/0150452 | A1 * | 6/2015 | Oraevsky | A61B 5/14546 |
| | | | | 600/440 |

* cited by examiner

*Fig. 1*
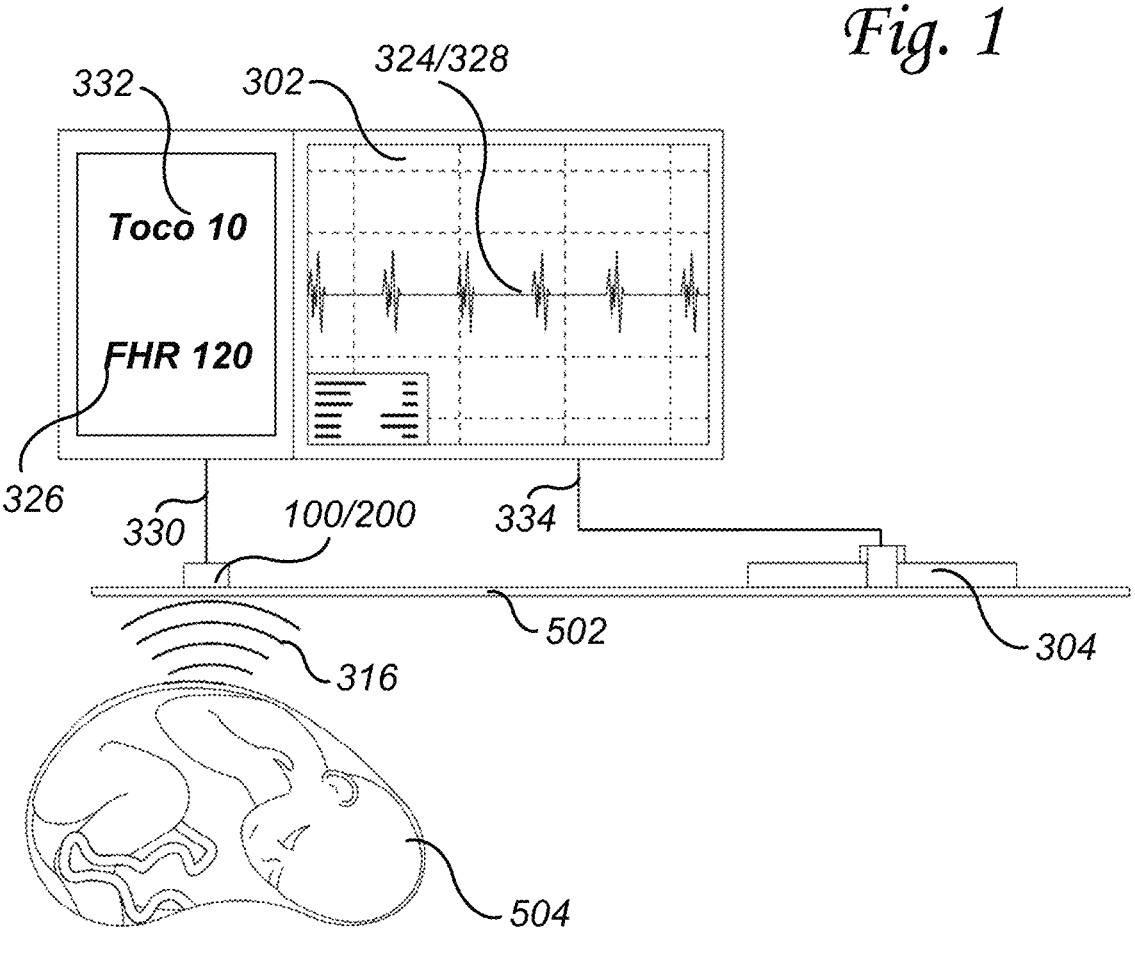
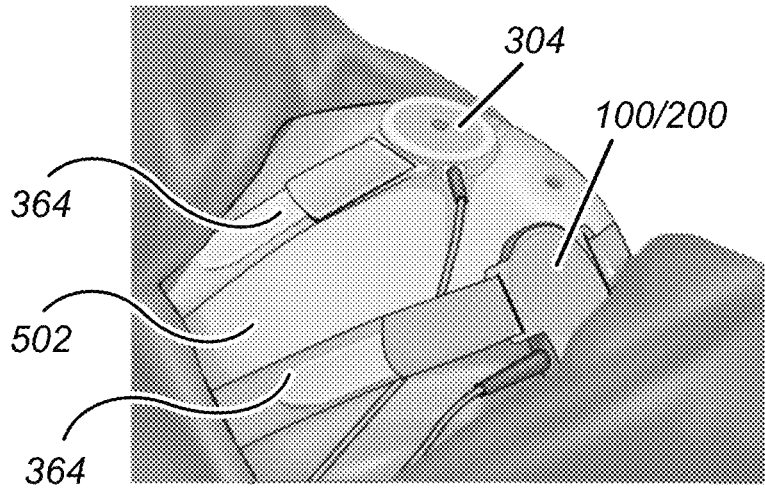

*Fig. 5*
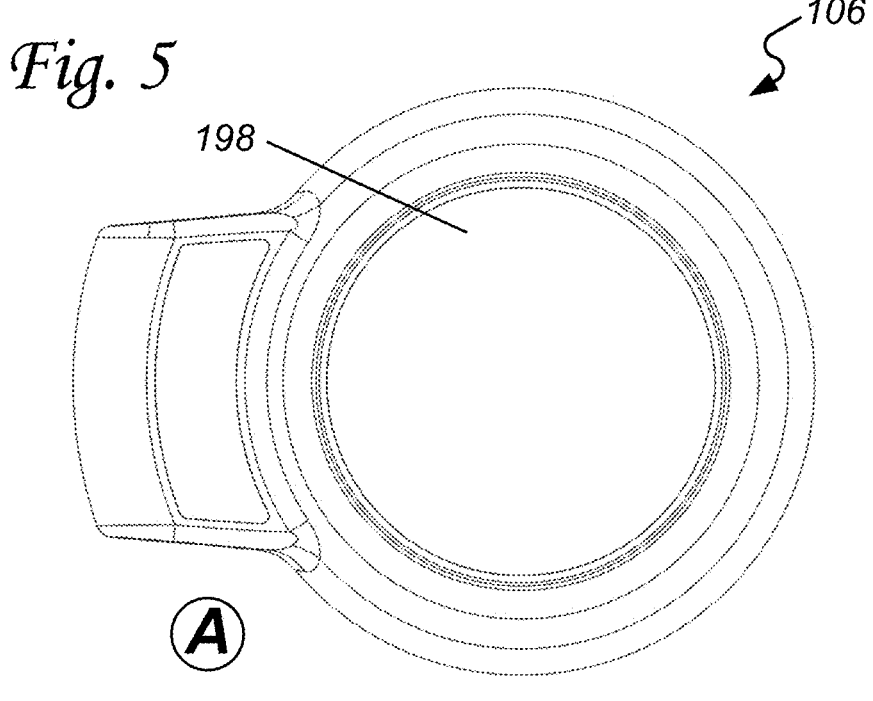
Ⓐ
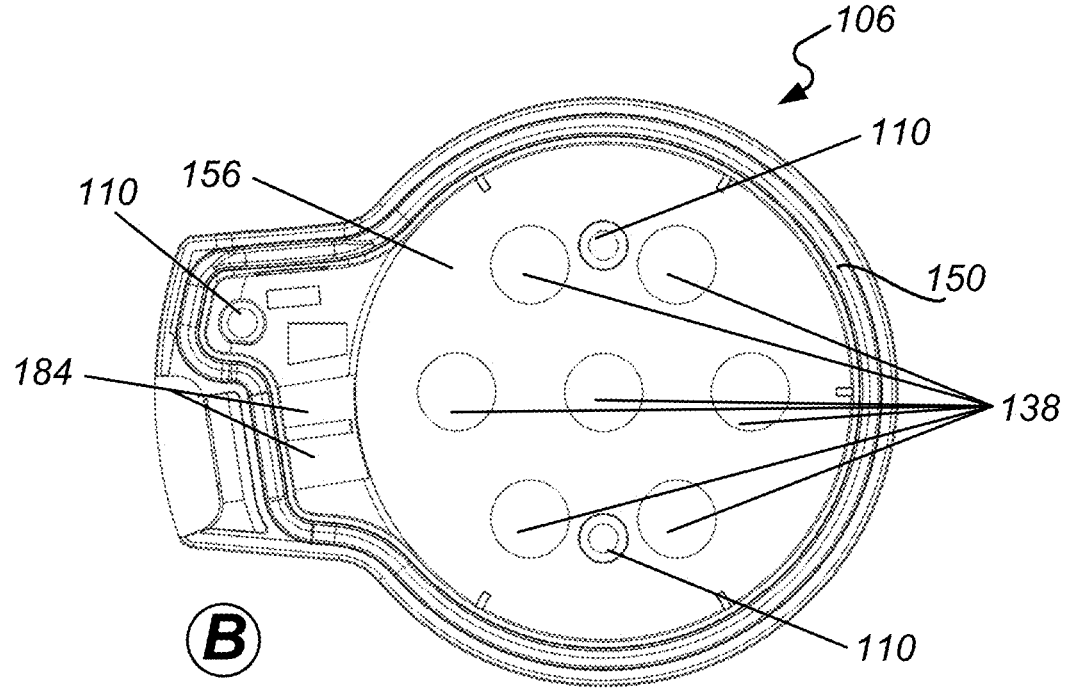
Ⓑ

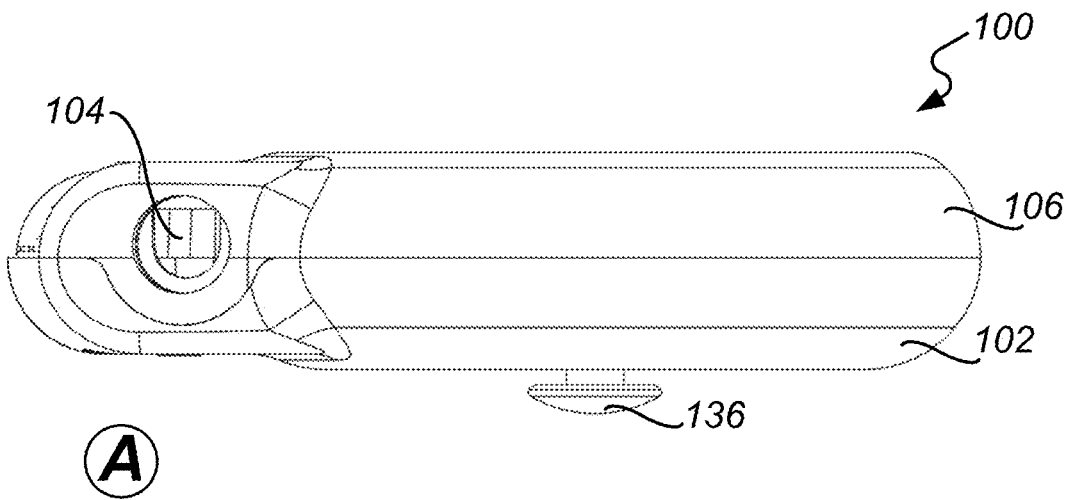
Ⓐ
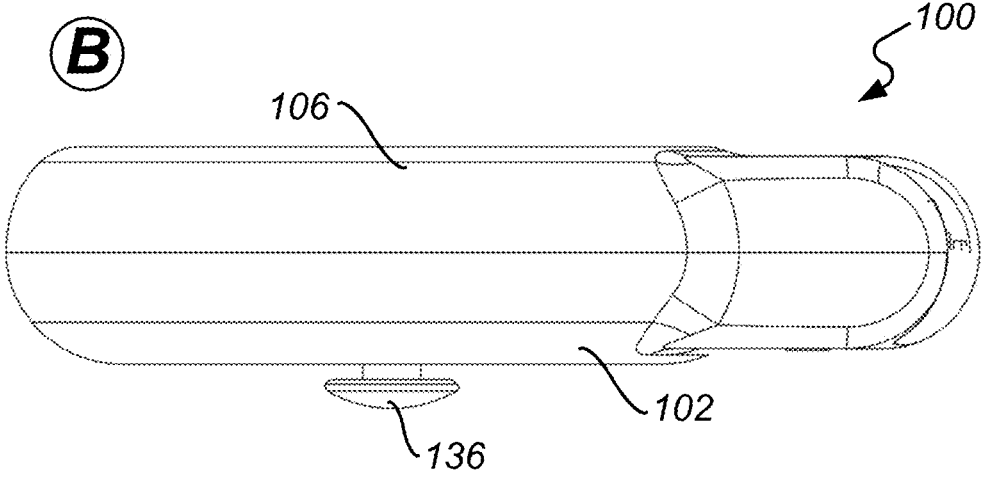
Ⓑ
*Fig. 7*

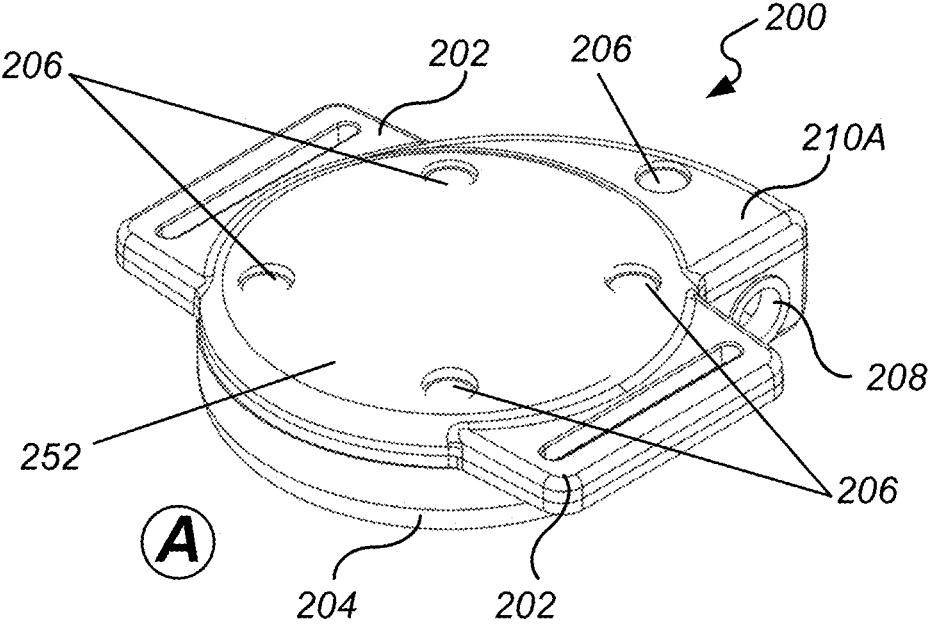
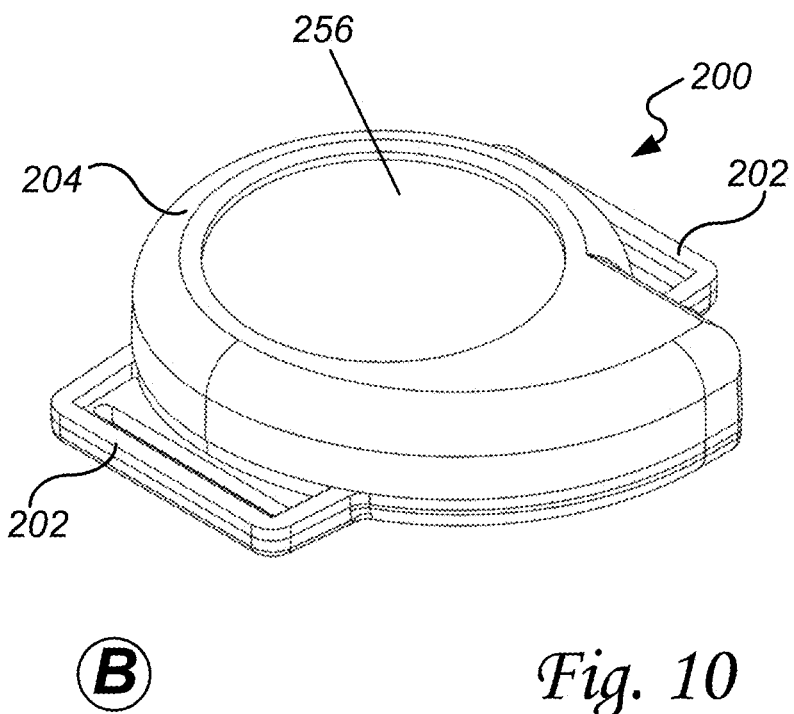
*Fig. 10*

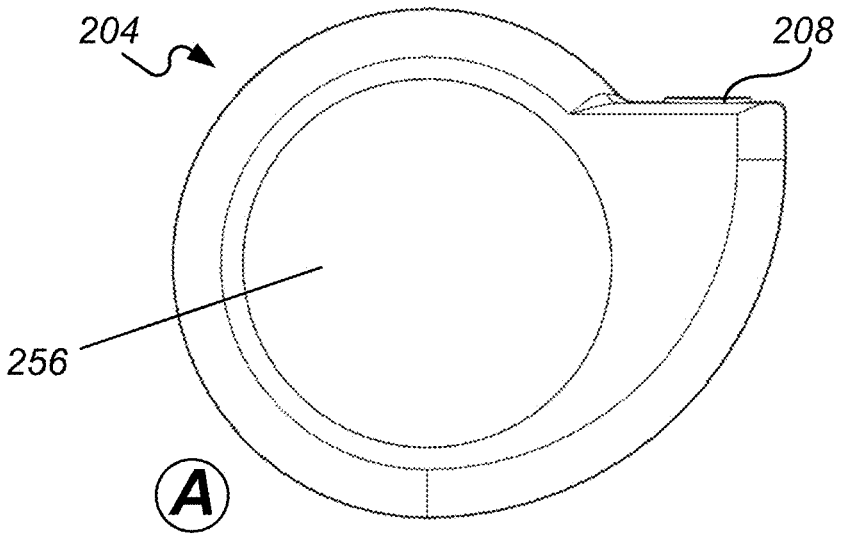
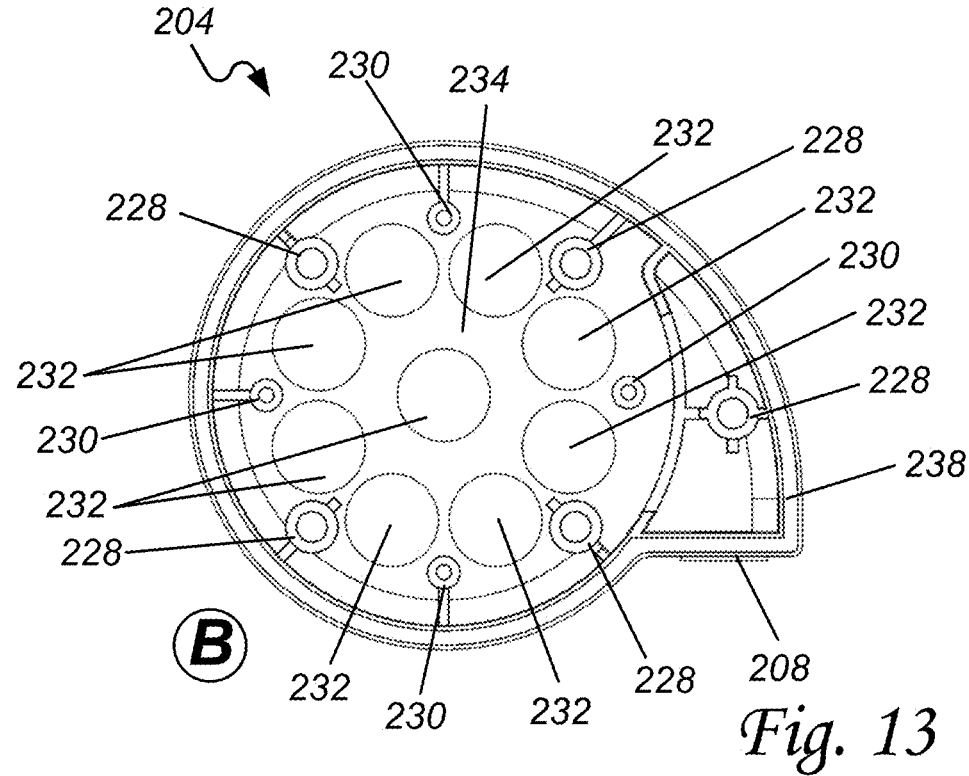
*Fig. 13*

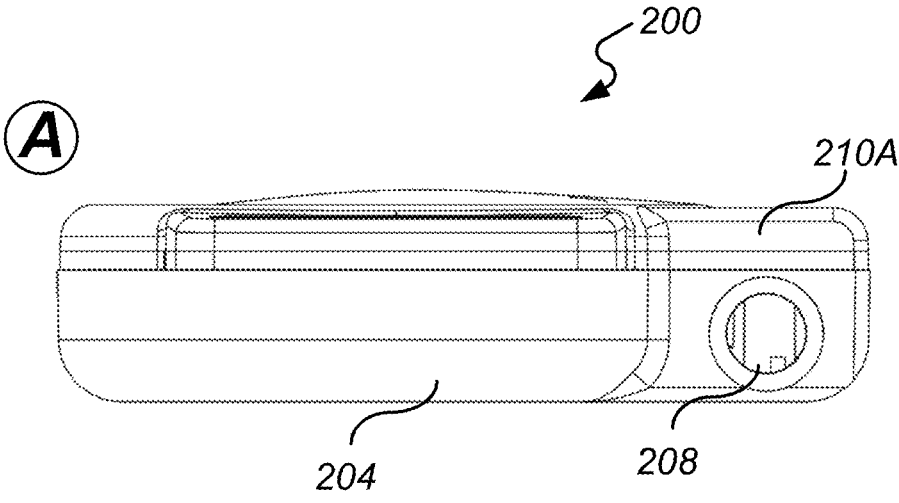
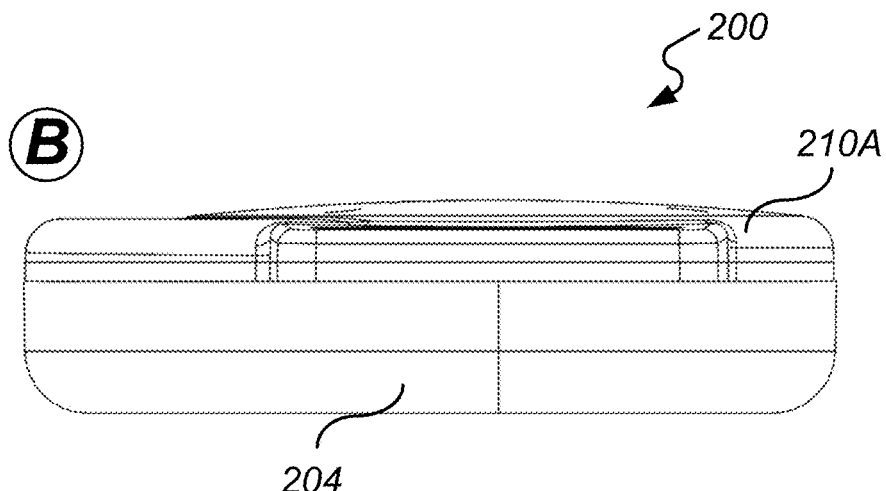
*Fig. 14*

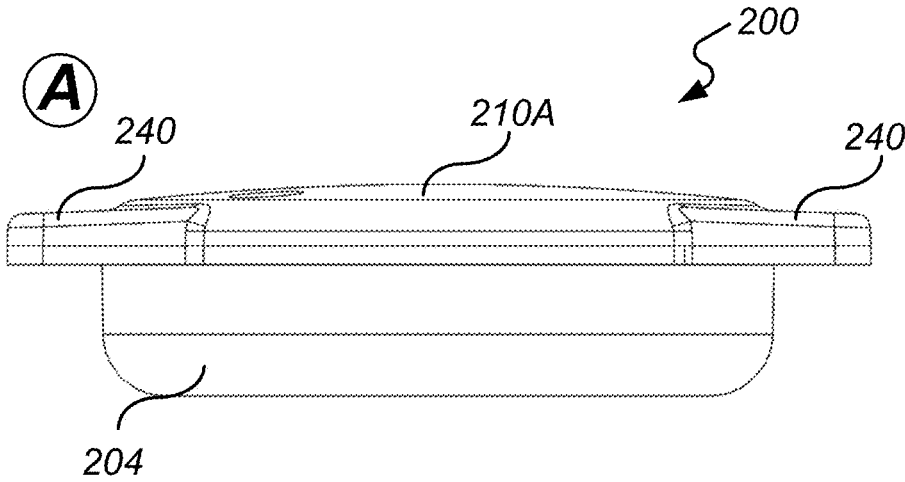
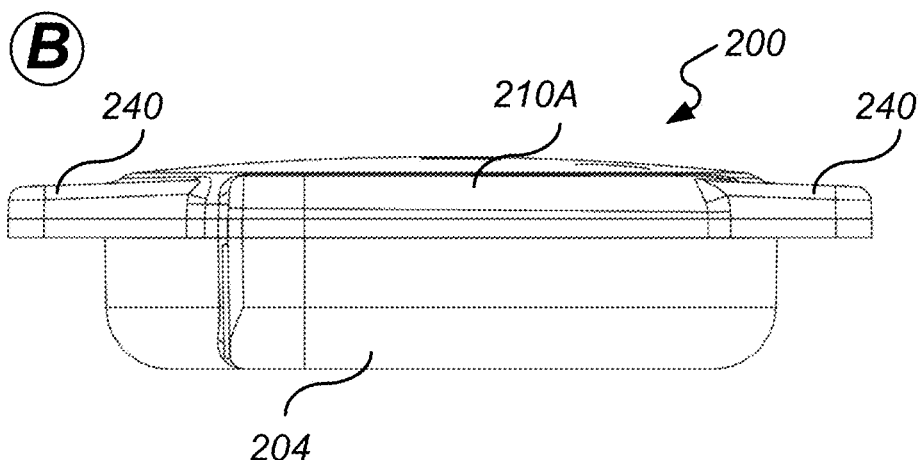
*Fig. 15*

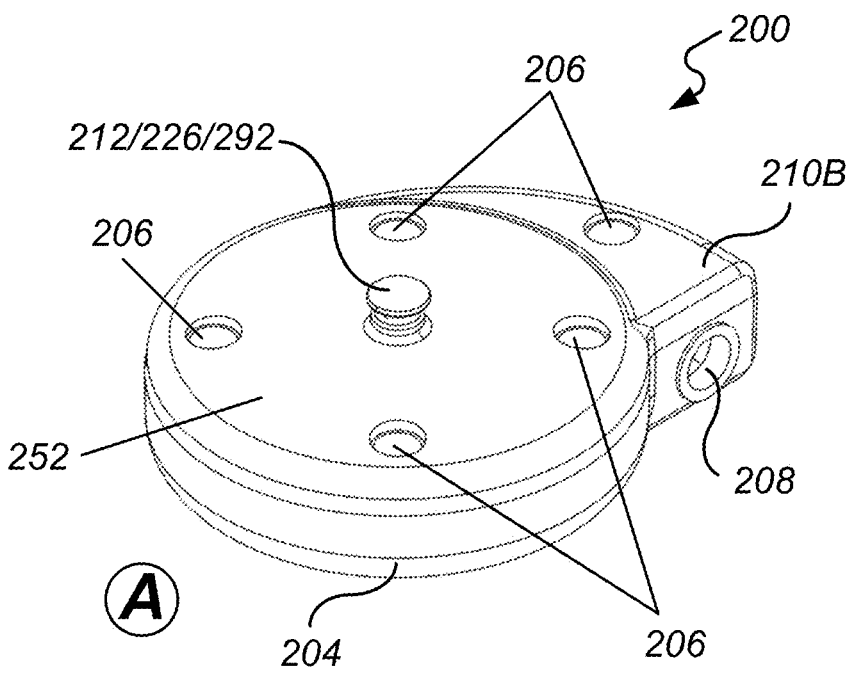
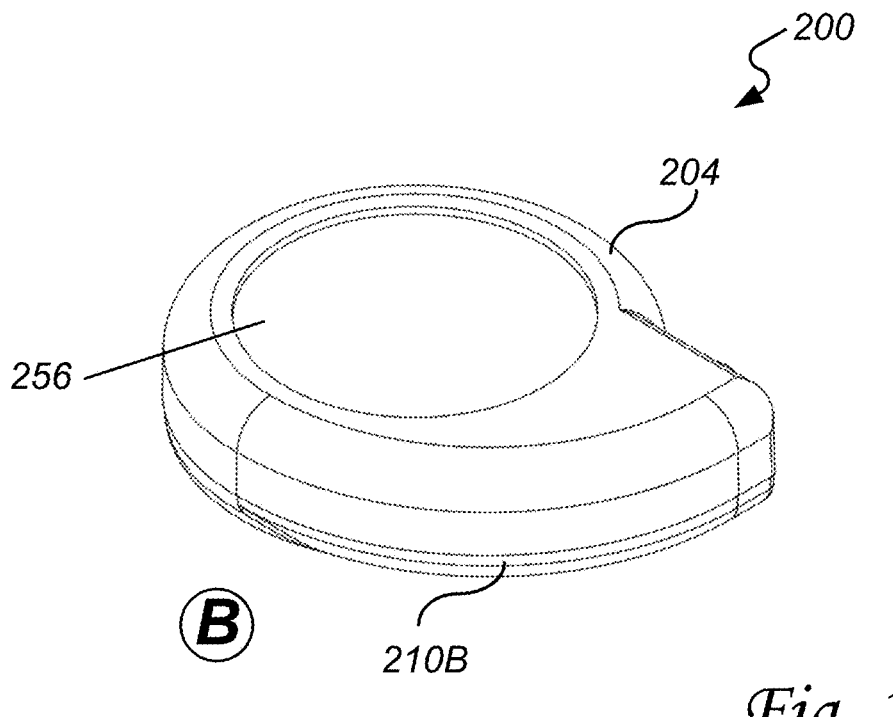
*Fig. 17*

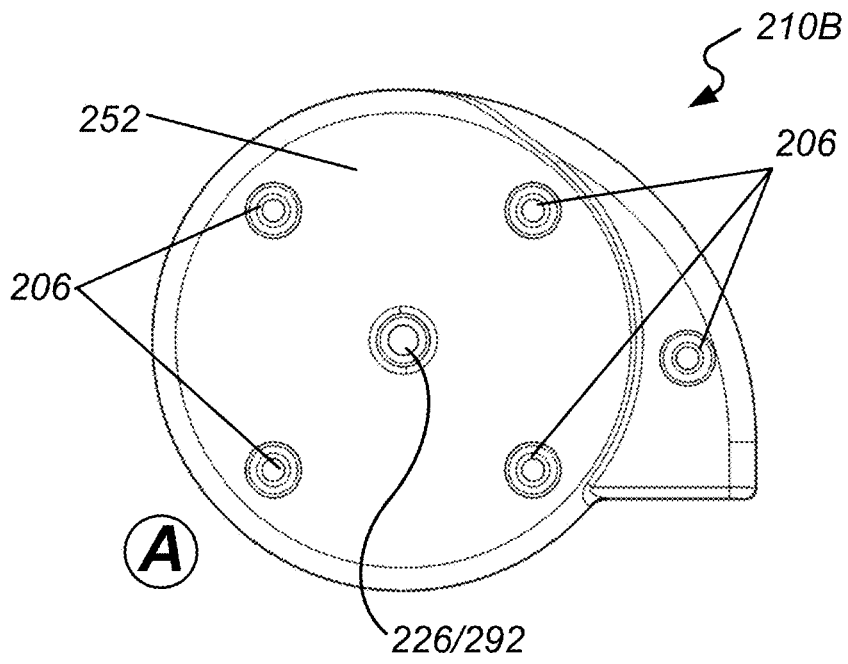
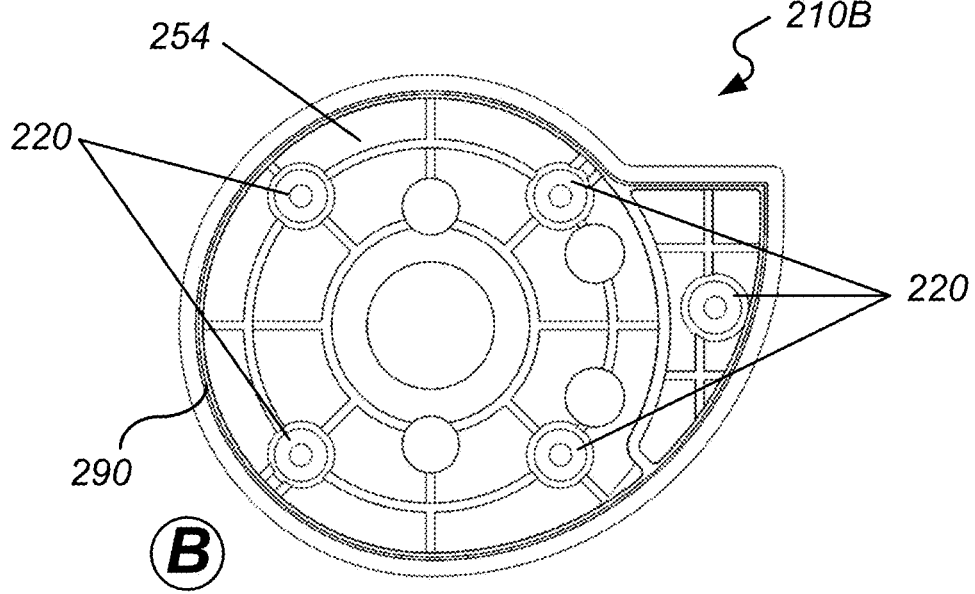
*Fig. 18*

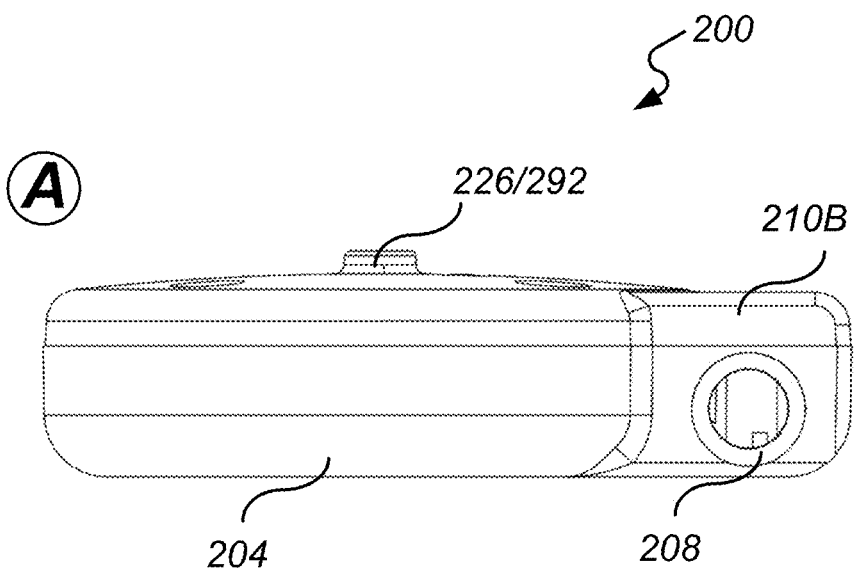
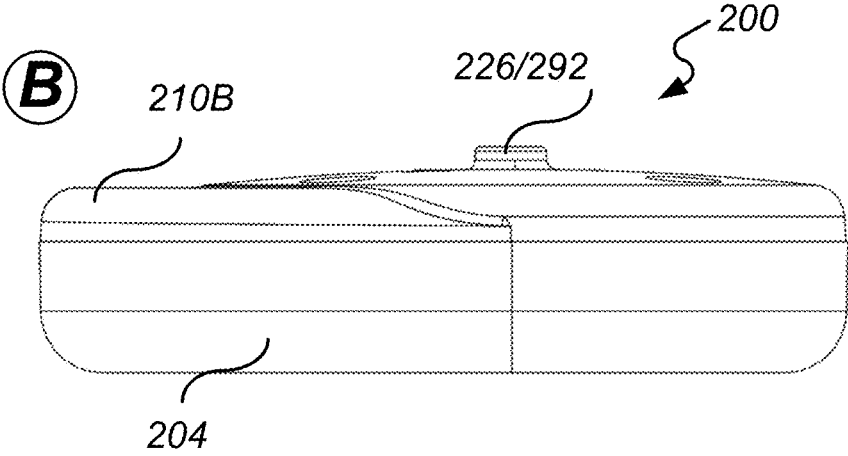
*Fig. 19*

200
226/292
Ⓐ
210B
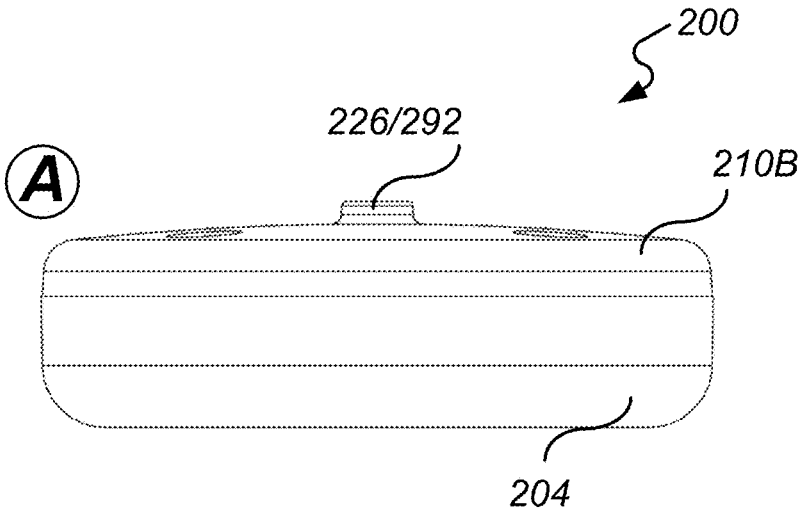
204
200
226/292
Ⓑ
210B
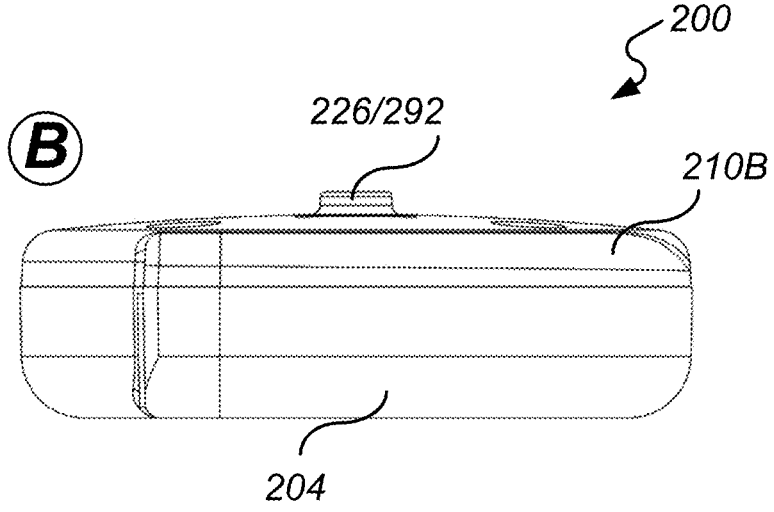
204
*Fig. 20*

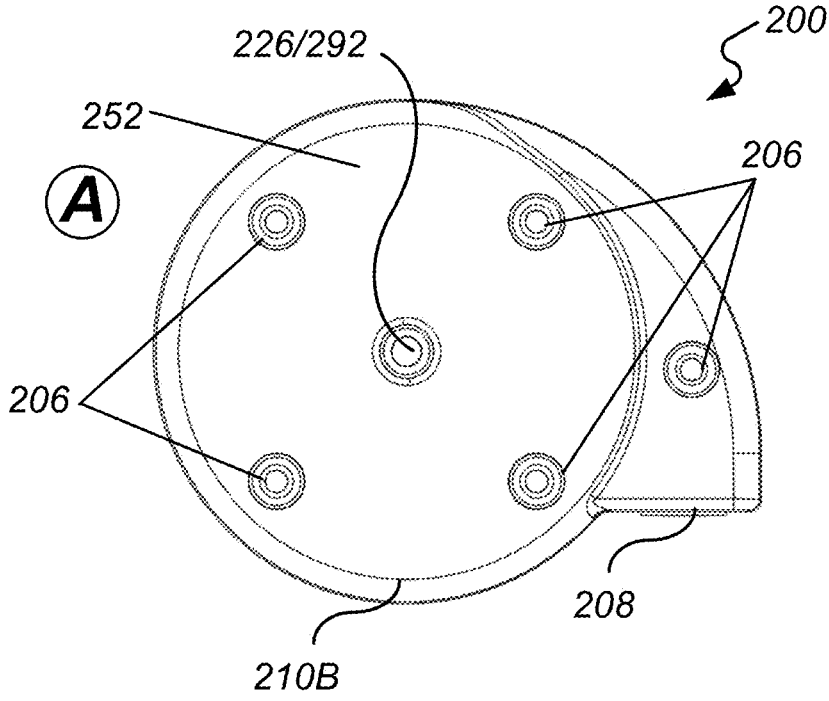
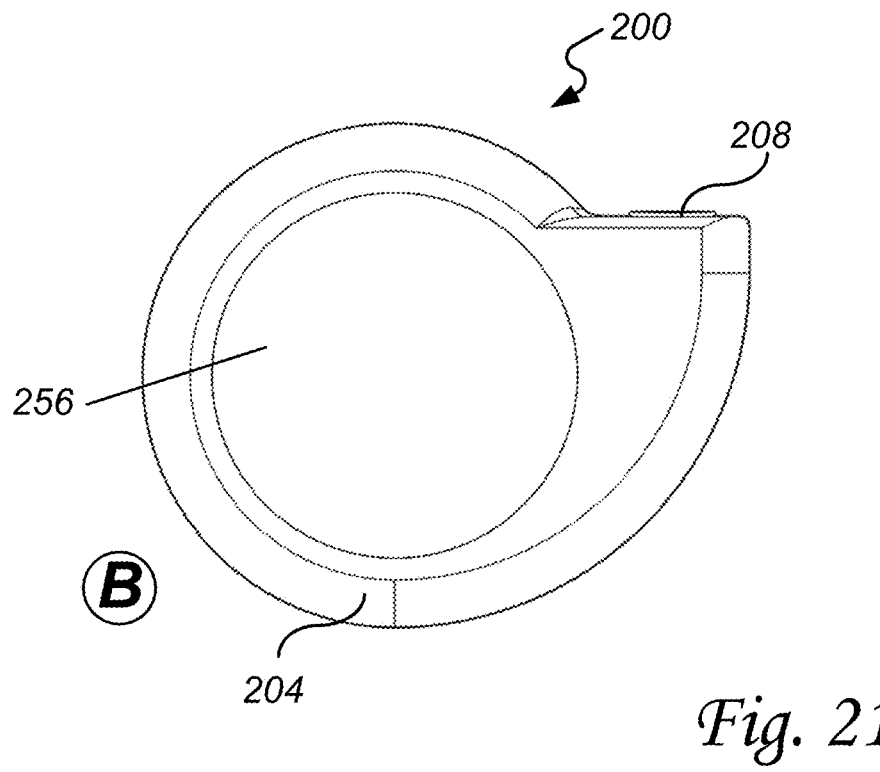
*Fig. 21*

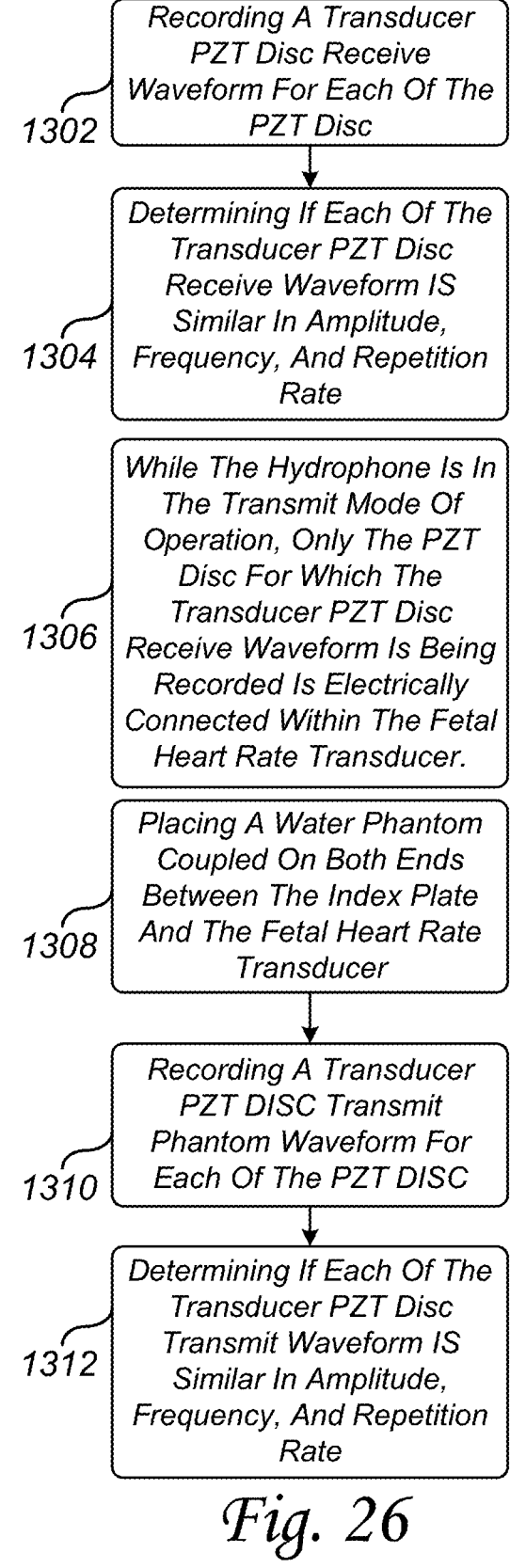

```
        ( Start )
            │
            ▼
┌──────────────────────────┐
│  Coupling An Index Plate  │
│  With An Ultrasound       │
│  Coupling Jelly To A Fetal│
│  Heart Rate Transducer    │
└──────────────────────────┘
    1202        │  1204
                ▼
┌──────────────────────────┐
│  Recording A Transducer   │
│  PZT Disc Waveform For    │
│  Each PZT Disc            │
└──────────────────────────┘
                │
                ▼
┌──────────────────────────┐
│  Determining If Each Of The│
│  Transducer PZT Disc      │
│  Transmit Waveform Is     │
│  Similar In Amplitude,    │
│  Frequency, And Repetition│
│  Rate                     │
└──────────────────────────┘
    1206        │
                ▼
            ( Exit )
```

*Fig. 25*

```
┌──────────────────────────┐
│  Recording A Transducer   │
│  PZT Disc Receive         │
│  Waveform For Each Of The │
│  PZT Disc                 │
└──────────────────────────┘
1302            │
                ▼
┌──────────────────────────┐
│  Determining If Each Of The│
│  Transducer PZT Disc      │
│  Receive Waveform IS      │
│  Similar In Amplitude,    │
│  Frequency, And Repetition│
│  Rate                     │
└──────────────────────────┘
1304            │
                ▼
┌──────────────────────────┐
│  While The Hydrophone Is In│
│  The Transmit Mode Of     │
│  Operation, Only The PZT  │
│  Disc For Which The       │
│  Transducer PZT Disc      │
│  Receive Waveform Is Being│
│  Recorded Is Electrically │
│  Connected Within The Fetal│
│  Heart Rate Transducer.   │
└──────────────────────────┘
1306            │
                ▼
┌──────────────────────────┐
│  Placing A Water Phantom  │
│  Coupled On Both Ends     │
│  Between The Index Plate  │
│  And The Fetal Heart Rate │
│  Transducer               │
└──────────────────────────┘
1308            │
                ▼
┌──────────────────────────┐
│  Recording A Transducer   │
│  PZT DISC Transmit        │
│  Phantom Waveform For     │
│  Each Of The PZT DISC     │
└──────────────────────────┘
1310            │
                ▼
┌──────────────────────────┐
│  Determining If Each Of The│
│  Transducer PZT Disc      │
│  Transmit Waveform IS     │
│  Similar In Amplitude,    │
│  Frequency, And Repetition│
│  Rate                     │
└──────────────────────────┘
1312
```

| Source | Observer | Emitted | | Propagating | | Observed | |
|---|---|---|---|---|---|---|---|
| | | freq. | wave length | freq. | wave length | freq. | wave length |
| • | • | $n$ | $\lambda$ | $n$ | $\lambda$ | $n$ | $\lambda$ |
| $V_s\ \rightarrow$ | • | $n$ | $\lambda$ | $\dfrac{nv}{v-v_s}$ | $\left(\dfrac{v-v_s}{v}\right)\lambda$ | $\dfrac{nv}{v-v_s}$ | $\left(\dfrac{v-v_s}{v}\right)\lambda$ |
| $\leftarrow\ V_s$ | • | $n$ | $\lambda$ | $\dfrac{nv}{v+v_s}$ | $\left(\dfrac{v+v_s}{v}\right)\lambda$ | $\dfrac{nv}{v+v_s}$ | $\left(\dfrac{v+v_s}{v}\right)\lambda$ |
| • | $\leftarrow\ V_o$ | $n$ | $\lambda$ | $n$ | $\lambda$ | $\left(\dfrac{v+v_o}{v}\right)n$ | $\left(\dfrac{v}{v+v_o}\right)\lambda$ |
| • | $V_o\ \rightarrow$ | $n$ | $\lambda$ | $n$ | $\lambda$ | $\left(\dfrac{v-v_o}{v}\right)n$ | $\left(\dfrac{v}{v-v_o}\right)\lambda$ |
| $V_s\ \rightarrow$ | $\leftarrow\ V_o$ | $n$ | $\lambda$ | $\dfrac{nv}{v-v_s}$ | $\dfrac{v-v_s}{v}\lambda$ | $\left(\dfrac{v+v_o}{v-v_s}\right)n$ | $\left(\dfrac{v-v_s}{v+v_o}\right)\lambda$ |
| $V_s\ \rightarrow$ | $V_o\ \rightarrow$ | $n$ | $\lambda$ | $\dfrac{nv}{v-v_s}$ | $\dfrac{v-v_s}{v}\lambda$ | $\left(\dfrac{v-v_o}{v-v_s}\right)n$ | $\left(\dfrac{v-v_s}{v-v_o}\right)\lambda$ |
| $\leftarrow\ V_s$ | $\leftarrow\ V_o$ | $n$ | $\lambda$ | $\dfrac{nv}{v+v_s}$ | $\left(\dfrac{v+v_s}{v}\right)\lambda$ | $\left(\dfrac{v+v_o}{v+v_s}\right)n$ | $\left(\dfrac{v+v_s}{v+v_o}\right)\lambda$ |
| $\leftarrow\ V_s$ | $V_o\ \rightarrow$ | $n$ | $\lambda$ | $\dfrac{v}{v+v_s}n$ | $\dfrac{v+v_s}{v}\lambda$ | $\left(\dfrac{v-v_o}{v+v_s}\right)n$ | $\left(\dfrac{v+v_s}{v-v_o}\right)\lambda$ |

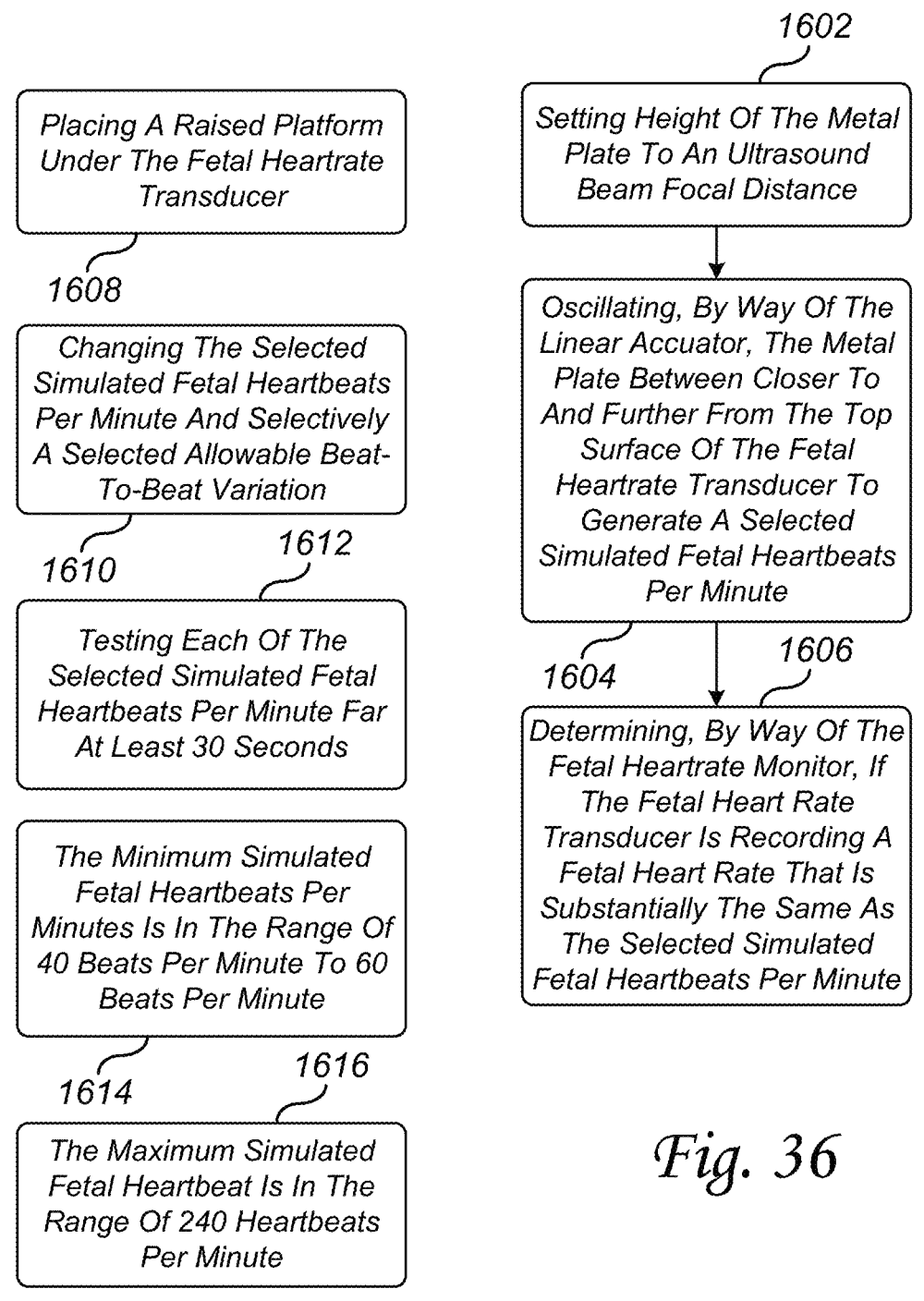

Placing A Raised Platform Under The Fetal Heartrate Transducer

*1608*

Changing The Selected Simulated Fetal Heartbeats Per Minute And Selectively A Selected Allowable Beat-To-Beat Variation

*1610*     *1612*

Testing Each Of The Selected Simulated Fetal Heartbeats Per Minute Far At Least 30 Seconds The Minimum Simulated Fetal Heartbeats Per Minutes Is In The Range Of 40 Beats Per Minute To 60 Beats Per Minute

*1614*     *1616*

The Maximum Simulated Fetal Heartbeat Is In The Range Of 240 Heartbeats Per Minute Setting Height Of The Metal Plate To An Ultrasound Beam Focal Distance Oscillating, By Way Of The Linear Accuator, The Metal Plate Between Closer To And Further From The Top Surface Of The Fetal Heartrate Transducer To Generate A Selected Simulated Fetal Heartbeats Per Minute

*1604*     *1606*

Determining, By Way Of The Fetal Heartrate Monitor, If The Fetal Heart Rate Transducer Is Recording A Fetal Heart Rate That Is Substantially The Same As The Selected Simulated Fetal Heartbeats Per Minute

*Fig. 36*

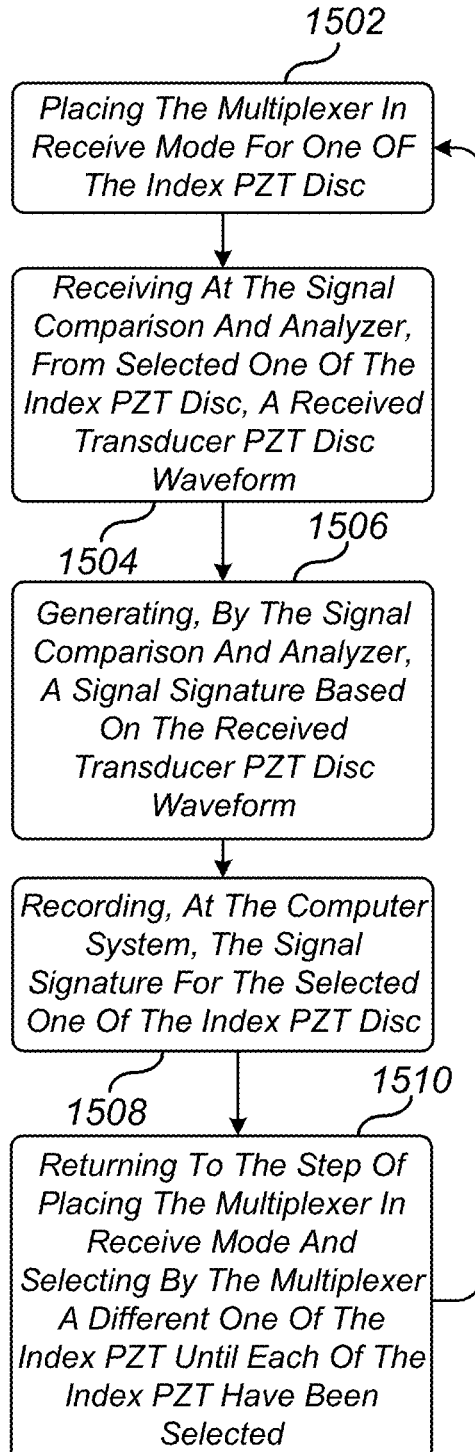

*1502*

Placing The Multiplexer In Receive Mode For One OF The Index PZT Disc

Receiving At The Signal Comparison And Analyzer, From Selected One Of The Index PZT Disc, A Received Transducer PZT Disc Waveform

*1504*

*1506*

Generating, By The Signal Comparison And Analyzer, A Signal Signature Based On The Received Transducer PZT Disc Waveform Recording, At The Computer System, The Signal Signature For The Selected One Of The Index PZT Disc

*1508*

*1510*

Returning To The Step Of Placing The Multiplexer In Receive Mode And Selecting By The Multiplexer A Different One Of The Index PZT Until Each Of The Index PZT Have Been Selected

*1512*

Changing, By Way Of The User, To A Different Height One Of The Phantom

Positioning For Test A Fetal Heartrate Transducer On The Ultrasound Beam Quality Test Apparatus

ULTRASOUND BEAM QUALITY TEST APPARATUS AND METHODS

CROSS-REFERENCE TO RELATED APPLICATIONS

This application contains subject matter which is related to the subject matter of the following co-pending applications. The below-listed applications are hereby incorporated herein by reference in their entirety:

This is a U.S. non-provisional application that is a continuation in part of a U.S. non-provisional application Ser. No. 18/111,519, inventor Arun Narayan Patil et al., entitled "FAIL-SAFE CIRCUIT FOR A LOW VOLTAGE DIFFERENTIAL SIGNALING RECEIVER", filed Feb. 17, 2023; which is a continuation in part of a U.S. non-provisional application Ser. No. 18/074,222, filed Dec. 2, 2022, inventor Arun Narayan Patil et al., entitled "FETAL HEART RATE TRANSDUCER", now U.S. Pat. No. 11,771,398, issued Oct. 3, 2023; and This is a U.S. non-provisional application that is a continuation in part of a U.S. non-provisional application Ser. No. 17/962,812, inventor Arun Narayan Patil et al., entitled "TOCODYNAMOMETER TRANSDUCER", filed Oct. 10, 2022.

TECHNICAL FIELD OF THE INVENTION

This invention relates to testing a fetal heart rate transducer and particularly to determining the ultrasound beam quality and the fetal heartbeat detection accuracy of the fetal heart rate detection.

BACKGROUND OF THE INVENTION

Before our invention in gynecology and obstetrics, one of the medical parameters important in assessing the condition of a fetus was the fetal heart rate measured by way of an ultrasound Doppler signal. Such fetal heart rate systems typically comprise a fetal heart rate transducer that is operationally coupled to a fetal heart rate monitor (fetal monitor/Cardiotocograph or CTG Machine). The fetal heart rate transducer is placed on the patient's stomach proximate to the fetus.

A shortcoming of prior fetal heart rate transducers is the bonding characteristics of the piezo-electric crystals (PZT) discs with the plastic resin used in creating the external transducer housing. In this regard, the PZT discs have a high acoustic impedance and hence their bonding to the plastic resin enclosure requires a very thin homogeneous layer of conformal adhesive that remains intact without change in acoustic properties over variation of temperatures (room temp, body temp, after contact to abdomen skin, etc.) and application of hygroscopic gel for coupling the ultrasonic wavefront (beam) to human tissue. Such characteristics are not present in current PZT crystal bonding techniques and as a result, a common failure of the fetal heart rate transducer is PZT discs separating from the plastic resin surface partially or entirely which creates signal degradation and spurious FUR readings rendering the transducer inoperable.

Another shortcoming of prior fetal heart rate transducers is the cracking and degradation of the standoffs that are molded into the plastic resin case. In this regard, either self-tapping screws are threaded into plastic standoffs or metal inserts are pressed into the standoffs. In both cases, the stress introduced in the plastic standoffs over time leads to the cracking of the plastic standoffs and the loosening of the self-tapping screws, the printed circuit board (PCB) secured by the screws and other components. Such loosening of the PCB and other components allows motion of these items as the patient breathes or moves, which is detected by the PZT discs causing inaccurate fetal heart rate readings.

Another shortcoming is that prior to our invention there wasn't a way to quantitatively test the integrity of the adhesive bond between the PZT discs and the plastic resin enclosure. Additionally, there wasn't a way to quantitively measure the ultrasound field strength and operational characteristics of PZT discs individually and/or in operational combination with the plurality of PZT discs within a fetal heart rate transducer.

Another shortcoming of prior fetal heart rate transducers is in the signal processing capabilities. In this regard, loose, broken, open, or shorted wire connections between the fetal heart rate transducer and the fetal monitor can be misreported and therefore cause inaccurate or intermittent fetal heart rate readings.

The present invention addresses these and other shortcomings by providing an improved fetal heart rate transducer. For these reasons and shortcomings as well as other reasons and shortcomings there is a long-felt need that gives rise to the present invention

SUMMARY OF THE INVENTION

The shortcomings of the prior art are overcome and additional advantages are provided through the provision of a method of using an ultrasound beam quality test apparatus for testing fetal heart rate transducers. The method comprises the step of positioning, for testing, a fetal heart rate transducer on the ultrasound beam quality test apparatus.

A computer system comprises a microprocessor, a memory, a beam control circuit, and a linear actuator controller. The microprocessor is operationally related to the memory, the beam control circuit, and the linear actuator controller. The beam control circuit comprises at least one multiplexer, and a signal comparison and analyzer. A fetal heart rate transducer comprises more than one transducer piezo-electric crystal (PZT) disc. The fetal heart rate transducer is electrically interconnected with a fetal monitor which causes each of the transducer PZT disc to generate a transducer PZT disc waveform. An index plate comprises more than one hydrophone PZT disc.

The phantom is placed between the fetal heart rate transducer and the index plate. Each of the hydrophone PZT discs is adhered to the index plate in positions that align with and correspond to the locations of each of the transducer PZT discs within the fetal heart rate transducer. Each of the hydrophone PZT discs is electrically interconnected with the beam control circuit. A linear actuator comprises a metal plate, the metal plate is attached to the linear actuator and is vertically adjustable by way of the linear actuator. The metal plate extends across the top surface of the fetal heart rate transducer. The linear actuator controller operates the linear actuator.

The method continues by placing the multiplexer in receive mode for one of the hydrophone PZT discs, and electrically disconnecting the other of the hydrophone PZT discs. And, receiving at the signal comparison and analyzer, from the selected one of the hydrophone PZT discs, a received transducer PZT disc waveform. The received transducer PZT disc waveform is the transducer PZT disc waveform from the transducer PZT disc that is positioned directly opposite selected one of the hydrophone PZT discs after passing through the phantom.

The method continues by generating, by way of the signal comparison and analyzer, a signal signature based on the received transducer PZT disc waveform, and recording, at the computer system, the signal signature for selected one of the hydrophone PZT discs. In operation, the selected one of the hydrophone PZT discs corresponds to one of the transducer PZT discs.

The method continues by returning to the step of placing the multiplexer in receive mode, and selecting a different one of the hydrophone PZT discs until the signal signature has been recorded for each of the hydrophone PZT discs. And, generating, by way of the computer system, an ultrasound beam quality report, wherein the ultrasound beam quality report compares one or more of a predetermined reference signal signature with the signal signature recorded for each one of the hydrophone PZT discs to determine the ultrasound beam quality of the fetal heart rate transducer, wherein each one of the hydrophone PZT discs corresponds to one of the transducer PZT disc.

The method continues by setting the height of the metal plate to an ultrasound beam focal distance, by way of the linear actuator. In operation, in this configuration, the phantom and the index plate are repositioned away from the top surface of the fetal heart rate transducer so that the top surface of the fetal heart rate transducer and the metal plate are opposed with only an air gap therebetween.

The method continues by oscillating, by way of the linear actuator, the metal plate between closer to and further from the top surface of the fetal heart rate transducer to generate a selected simulated fetal heartbeats per minute. In operation, the transducer PZT disc waveform is reflected off of the metal plate and received at the transducer PZT disc.

The method continues by, determining, by way of the fetal monitor, if the fetal heart rate transducer is recording a fetal heart rate that is substantially the same as the selected simulated fetal heartbeats per minute indicating the fetal heart rate transducer is operating correctly.

Additional shortcomings of the prior art are overcome and additional advantages are provided through the provision of an ultrasound beam quality test apparatus to test a fetal heart rate transducer. The ultrasound beam test apparatus comprises a phantom, a fetal monitor, and a computer system. The computer system comprises a microprocessor, a memory, and a beam control circuit, the microprocessor is operationally related to the memory, and the beam control circuit. The beam control circuit comprises at least one multiplexer, and a signal comparison and analyzer The ultrasound beam quality test apparatus further comprises a fetal heart rate transducer. The fetal heart rate transducer comprises more than one transducer piezo-electric crystal (PZT) disc. The fetal heart rate transducer is electrically interconnected with the fetal monitor which causes each of the transducer PZT disc to generate a transducer PZT disc waveform.

The ultrasound beam quality test apparatus further comprises an index plate. The index plate comprises more than one hydrophone PZT disc. The phantom is placed between the fetal heart rate transducer and the index plate. Each of the hydrophone PZT discs is adhered to the index plate in positions that align with and correspond to the locations of each of the transducer PZT discs within the fetal heart rate transducer. Each of the hydrophone PZT discs is electrically interconnected with the beam control circuit.

The memory is encoded with instructions that when executed by the microprocessor perform the steps of placing the multiplexer in receive mode for one of the hydrophone PZT discs and electrically disconnecting the other of the hydrophone PZT disc, and receiving at the signal comparison and analyzer, from the selected one of the hydrophone PZT discs, a received transducer PZT disc waveform. The received transducer PZT disc waveform is the transducer PZT disc waveform from the transducer PZT disc that is positioned directly opposite one of the selected hydrophone PZT discs after passing through the phantom.

By way of the signal comparison and analyzer, a signal signature is generated based on the received transducer PZT disc waveform. The signal signature is recorded, at the computer system, for the selected one of the hydrophone PZT discs. In operation, the selected one of the hydrophone PZT discs corresponds to one of the transducer PZT discs.

Processing then returns to the step of placing the multiplexer in receive mode and selects a different one of the hydrophone PZT discs until the signal signature has been recorded for each of the hydrophone PZT discs. By way of the computer system, a signal signature report is generated. In operation, the signal signature report details at least an ultrasound beam quality for each one of the transducer PZT discs based on at least the signal signature recorded by each corresponding one of the hydrophone PZT discs.

Additional shortcomings of the prior art are overcome and additional advantages are provided through the provision of an ultrasound beam quality test apparatus for testing fetal heart rate transducers. The ultrasound beam test apparatus comprises a fetal monitor and a computer system. The computer system comprises a microprocessor and a memory. The microprocessor is operationally related to the memory.

The ultrasound beam quality test apparatus further comprises a fetal heart rate transducer. The fetal heart rate transducer comprises more than one transducer piezo-electric crystal (PZT) disc. The fetal heart rate transducer is electrically interconnected with the fetal monitor which causes each of the transducer PZT disc to generate a transducer PZT disc waveform.

The ultrasound beam quality test apparatus further comprises a linear actuator. The linear actuator comprises a metal plate. The metal plate is attached to the linear actuator and is vertically adjustable by way of the linear actuator. The metal plate extends across the top surface of the fetal heart rate transducer. A linear actuator controller operates the linear actuator.

The memory is encoded with instructions that when executed by the microprocessor perform the step of setting the height of the metal plate to an ultrasound beam focal distance, by way of the linear actuator. In operation, the top surface of the fetal heart rate transducer and the metal plate are opposed with only an air gap therebetween.

Processing continues by oscillating, by way of the linear actuator, the metal plate between closer to and further from the top surface of the fetal heart rate transducer to generate a selected simulated fetal heartbeats per minute. In operation, the transducer PZT disc waveform is reflected off of the metal plate and received at the transducer PZT disc, and determining, by way of the fetal monitor, if the fetal heart rate transducer is recording a fetal heart rate that is substantially the same as the selected simulated fetal heartbeats per minute indicating the fetal heart rate transducer is operating correctly.

Additional features and advantages are realized through the techniques of the present invention. Other embodiments and aspects of the invention are described in detail herein and are considered a part of the claimed invention. For a better understanding of the invention with advantages and features, refer to the description and the drawings.

BRIEF DESCRIPTION OF THE FIGURES

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

FIG. 1 illustrates one example of a fetal monitor and placement of an improved fetal heart rate transducer and a tocodynamometer transducer on a patient;

FIGS. 5-9 illustrate examples of an improved fetal heart rate transducer;

FIG. 10 illustrates one example of a perspective view of an improved fetal heart rate transducer that comprises more than one belt slot;

FIGS. 12-16 illustrate examples of an improved fetal heart rate transducer belt loop style;

FIGS. 17-21 illustrate examples of an improved fetal heart rate transducer belt button style;

FIG. 25 illustrates one example of a method of using an improved fetal heart rate transducer;

FIG. 26 illustrates exemplary embodiments that can be used interchangeably with the methods of the present invention;

FIG. 30 illustrates one example of Doppler equations for frequency shift calculations;

FIGS. 36-37 illustrates exemplary embodiments that can be used interchangeably with the methods of the present invention.

Figure 2:
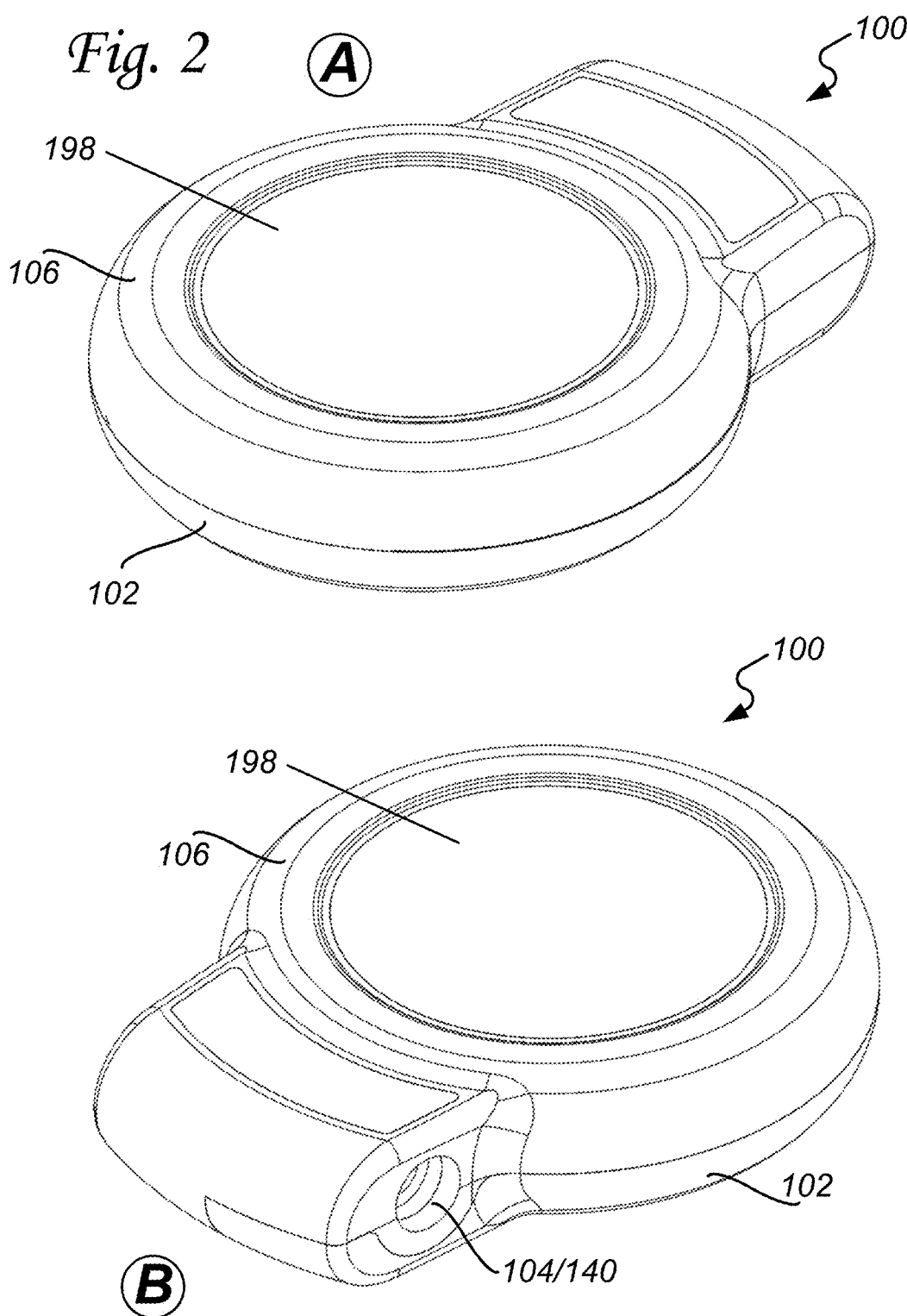
FIG. 2 illustrates one example of a bottom perspective view of an improved fetal heart rate transducer.

The detailed description explains the preferred embodiments of the invention, together with advantages and features, by way of example with reference to the drawings.

DETAILED DESCRIPTION OF THE INVENTION

For pre-birth applications, the most common method to obtain fetal heart rate is by using an ultrasound (US) transducer which is to be placed externally on the pregnant woman's abdomen. The ultrasound signal is received by piezo-electric crystals Lead Zirconate Titanate/PZT Discs and appropriately filtered. As the heart rate signal is contained in the very noisy received ultrasound Doppler signal, the ultrasound transducer must be placed directly over the fetal heart of the fetus which is approximately located on the lower left part of the abdomen.

Industry ultrasound transducers include Philips Avalon models M2736A, M2736AA, M2726A, Ref #867246, Avalon CL Ref #866076, and preceding HP medical model M1356A, 15245A. These models of transducers use 7 PZT (Lead Zirconate Titanate) discs in each transducer that are 10 millimeters (mm) in diameter with a center resonant frequency of 1 MHz (+/−100 Hz).

Other industry ultrasound transducers include the GE Corometrics model 5700AAX (Belt Loop Style), 5700BAX (Belt Button Style), NAUTILUS 5700LAX (Belt Loop Style), NAUTILUS 5700HAX (Belt Button Style) and Ref #2108346-001 (Combo/Belt Button and Loop Style). These models of transducers use 9 PZT (Lead Zirconate Titanate) discs that are 11.9 mm in diameter with a center resonant frequency of 1.151 MHz.

In operation, PZT discs vibrate in thickness mode (transverse/along the axis) when excited with respective frequency signals and produce an ultrasonic beam in two directions along the perpendicular axis of the PZT discs, one in the front surface that is coupled to the abdomen of the patient and a second in the opposite direction inside the transducer head cavity towards the top plastic case. The excitation pulse of 1 MHz with a repetition rate of 3 kHz is applied in Philips ultrasound transducers and 1.15 MHz with a repetition rate of 2 kHz or 4 kHz (depending on single or dual Channel use and the fetal monitor model) is applied in GE Corometrics Nautilus transducers. The same PZT discs act as transmitters as well as receivers of the reflected ultrasonic pulse waveform (echo signal).

Philips transducers have 7 PZT discs glued to the plastic surface. The frontend printed circuit board (PCB) is glued to the plastic surface and the backend PCB is mounted on top of the frontend PCB (models M2736A, M2736AA, M2726A, Ref #867246, and Avalon CL Ref #866076) by way of two dual header connectors that are in the direct pathway of the ultrasound beam emitted from the PZT discs. In these models, the PZT discs and frontend PCB are adhered to the plastic surface using a one-part silicone adhesive.

The frontend PCB has a pulse transmit-receiver, decoupling circuit, amplifier, and filter circuit to process ultrasound echo signals received from the beating fetal heart. The output analog signal (Doppler shift signal) is proportional to the rate of movement of the fetal heart. The backend PCB comprises the central processing unit (CPU) which converts analog Doppler signal to a digital signal that represents the fetal heart rate (FUR). The digital signal is communicated to a Philips Avalon fetal monitor (model FM 20, 30, 40, or 50) by way of a cable using a CAN (controlled area network) protocol or wirelessly for Philips model M2726A and Ref #866076 through base station unit model M2720A and Ref #866075 respectively.

Corometrics transducer models 5700AAX, 5700BAX, NAUTILUS 5700LAX, NAUTILUS 5700HAX, and Ref #2108346-001 have 9 PZT discs glued to the plastic surface and a frontend PCB mounted with self-tapping aluminum screws on stand-offs (without threaded metal inserts) above the 9 PZT discs. For these models of transducers, the frontend PCB doesn't have any active circuit component but rather only a single in-line nine-segment 47 ohm resistor network. A coaxial cable connects the transducer to the GE Corometrics fetal monitor through a 12-pin circular connector where 3 connections are for actual signal transmission and one short link across 2 pins of the connectors which is used for transducer recognition. For these models of transducers, the bottom side of the frontend PCB is a shield plane (connected to earth ground on the fetal monitor) to minimize stray electric field coupling to the PZT discs. The center core of the coaxial cable has two conductors, a positive signal conductor is connected to all 9 PZT discs' positive electrodes through the 47 ohm resistor network, and a negative signal conductor is connected to the negative electrode of the PZT disc. In these models, the PZT discs are adhered to the plastic surface using a one-part silicone adhesive.

The prior industry transducer models mentioned above have a number of shortcomings that are overcome in the present invention. Such shortcomings include intermittent signals or spurious noise that can be characterized by bonding that fails and standoffs that crack due to press-fitted metal inserts or self-tapping screws that allow the PZT discs and frontend PCB to become loose or vibrate, and an inability to detect cable wire shorts, breaks, and intermittent disconnects. Such intermittent signal misbehavior due to these and other shortcomings can cause the transducer not to work at all, or perhaps worse display the wrong fetal heart rate such as excessively high or low heart rates when connected to the patient as well as when not connected to the patient at all.

In general, the ultrasound Doppler signal requires complex electrical signal processing and filtering due to the very noisy (EMI) environment in hospitals as various electronic and RF communication equipment are used in the vicinity.

The present invention overcomes prior transducer shortcomings of ultrasound Doppler signal inaccuracy and transducer reliability through a number of improvements. These improvements include transducer mechanical stability, ultrasound accuracy by way of improved PZT disc bonding with the transducer enclosure, cable fault/failsafe detection electrical circuit improvements, and methods of use. In this regard, the present invention overcomes the fundamental shortcomings of prior industry transducer models 15245A, M1356A, Avalon M2736A, M2736AA, Ref #867246, Avalon CTS M2726A, Avalon CL Ref #866076, and GE Corometrics models 5700AAX, 5700BAX, NAUTILUS 5700LAX, NAUTILUS 5700HAX, NAUTILUS Ref #2108346-001. The improved fetal heart rate transducer 100/200 operates and functions in strict adherence to basic pulse Doppler principles to provide consistent and accurate fetal heart rate (FHR) detection by eliminating all the root causes/sources of the intermittent/spurious behavior of prior industry transducers. An advantage, in the present invention, is that is improves fetal heart transducer fetal heart rate (FHR) detection reliability, and transducer durability reducing costs and equipment downtime, making it easier to use for both the patient as well as the clinical end user.

For disclosure purposes, the improved fetal heart rate transducer 100/200 can be referred to as improved fetal heart rate transducer 100, improved fetal heart rate transducer 200, the fetal heart rate transducer 100/200, the fetal heart rate transducer 100, the fetal heart rate transducer 200, transducers 100/200, transducer 100, or transducer 200.

Another advantage, in the present invention, is to rectify the fundamental design shortcomings in Philips fetal ultrasound transducer models 15245A, M1356A, Avalon M2736A, M2736AA, Ref #867246, Avalon CTS M2726A, Avalon CL Ref #866076, GE Corometrics ultrasound model 5700AAX, 5700BAX, NAUTILUS 5700LAX, NAUTILUS 5700HAX and NAUTILUS Ref #2108346-001 to provide a continuous measurement of FHR without spurious readings to provide reliable data for patient management.

Another advantage, in the present invention, is to provide a plurality of methods of use, one of which includes a quantitative ultrasound integrity assessment procedure to assess the performance of PZT discs after bonding to the plastic surface and the accuracy of each of the PZT disc output as a basic sensor (transmitter and receiver of ultrasound wave/beam) element.

Another advantage, in the present invention, is to provide a comprehensive design shortcoming correction process for physically intact OEM transducers (with 100% OEM parts from Philips/GE-Corometrics) that is less expensive and more reliable than the new replacement from the respective manufacturers that have fundamental design shortcomings that result in performance issues, especially spurious FHR readings.

Turning now to the drawings in greater detail, it will be seen that in FIG. 1 there is illustrated one example of a fetal monitor 302 and placement of an improved fetal heart rate transducer and a tocodynamometer transducer on a patient 502. In an exemplary embodiment, a fetal monitor 302 can be interconnected with an improved fetal heart rate transducer 100/200 by way of a cable 330 or wirelessly. The transducer 100/200 can be secured to the abdomen of patient 502 by a belt 364 proximate to fetus 504. The belt can secure a transducer by way of a button 136/212 style attachment or as shown in FIG. 1 with a belt loop 202 style attachment.

A tocodynamometer (Toco) transducer 304 can also be interconnected by a cable 334 or wireless connection with a fetal monitor. In this regard, the fetal monitor can display both the Toco 332 readings as well as the fetal heart rate (FHR) 326 and associated Toco waveforms 324 as well as the FHR waveform 328.

In an exemplary embodiment, the ultrasound transducer 100/200 construction comprises either 7 or 9 PZT discs 112/218. It is connected to the fetal monitor 302 through a shielded cable 330. A signal of 1 or 1.15 MHz from a stable frequency generator is applied to PZT discs 112/218 for about 100 microseconds and then the timing control circuit switches the PZT discs 112/218 to a receiving mode for about 200 microseconds. The received signal is operationally coupled to a preamplifier. The pulsed transmission and reception continue with a fixed repetition rate. The preamp output represents the received ultrasound echo signal with Doppler shift frequencies proportional to the fetal heartbeating of fetus 504. The preamp output signal is conditioned through a phase discriminator/detector to extract the Doppler shift frequency envelope, digitized through an A/D converter, filtered, and finally processed either directly by microcontroller 408 or through one more preceding stage of digital signal processor (DSP) or field programmable gate array (FPGA) or a complex programmable logic device (CPLD), or other suitable circuit block implementation to strike the balance between the cost and performance for digital signal processing. The microcontroller (MCU) then outputs the results to peripheral units such as a display, strip chart recorder, speaker, or other peripheral units as may be required and/or desired in a particular embodiment.

Referring to FIG. 2, there is illustrated one example of a bottom perspective view of an improved fetal heart rate transducer 100. Reference 'A' is a front view and reference 'II' is a back view. The improved fetal heart rate transducer 100 comprises a top case 102, a bottom case 106, and a cable connector 104 hole/cavity for cable 330 strain relief 354 and PCB connector 352. The cable connector 104/140 secures one end of cable 330 to the improved fetal heart rate transducer 100. The other end of cable 330 plugs into the fetal monitor 302.

In an exemplary embodiment, the top case 102 and the bottom case 106 can be manufactured from plastic or other suitable materials. Additionally, the top case 102 and the bottom case 106 can be over-molded with polyurethane rubber.

Figure 3:
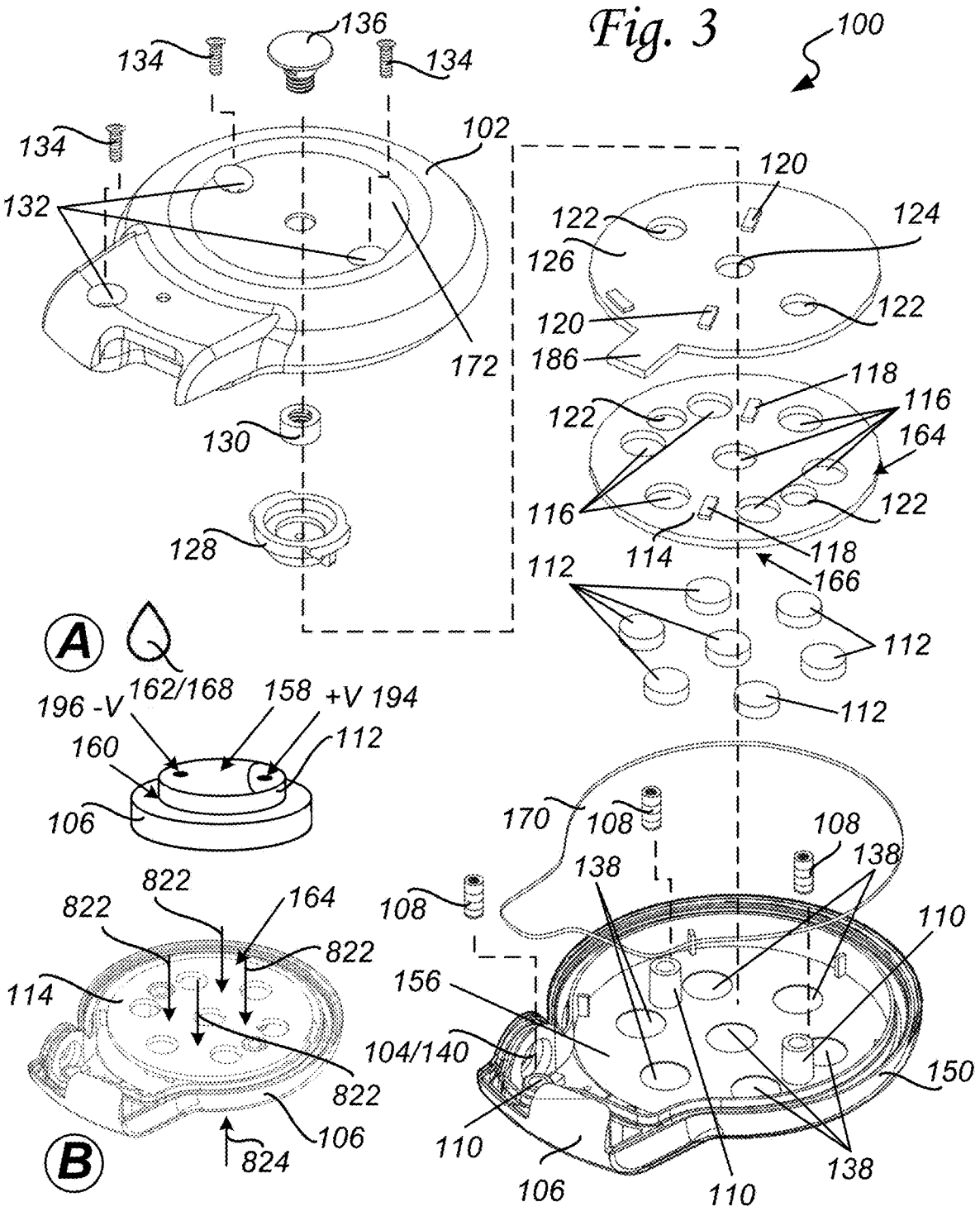
FIG. 3 illustrates one example of an assembly view of an improved fetal heart rate transducer.

Referring to FIG. 3, there is illustrated one example of an assembly view of an improved fetal heart rate transducer 100. In an exemplary embodiment, a top case 102, and a bottom case 106 fasten together. The top case comprises a top case exterior surface 172 and a top case interior surface 174 that is better illustrated in at least FIG. 4. More than one recessed opening 132 is positioned over the top of each of the cupped standoffs 148 and non-cupped standoff 182, which is better illustrated in at least FIG. 4, allowing machine screws 134 which are precision shoulder screws to pass through and be counter-sunk in the top exterior surface 172 when the top case 102 and the bottom case 106 are fastened together. Better illustrated in at least FIG. 31, strain relief 354 and rubber boot 358A/358B secure the cable 350A by way of the cable connector 104/140 hole/cavity to the transducer 100. Rubber boot 358A style is used with transducer 100 and rubber boot 358B style is used with transducer 200.

The bottom case 106 comprises an interior surface 156. The interior surface 156 has de-embossed or raised more than one piezo-electric crystal (PZT) pad 138, and more than one standoff 110. More than one metal insert 108 is molded into place within the standoff 110 as the bottom case 106 is fabricated in the mold with plastic resin. In this regard, an advantage, in the present invention, is that the metal inserts 108/222/224 are not press-fitted creating stress in the standoffs 110 that leads to cracking. Such cracks allow the components to loosen, shift, or vibrate causing misreading FHR and other operational errors. Rather, the metal inserts 108/222/224 are placed in the mold at the time the bottom case 106/204 is fabricated or otherwise molded so that there is no stress with respect to the interface between the metal inserts 108/222/224 and the standoffs 110 eliminating the possibility of stress cracks forming over time.

The improved fetal heart rate transducer 100 further comprises more than one piezo-electric crystal (PZT) disc 112 having a top side 158 and an epoxy side 160. Such PZT disc 112 can be lead zirconate titanate discs or other types and kinds of PZT discs, as may be required and/or desired in a particular embodiment.

In prior transducers, bonding of the PZT discs to the plastic surface becomes weak as the one-part silicone adhesive used develops micro-cracks allowing air pockets and the partially anchored PZT disc movement that gives rise to ultrasound echo signal with Doppler frequency shift that gets translated as a spurious FHR.

In contrast and advantage, in the present invention, PZT disc bonding failures and spurious FHR shortcomings are overcome by utilizing a different PZT bonding approach and epoxy adhesive. In this regard, in an exemplary embodiment, in the fabrication of the improved fetal heart rate transducer 100, each of the PZT disc 112 adheres to the PZT pad 138 as follows; the interior surface 156 and the PZT disc 112 are cleaned with a mild soap solution, rinsed with deionized/distilled water, and air dried. An ultra slow-cure epoxy 162 is mixed and degassed in a vacuum for a degassing time period. In an exemplary embodiment, the ultra slow-cure epoxy 162 can be mixed as four parts resin to one part hardener, and the degassing time period can be in the range of 15 to 20 minutes.

The manner in which the PZT disc 112 adheres to the PZT pad 138 continues as follows with a drop of the degassed ultra slow-cure epoxy 162 being deposited in the center of the epoxy side 160 of each of the PZT disc 112/218 while the PZT disc 112/218 is resting on a horizontal surface with the epoxy side 160 up, or the PZT pad 138/232 while the bottom case 106/204 is resting on a horizontal surface. The drop of ultra slow-cure epoxy 162 is then allowed to self-level for a self-leveling time period. In an exemplary embodiment, the self-leveling time period can be in the range of 15 to 20 minutes.

In the present invention, the term "self-leveling" is intended to mean the process of allowing gravity to act on a liquid medium and/or a weight on a liquid medium to evenly distribute the liquid medium across a surface. In this regard, the liquid can be a drop of epoxy such as the slow-cure epoxy 168 and the ultra slow-cure epoxy 162 that are allowed to self-level under the force of gravity or under the weight of a PZT disc 112/218 placed on top of the epoxy 162/168. In operation, the epoxy is dispersed in a thin, smooth, horizontal, degassed, and uniformly thick manner, and objects placed on the epoxy 162/168 such as the PZT disc 112/218 self-level as well in a horizontal manner.

The manner in which the PZT disc 112 adheres to the PZT pad 138 continues as follows, as illustrated in at least FIG. 3, reference 'A', by placing the epoxy side 160 of each of the PZT disc 112 on each of the PZT pad 138 while the bottom case 106 is resting on a horizontal surface. The PZT disc 112 and the bottom case 106 assembly are then allowed to self-level under the weight of the PZT disc 112 and cure for a cure time period. In an exemplary embodiment, the cure time period can be in the range of a minimum of 68 hours.

Prior transducers that bond the frontend PCB 114 to the plastic case 106 suffer shortcomings of bond failure between the plastic case and the frontend PCB that results in the frontend PCB coming loose from the plastic partially or entirely. In both cases, frontend PCB vibration or worse complete and continuous movement gives rise to an ultrasound echo signal with Doppler frequency shift that gets translated as a spurious FHR. When frontend PCB 114 becomes partially or completely loose, the backend PCB (main CPU PCB) 126 also vibrates or intermittently moves resulting Doppler shift in reflected echo signal that translates to spurious FHR, and in addition, various electrical signal issues such as noise are caused as the electrical connections through two header pin connectors 118/120 with frontend PCB 114 go through make-break cycles.

In contrast and advantage, in the present invention, the frontend PCB bonding failures and spurious FHR shortcomings are overcome by utilizing a different frontend PCB bonding approach. In this regard, in an exemplary embodiment, the improved fetal heart rate transducer 100 further comprises a frontend printed circuit board (PCB) 114 that has a PCB top side 164 and a PCB epoxy side 166. Each of the PZT discs 112 electrically interconnects with and is operationally related to the frontend PCB 114.

In an exemplary embodiment, in the fabrication of the improved fetal heart rate transducer 100, the frontend PCB 114 adheres to the interior surface 156 of the bottom case 106 as follows, the PCB epoxy side 166 of the frontend PCB 114 is cleaned with isopropyl alcohol, and air dry. A slow-cure epoxy 168 is mixed and degassed in a vacuum for a degassing time period. In an exemplary embodiment, the slow-cure epoxy 168 can be mixed as two parts resin to one part hardener, and the degassing time period can be in the range of 8 to 10 minutes.

The manner in which the frontend PCB 114 adheres to the interior surface 156 of the bottom case 106 continues as follows by coating the PCB epoxy side 166 of the frontend PCB 114 with a uniform layer of the slow-cure epoxy 168 while the frontend PCB 114 is resting on a horizontal surface with the PCB epoxy side 166 up. The uniform epoxy layer is allowed to self-level for a self-leveling time period. In an exemplary embodiment, the self-leveling time period can be in the range of 10 to 15 minutes. The frontend PCB 114 is then placed in position with the PCB epoxy side 166 in contact with the interior surface 156 of the bottom case 106. The frontend PCB 114 is then allowed to self-level under its weight for a self-leveling time period. In an exemplary embodiment, the frontend PCB 114 self-leveling time period can be in the range of 10 to 15 minutes.

The manner in which the frontend PCB 114 adheres to the interior surface 156 of the bottom case 106 continues as follows, as illustrated in at least FIG. 3 reference 13', by clamping 822/824, for a cure time, the frontend PCB 114 and the bottom case 106 at more than one pressure point 822. The pressure points 822 are symmetrically located on the surface of the top side 164 of the frontend PCB 114. In an exemplary embodiment, the cure time can be in the range of 24 to 36 hours.

Transducer failure, intermittent operation, and spurious FHR in prior transducers are often caused by bonding shortcomings such as weak, failed, cracked, airgap ridden, and/or uneven bonding thickness between the PZT discs 112/218 and if bonded to the plastic case the frontend PCB 114. Additionally, transducer failure, intermittent operation, and spurious FHR in prior transducers can be caused by press-fitting metal inserts into plastic standoffs that eventually cause the standoffs to crack creating vibration and motion of the backend PCB 126/216, top case 102/210A/210B, and other internal parts.

To illustrate this point, first consider normal transducer operation where the transducer is mechanically stable, and absent any component vibrations. The PZT disc emits ultrasound waves from both disc faces, the top surface face and the bottom surface face. The bottom surface face of the disc when perfectly epoxied to the plastic substrate through which the ultrasound wave of 1 MHz frequency travels out of the transducer 100.

Inside the transducer, a backend PCB 126 is installed about 2.8 mm distance above the PZT disc top surface face and orientated in a parallel plane (transverse to the emitted ultrasound wave travel). In this example, since the transducer 100 is mechanically stable, and absent any component vibrations there is no movement of the backend PCB 126, top plastic case 102, or the PZT disc 112. While the backend PCB 126 and the top case 102 do reflect ultrasound waves, the reflected frequency perceived will be the same as 1 MHz that was transmitted by the PZT disc 112. Allowing only the reflected frequency from the bottom surface face 198 that is coupled to the patient 502 to vary engendering correct transducer operation and readings.

Now consider abnormal transducer operation, where the transducer is mechanically unstable, in that the adhesive layer on one of the PZT discs is failing, acting like a rubber cushion, allowing the PZT disc to vibrate up-down with 50 micrometers (0.05 mm) amplitude just for 100 milliseconds (0.1 sec). In this case, the reflected 1 MHz wavefront from the stationary backend PCB will be perceived as a little higher frequency than 1 MHz when the PZT disc moves towards the backend PCB and a little lower frequency than 1 MHZ when the PZT disc moves away from the backend PCB. The frequency change perceived/detected by the PZT disc will be proportional to the velocity of the PZT disc itself (as an observer in receiving mode) in either direction. As an example, if the PZT disc velocity was 1 micrometer per microsecond when it moved towards the main CPU PCB (backend PCB 126), it would measure the reflected wave from stationary PCB as frequency 1.002915 MHz (2.915 kHz more than the originally transmitted frequency of 1 MHz). If the disc moves away from the PCB (towards the bottom case) with the same velocity, the reflected wave from the stationary PCB would be measured as a frequency of 0.997093 MHz which is lower by 2.906 kHz as compared to the originally transmitted ultrasound pulse of 1 MHz. In this example, for purposes of calculations, the velocity of sound in the air medium (between the PZT disc and the backend PCB) is taken as 343 m/s at 20° C.

When the ultrasound transducer is strapped to the abdomen of the patient to monitor the fetus, the PZT discs receive useful echo signal (at the bottom surface face 198/256 of the transducer) from the fetal heart (that is beating) with Doppler frequency shift proportional to the heart movement as well as from the internal parts (on the top surface face side of PZT disc), including from the backend PCB, top case, metal threaded inserts and any of these internal components that make spurious/intermittent movement in micrometers, making the Doppler shift echo signal results very unreliable for FHR detection.

The error in FHR detection worsens if one or more PZT discs are loose as the loose disc acts as a moving observer/receiver and echo signals from perfectly stationary targets (PCB, top case, metal inserts) contribute to the Doppler shift frequency proportional to the PZT disc movement. Table 820 in FIG. 30 illustrates the Doppler equations for the frequency shift calculation. The third and fourth rows in the table represent the condition where the backend PCB and top case are stationary and a PZT disc is intermittently moving, acting as an observer.

During a patient's respiration cycle, the abdominal belt 364 experiences slight pressure changes and if there is a movement of the PZT disc, frontend PCB, backend PCB, top case, or other components, such movement translates into a spurious reading of the FHR. The movement of components can also be facilitated by the use of self-tapping screws that loosen over a short span of time. Any unintended moving object/target (continuously or intermittently) directly in the path of the ultrasound beam on either side of PZT discs (bottom side towards fetus, top side internal to transducer head) produces a Doppler shift echo proportional to the velocity of the moving object/target and gets translated into spurious FHR readings even when there is no fetus present.

An advantage, in the present invention, to overcome these unintended intermittent/spurious FHR readings is the use of an approach for bonding the PZT discs 112/218 and frontend PCB 114 using a two-part ultra slow-curing epoxy 162 on the PZT discs 112/218 and a two-part slow-curing epoxy 168 on the frontend PCB 114 to achieve the bond strength necessary to withstand test impact forces. Such, impact forces are generated in a drop test by dropping the transducer from a height of 22 feet onto a hard concrete floor.

During laboratory testing, of the bonding materials and approach in the present invention, and utilizing the 22-foot drop test mentioned above we found that the plastic parts, connectors, top case, or bottom case, were suspectable to damage but the PZT discs and frontend PCB bonding remained intact. In other words, for the PZT discs and the frontend PCB to be separated from the transducer bottom case surface, the plastic substrate should first have to be destroyed physically, which means the bonding is rated for use for the lifetime of the transducer.

Figure 4:
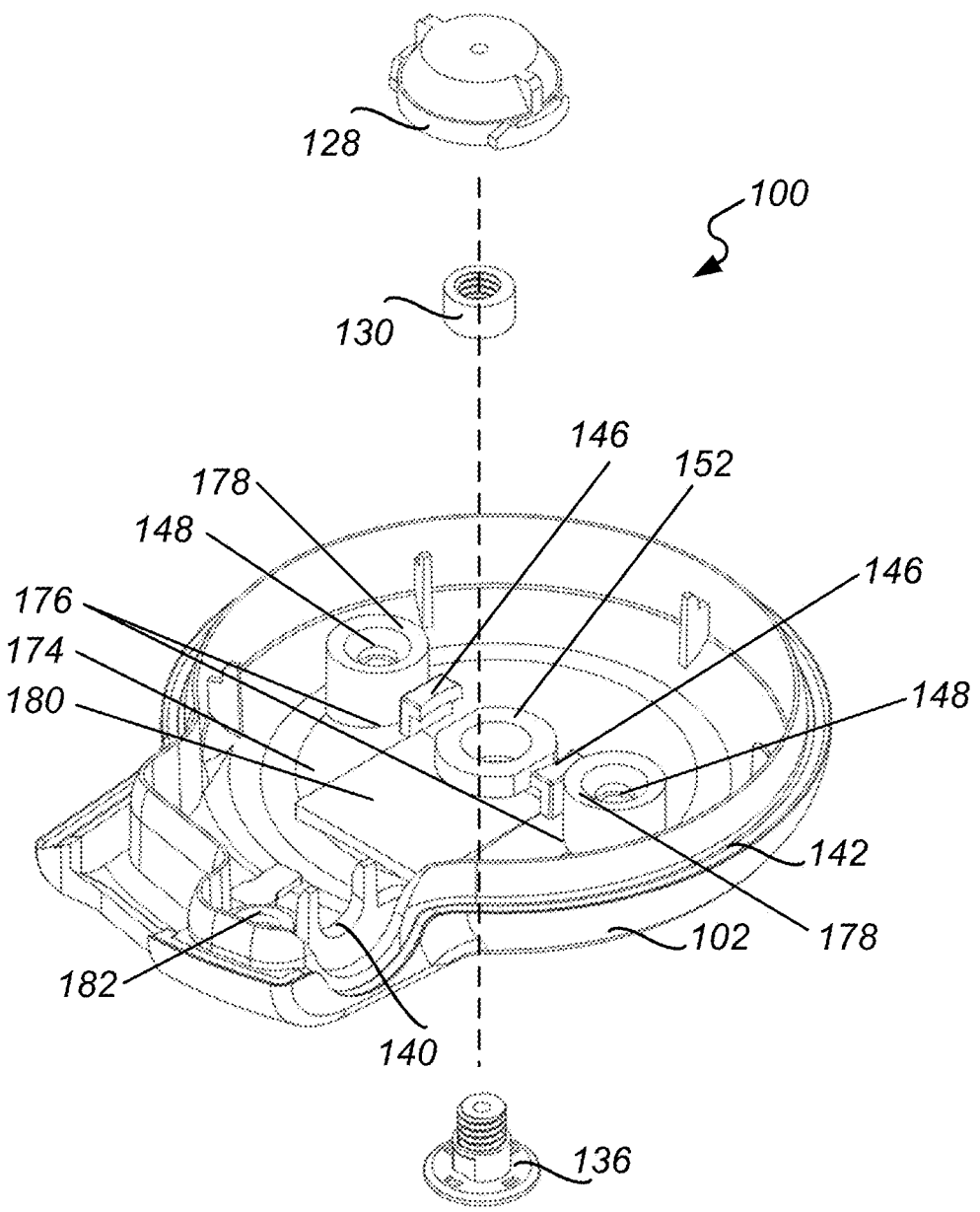
FIG. 4 illustrates one example of a top case assembly view of an improved fetal heart rate transducer.

In an exemplary embodiment and with reference to FIGS. 3 and 4, where FIG. 4 illustrates one example of a top case assembly view of the improved fetal heart rate transducer 100, the top case 102 comprises a top case top side 172, a top case interior surface 174, a top groove 142, a button fastener retainer 152, an inclined plane 180, more than one retaining clip 146, and more than one cupped standoff 148. The cupped standoffs 148 comprise a cupped standoff bottom 176 that is integrally formed with the top case interior surface 174, and a cupped standoff top 178 that has a raised ridge edge around the circumference of the cupped standoff 148 top creating a cavity that is sized to interconnect with the standoff 110 on the bottom surface 106 after passing through the frontend PCB 114 and the backend PCB 126 in a manner that allows the raised ridge edge 178 to contact and immobilize the backend PCB 126 from movement when the top case 102 and the bottom case 106 are fastened together.

In an exemplary embodiment, a threaded button fastener 130 can be molded into the button fastener retainer 152 from the top case interior surface 174 side of the top case 102. A threaded button 136 can be inserted through the top case 102 top side into the threaded button fastener and tightened, securing the threaded button to the top case of the top case 172. A cover 128 covers the button fastener retainer 152 and the threaded button fastener 130. The cover is secured under the retaining clip 146 in a manner that the inclined plane 180 applies force to cover 128 holding it from displacement from the retaining clip 146. A gasket 170 can be fitted into the top groove 142 and a bottom groove 150 forming a seal between the top case 102 and the bottom case 106 when fastened together. The bottom case 106 comprises the bottom groove 150.

Referring to FIGS. 4-8 are illustrated examples of an improved fetal heart rate transducer 100. FIG. 5 illustrates one example of a bottom case 106 where reference 'A' is an exterior surface view and reference 13' is an interior surface view. In an exemplary embodiment, the height of a raised island pad 184 can be selected so that a PCB tab 186 that is part of the backend PCB 126 (see at least FIG. 2) can rest on island pad 184 limiting backend PCB 126 motion/vibration when the transducer 100 is assembled.

Figure 6:
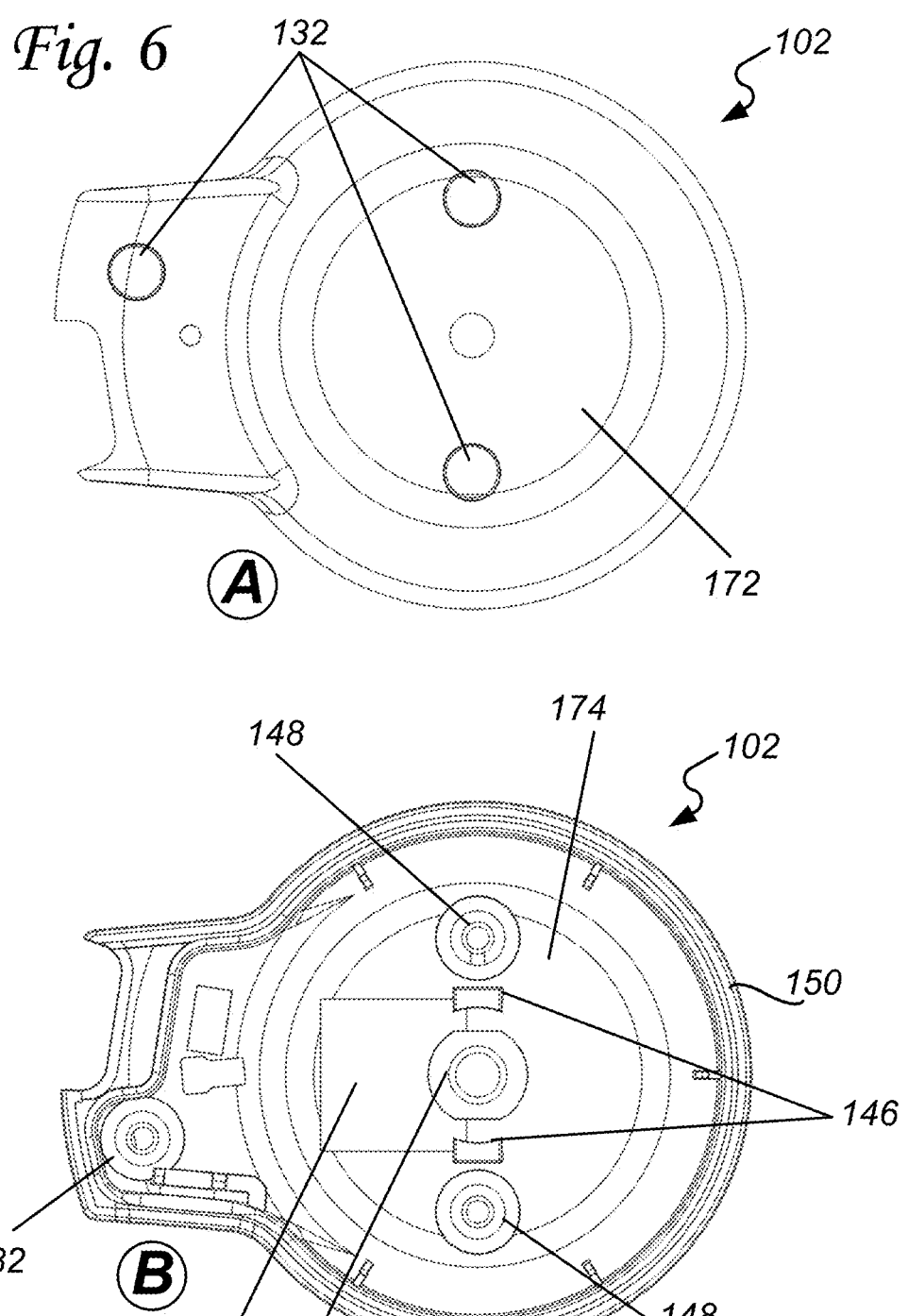

Referring to FIG. 6 there is illustrated one example of a top case 102 view where reference 'A' is an exterior surface view and reference 13' is an interior surface view. The top case comprises a top case exterior surface 172 and a top case interior surface 174. More than one recessed opening 132 is positioned over the top of each of the cupped standoffs 148 and non-cupped standoff 182 allowing machine screws 134 that are precision shoulder screws with longer thread length than used in prior transducers to pass through and be counter-sunk to the top exterior surface 172 when the top case 102 and the bottom case 106 are fastened together.

Figure 8:
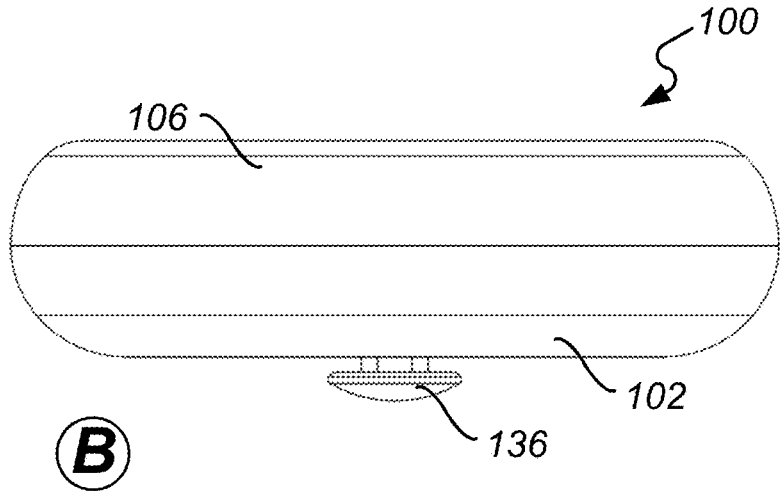
Figure 9:
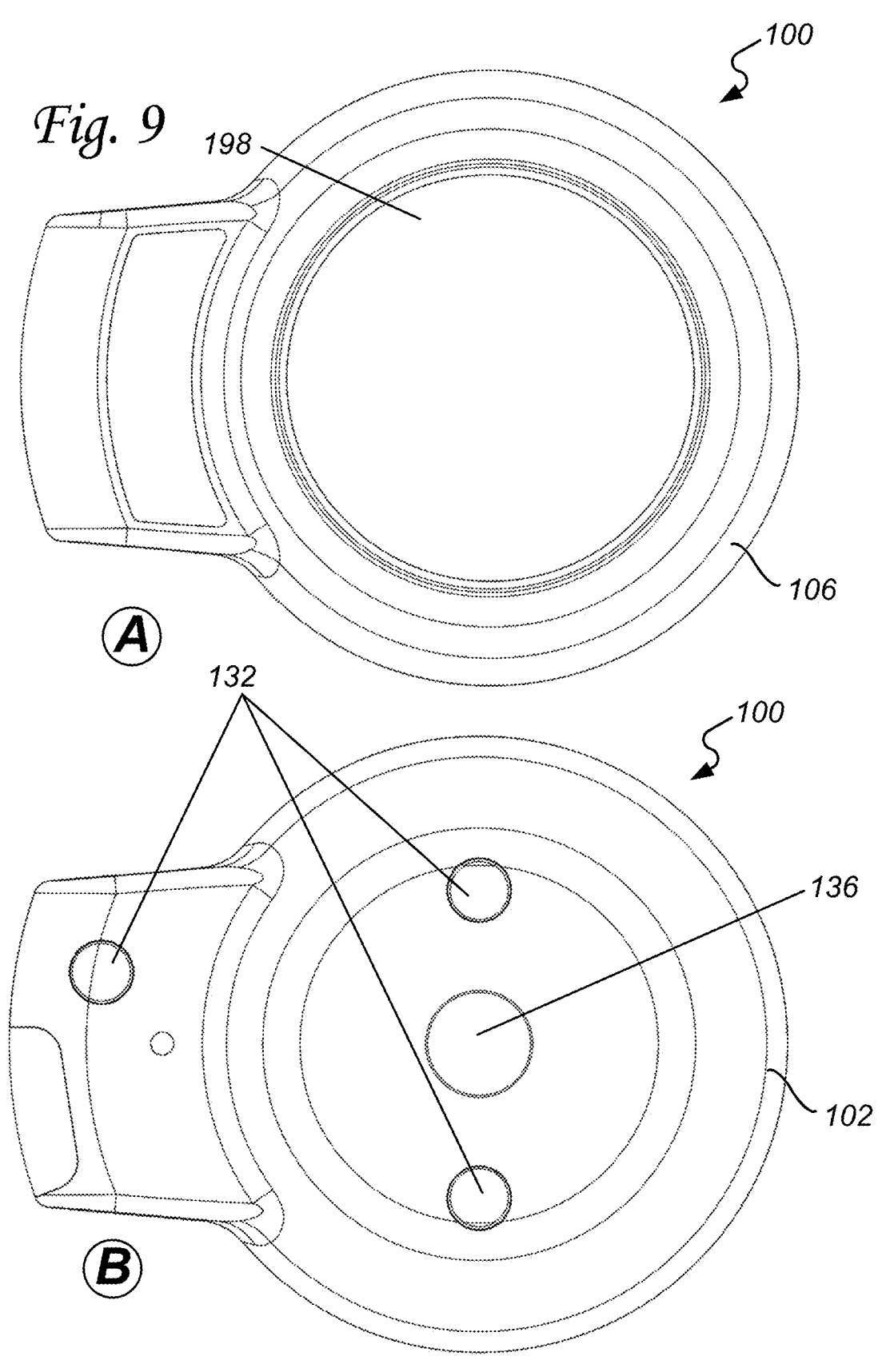

Referring to FIG. 7 reference 'A' there is illustrated as one example of a left side view of the assembled improved fetal heart rate transducer 100, and reference 13' is a right side view of the improved fetal heart rate transducer 100. FIG. 8 reference 'A' illustrates one example of a back side view of improved fetal heart rate transducer 100, and reference 13' illustrates one example of a front side view of improved fetal heart rate transducer 100. FIG. 9 reference 'A' illustrated one example of a bottom side view of improved fetal heart rate transducer 100, and reference 13' illustrates one example of a top side view of improved fetal heart rate transducer 100.

Referring to FIG. 10, there is illustrated one example of a perspective view of an improved fetal heart rate transducer 200 that comprises more than one belt slot 202. In an exemplary embodiment, reference 'A' is an exterior surface view of the top side of the improved fetal heart rate transducer 200, and reference 13' is the exterior surface view of the bottom side of the improved fetal heart rate transducer 200. In operation, a belt 364 can be passed through belt slot 202 to secure the improved fetal heart rate transducer 200 to patient 502.

Figure 12:
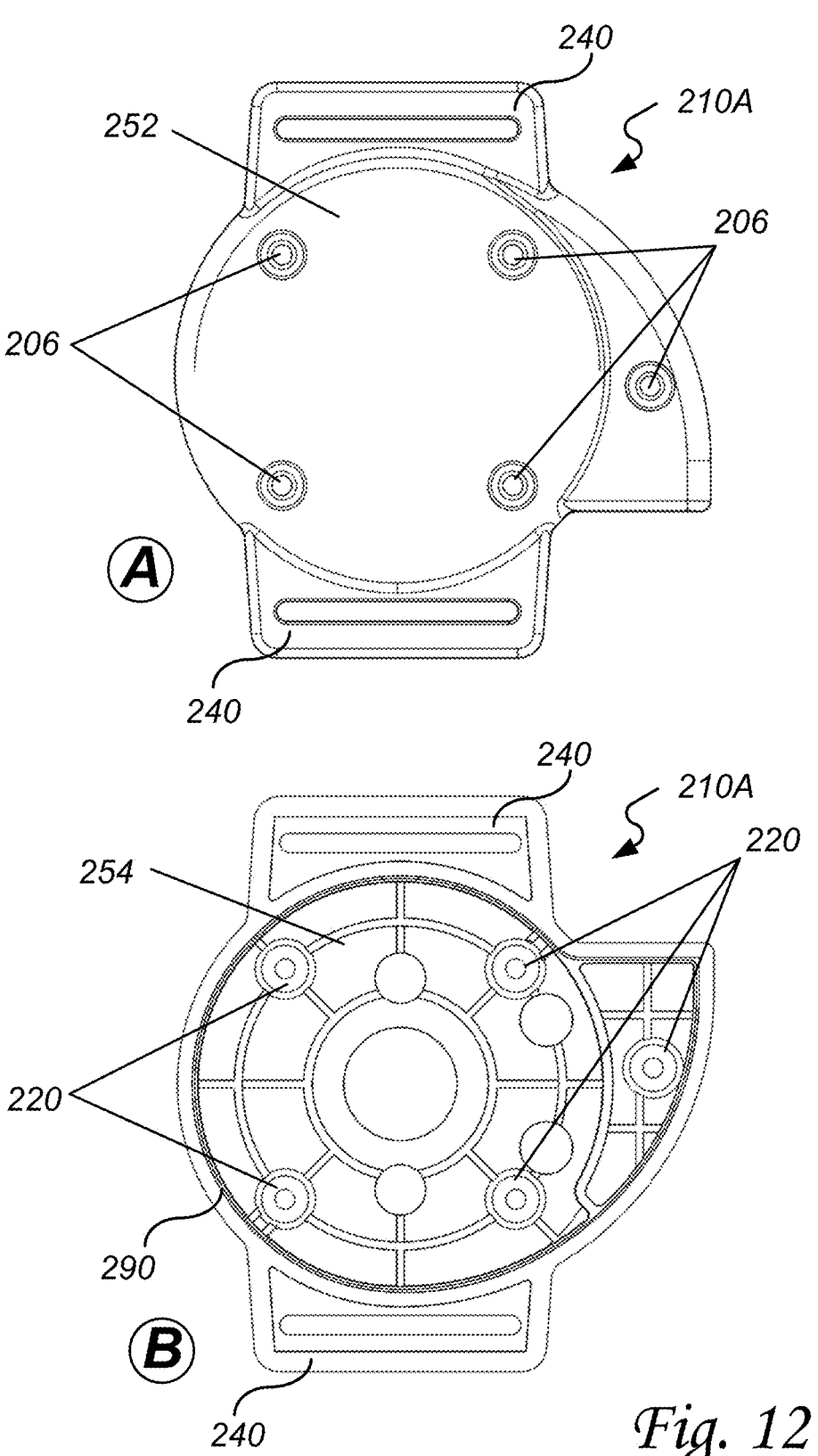

The top case comprises a top case exterior surface 252 and a top case interior surface 254 (as better illustrated in at least FIG. 12. More than one recessed opening 206 is positioned over the top of each of the top case standoffs 220 allowing machine screws 250 to pass through and be counter-sunk to the top exterior surface 252 when the top case 210A or 210B and the bottom case 204 are fastened together. With regards to attaching to the belt 364 and positioning and securing the improved fetal heart rate transducer 200 around patient 502, top case 210A has belt slots, and top case 210B has button 212. Both tops 210A and 210B cases can be used interchangeably in the present invention. Rubber boot 358A style is used with transducer 100 and rubber boot 358B style is used with transducer 200.

In an exemplary embodiment, the top case 210A/210B and the bottom case 204 can be manufactured from plastic or other suitable materials.

Figure 11:
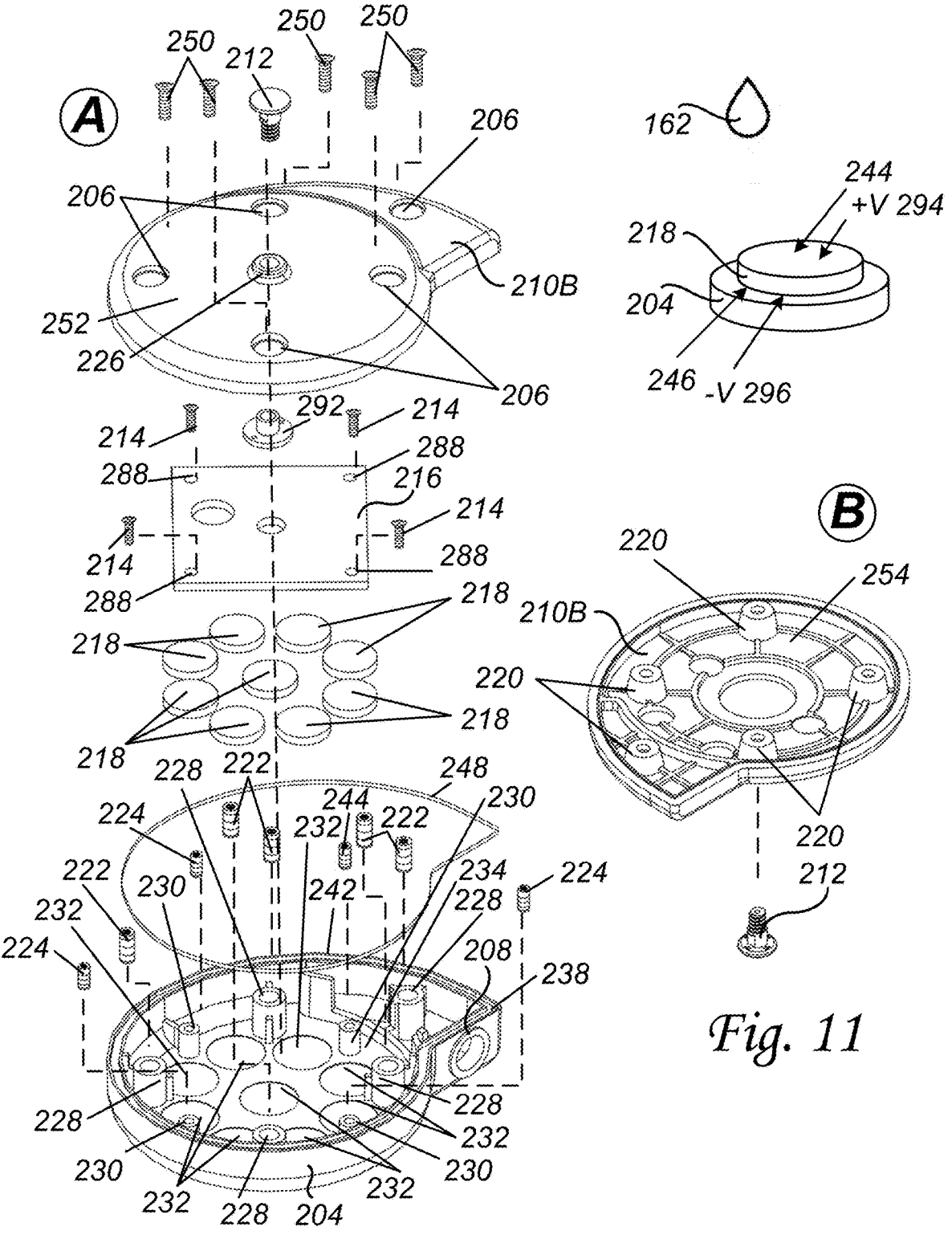
FIG. 11 illustrates one example of an assembly view of an improved fetal heart rate transducer.

Referring to FIG. 11, there is illustrated one example of an assembly view of an improved fetal heart rate transducer 200. In an exemplary embodiment, a top case 210A or 210B, and a bottom case 204 fasten together. As better illustrated in at least FIG. 12, the top case 210A/210B comprises a top case exterior surface 252 and a top case interior surface 254. More than one recessed opening 206 is positioned over the top of each of the top case standoffs 220 allowing machine screws 250 to pass through and be counter-sunk in the top exterior surface 252 when the top case 210A/210B and the bottom case 204 are fastened together.

The bottom case 204 comprises an interior surface 234. The interior surface 234 has de-embossed or raised more than one piezo-electric crystal (PZT) pad 232, and more than one standoff 228/230. More than one metal insert 222/224 is molded into place within the standoff 228/230 as the bottom case 204 is fabricated in the mold with plastic resin. In this regard, an advantage, in the present invention, is that the metal inserts are not press-fitted into the standoffs 228/230 creating stress in the standoffs 228/230 that leads to cracking in the standoffs 228/230. Such cracks allow the components inside to loosen, shift or move with vibration and adjustment that cause misreading (FHR) and other operational errors. Rather, the metal inserts 222/224 are placed in the mold at the time the bottom case 204 is fabricated or otherwise molded so that there is no stress with respect to the interface between the metal inserts 222/224 and the standoffs 228/230 eliminating the possibility of stress cracks forming over time.

In prior transducers, only three standoffs with no inserts, using self-tapping screws instead, were utilized leaving one corner of the frontend PCB 216 loose to vibrate causing FHR errors. In contrast and advantage, in the present invention, four standoffs 230 have metal inserts 244 molded in at the time the bottom case 204 is formed. This approach secures each of the four corners of the frontend PCB 216 with machine screws 214 into the metal inserts 244 that hold the frontend PCB 216 from vibrating at each corner without cracking the standoffs 230.

The improved fetal heart rate transducer 200 further comprises more than one PZT disc 218 having a top side 244 and an epoxy side 246. Such PZT disc 218 can be lead zirconate titanate discs or other types and kinds of PZT discs, as may be required and/or desired in a particular embodiment.

In an exemplary embodiment, in the fabrication of the improved fetal heart rate transducer 200, each of the PZT disc 218 adheres to the PZT pad 232 as follows the interior surface 234 and the PZT disc 218 are cleaned with a mild soap solution, rinsed with deionized/distilled water, and air dried. An ultra slow-cure epoxy 162 is mixed and degassed in a vacuum for a degassing time period. In an exemplary embodiment, the ultra slow-cure epoxy 162 can be mixed as four parts of resin to one part hardener, and the degassing time period can be in the range of 15 to 20 minutes.

The manner in which the PZT disc 218 adheres to the PZT pad continues as follows with a drop of the ultra slow-cure epoxy 162 being deposited in the center of the epoxy side 246 of each of the PZT disc 218 while the PZT disc 218 is resting on a horizontal surface with the epoxy side 246 up, or the PZT pad 232 while the bottom case 204 is resting on a horizontal surface. The drop of ultra slow-cure epoxy 162 is then allowed to self-level for a self-leveling time period. In an exemplary embodiment, the self-leveling time period can be in the range of 15 to 20 minutes.

In an exemplary embodiment, PZT Pads 232 can have a small cutout or notch at the perimeter to accommodate PZT disc types where one of the wire electrodes is bonded to the side epoxy side 246. In this regard, the small cutout allows the wire to egress the PZT pad 232 so the PZT disc 218 can sit flat on the PZT pad 232 surfaces.

The manner in which the PZT disc 218 adheres to the PZT pad 232 continues as follows by placing the epoxy side 246 of each of the PZT disc 218 on each of the PZT pad 232 while the bottom case 204 is resting on a horizontal surface. The PZT disc 218 and the bottom case 204 assembly are then allowed to self-level under the weight of the PZT disc 218 and cure for a cure time period. In an exemplary embodiment, the cure time period can be in the range of a minimum of 68 hours.

The improved fetal heart rate transducer 200 further comprises a frontend printed circuit board (PCB) 216. Each of the PZT disc 218 interconnects with and is operationally related to the frontend PCB 216.

In an exemplary embodiment, in the fabrication of the improved fetal heart rate transducer 200, the frontend PCB 216 comprises PCB mounting holes 288 that align with the standoffs 230. Machine screws 214 are placed through the PCB mounting holes 288 and secured into the metal inserts 224 that are formed into the standoffs 230 securing the frontend PCB 216 to the bottom case 204 using machine screws.

In an exemplary embodiment, and with reference to FIGS. 11 and 12, where FIG. 12 illustrates one example of a top case assembly view of the improved fetal heart rate transducer 200, the top case 210A comprises a top case top side 252, a top case interior surface 254, a top perimeter edge 290, a button fastener retainer 292 molded into the top case 210B, and more than one top case standoff 220.

In an exemplary embodiment, the top case 210A comprises more than one belt slot 240 through which a belt 364 can be secured. A gasket 248 can be fitted into a bottom groove 238 that engages the top perimeter edge 290 forming a seal between the top case 210A/210B and the bottom case 204 when fastened together. The bottom case 204 comprises the bottom groove 238.

In an exemplary embodiment, internal cavity surfaces 254/234 of top case 210A/210B and bottom case 204 of transducer 200 can be coated with electrically conductive material to form a Faraday cage shield for EMI. In prior transducers, over a period of time, the conductive layer oxidizes and peels off and loose flakes become the source of spurious FHR. An advantage, in the present invention, is that by utilizing and improved method to spray plating catalyst (Autocatalytic Plating process) onto the areas of the internal cavity surface 254/234 bonding is improved and spurious FHR caused by flaking is eliminated. In operation, paint masks are used to control the location of where the catalyst is dispersed on the internal cavity surfaces 254/234. In this regard, PZT pads 232 for PZT discs 232 are masked so that the catalyst is not deposited on the PZT pad 232 surface. The chemical make-up of the catalyst draws copper metal out of the plating solution, and deposits copper uniformly onto the catalyzed area. It is followed by electroless copper plating and finally, electroless nickel plating is applied to protect the copper from corrosion and abrasion.

Referring to FIGS. 12-21, there are illustrated examples of an improved fetal heart rate transducer 200. FIG. 12 illustrates in reference 'A' an exterior surface 252 views of a top case 210A that has belt slots 240, and in reference 'II' an interior surface 254 of a top case 210A that has belt slots 240. FIG. 13 illustrates in reference 'A' an exterior surface 256 of a bottom case 204, and an interior surface 234 of a bottom case.

Referring to FIG. 14, there is illustrated in reference 'A' a left side view of the improved fetal heart rate transducer 200, and in reference 13' a right side view of the improved fetal heart rate transducer 200. The bottom case 204 comprises a cable connector 208 hole/cavity for cable-strain relief installation. The cable connector 208 securing one end of cable 330 connects the improved fetal heart rate transducer 100/200 to the fetal monitor 500.

Referring to FIG. 15 reference 'A' illustrates one example of a front side view of the improved fetal heart rate transducer 100, and reference 13' illustrates one example of a back side view of the improved fetal heart rate transducer 200.

Figure 16:
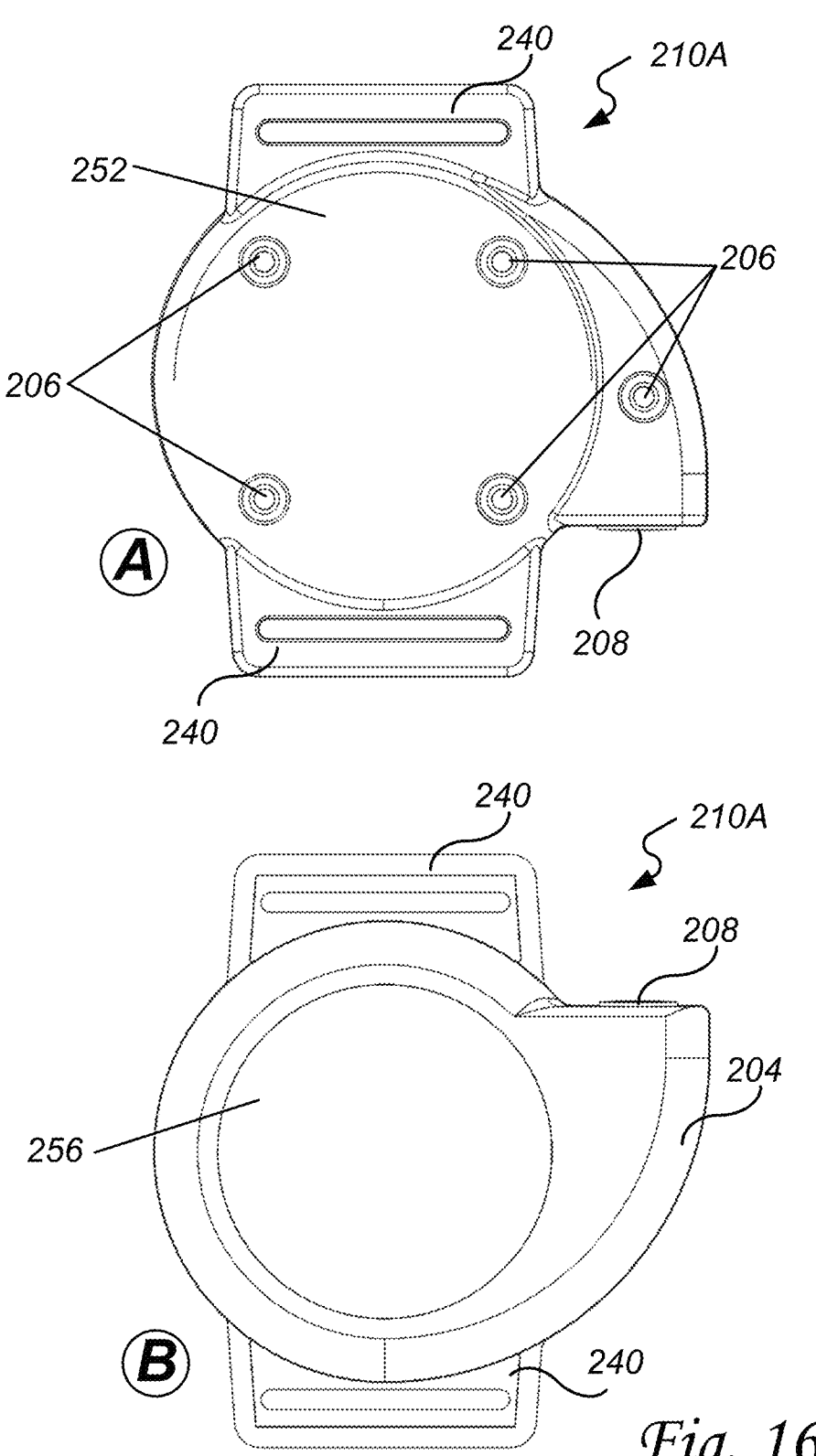

Referring to FIG. 16 reference 'A' illustrated one example of a top side view of the improved fetal heart rate transducer 200 with belt slots 240, and reference 13' illustrates one example of a bottom side view of the improved fetal heart rate transducer 200.

Referring to FIG. 17, there is illustrated one example of a perspective view of an improved fetal heart rate transducer 200 that has button 212. In an exemplary embodiment, reference 'A' is an exterior surface 252 view of the top side of the improved fetal heart rate transducer 200, and reference 13' is the exterior surface 256 view of the bottom side of the improved fetal heart rate transducer 200.

Referring to FIG. 18, there is illustrated in reference 'A' one example of the top surface 252 of a top case 210B having a button fastener retainer 226, and in reference 13' the bottom surface 254 of the top case 210B. In an exemplary embodiment, the top case 210B comprises a top case exterior surface 252 and a top case interior surface 254. More than one recessed opening 206 is positioned over the top of each of the top case standoffs 220 allowing machine screws 250 to pass through and be counter-sunk to the top exterior surface 252 when the top case 210A or 210B and the bottom case 204 are fastened together. With regards to attaching to the belt 364 and positioning and securing the improved fetal heart rate transducer 200 around patient 502, top case 210A has belt slots, and top case 210B has button 212. Both tops 210A and 210B cases can be used interchangeably in the present invention.

Referring to FIG. 19, there is illustrated in reference 'A' one example of a left side view wherein the top case 210B is configured with a button fastener retainer 226, and in reference 13' the bottom surface 254 of the top case 210B.

FIG. 20 illustrates in reference 'A' one example of a front side view wherein the top case 210B is configured with a button fastener retainer 226 with molded in button fastener retainer 292, and in reference 13' a back side surface 254 of the top case 210B. FIG. 21 illustrates in reference 'A' one example of a top 210B side view wherein the top case 210B is configured with a button fastener retainer 226 with molded in button fastener retainer 292, and in reference 13' a bottom 204 side view.

In an exemplary embodiment, button fastener retainer 226 with molded in button fastener retainer 292 does not get knocked off in drop tests from 18 ft height to concrete floor and hence more likely to last the lifetime of the transducer 200 as it can only be taken off if the top case 210B is physically destroyed.

In an exemplary embodiment, the improved fetal heart rate transducer 200, the top case 210A comprises a top case top side 252, a top case interior surface 254, a top perimeter edge 290, a button fastener retainer 226 with molded in insert 292 molded into the top case 210B, and more than one top case standoff 220.

In an exemplary embodiment, a threaded button fastener 212 can be inserted into the button fastener insert 292 and tightened securing the threaded button to the top case 204. A gasket 248 can be fitted into a bottom groove 238 that engages the top perimeter edge 290 forming a seal between the top case 210A/210B and the bottom case 204 when fastened together. The bottom case 204 comprises the bottom groove 238.

Figure 22:
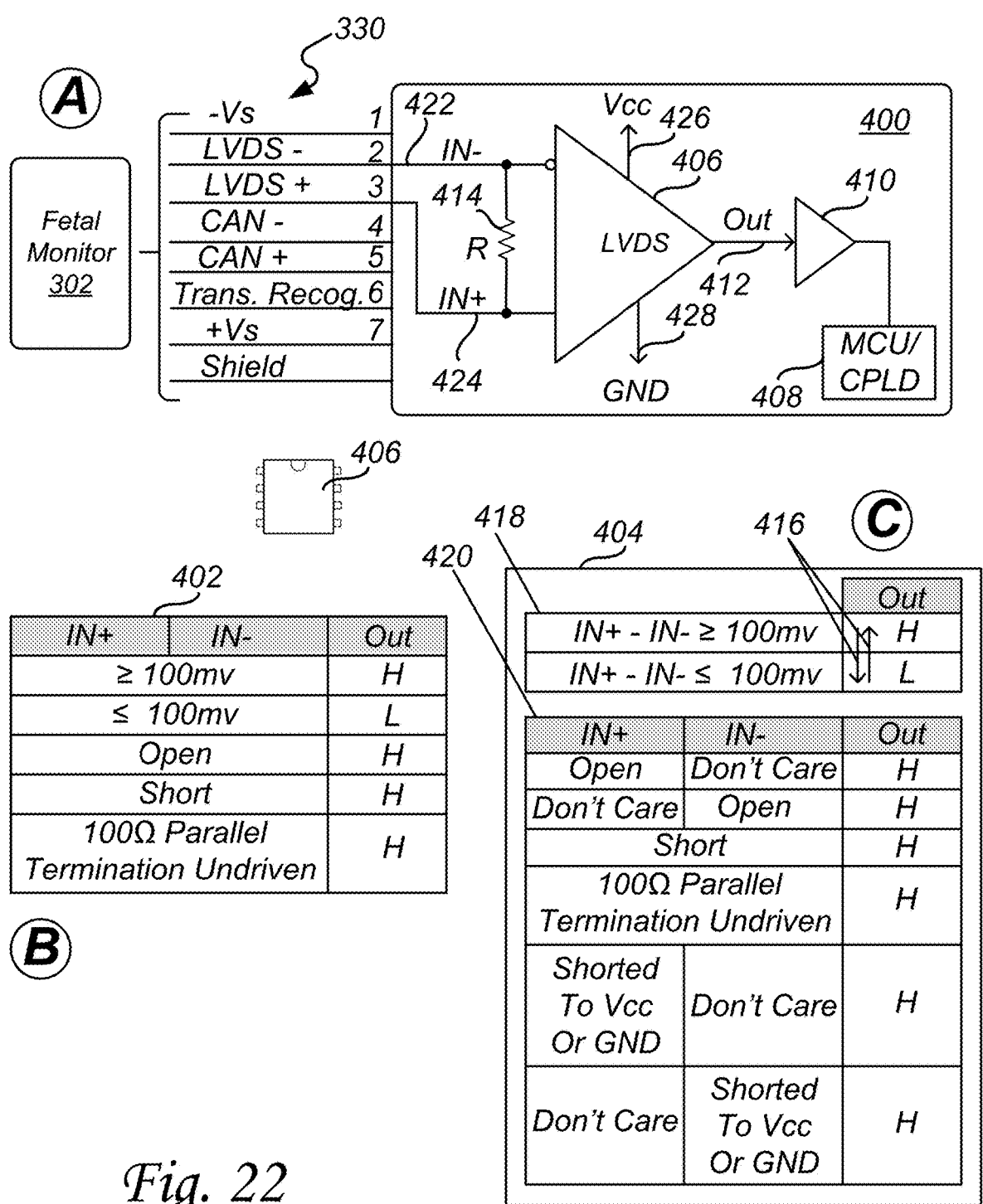
FIG. 22 illustrates one example of a low-voltage differential signal receiver circuit and logic state tables.

Referring to FIG. 22, there is illustrated one example of an electronic control system 400 which is part of the backend main CPU PCB 126 that comprises a low-voltage differential signal (LVDS) receiver circuit 406 and logic state tables. An advantage, in the present invention, is the operation of an electronic control system 400 that comprises the LVDS receiver circuit 406. In this regard and in contrast to the present invention, prior transducers that process the ultrasound signal inside the transducer rather than the fetal monitor, do so based on the state table shown in reference 'B'. As such, these types of prior transducers generate distorted and noisy outputs when a cable wire makes intermittent connections or is broken which causes spurious FHR readings even when there is no patient or fetus is dead after going through stress during a monitoring session.

With reference to the seven-conductor (plus the shield) cable 330 illustrated in at least FIG. 22, if any of the five conductors on pins 1, 4, 5, 6, or 7, breaks (electrically open) then the transducer completely stops working but if one of the remaining two conductor connector pins 2 or 3 (LVDS +/−) breaks (electrically open) then the transducer becomes noisy and gives spurious FHR readings without transmitting the ultrasound beam. These two conductors (pins 2 and 3) carry a 1 MHz reference signal from the fetal monitor to the transducer head that is processed through the LVDS receiver chip on the backend PCB. In an exemplary embodiment, pin 1 is −Vs, pin 2 is LVDS −, pin 3 is LVDS +, pin 4 is controller area network (CAN) Bus −, pin 5 is CAN Bus +, pin 6 is Transducer Recognition, pin 7 is +Vs, and cable shield is connected to earth ground on the fetal monitor connection end of the cable 330.

The present invention overcomes this shortcoming by providing a failsafe LVDS circuit 406 that is encoded to operate based on the state table in reference 'C'. In an exemplary embodiment and in contrast to prior transducers, in the present invention, the improved LVDS receiver chip 406 has a failsafe circuit and encoded state table operation that outputs a logic high signal (H) state that is translated by the FHR monitor as an equipment malfunction error. Such error conditions can be displayed to alert the operator. In the alternative, the improved LVDS receiver chip 406 outputs a square pulse, logic high and low change with the same frequency as the input signal when the correct operation is detected (cable conductors are physically and electrically intact between the fetal monitor and the LVDS receives both inputs IN+ and IN−). The improved LVDS receiver chip 406 output can be latchable such that when an error condition is detected even if intermittently once, the improved LVDS receiver chip 406 output is latched logic high until the system is reset. This prevents temporary error conditions from allowing the operator to believe the cable is operating correctly.

In an exemplary embodiment, the LVDS receiver chip 406 functioning in accordance with state table 404 can be a single semiconductor 406 or a combination of more than one semiconductor that accomplishes the desired operations, as may be required and/or desired in a particular embodiment.

Resetting of the error condition can be done by way of cycling power on the fetal monitor, replacing the cable 330 which also cycles power on the transducer, or other suitable resetting methods, as may be required and/or desired in a particular embodiment.

In operation, the failsafe LVDS 406 circuit not only detects intermittent or broken wire (from cable 330) conditions but also detects both inputs LVDS +/−(twisted pair conductors) open or short-circuited. The present invention, improved LVDS receiver IC semiconductor 406 with input failure detection logic circuit as shown in reference 'A' and 'C'. The output of the LVDS 406 is then received by the microcontroller (MCU) or CPLD 408 by way of, as needed, additional latching, tri-state buffering, other types of buffering, or other signal processing circuitry 410.

In an exemplary embodiment, such improved LVDS semiconductor 406 can be fabricated in a form factor and pin-compatible manner so that the improved failsafe LVDS 406 can be a direct semiconductor part replacement in prior transducers that suffer from the shortcomings mentioned above. Alternatively, separate failsafe circuitry 400 can be incorporated into existing frontend PCB 114 or backend PCB 126 to detect cable failed conditions, as may be required and/or desired in a particular embodiment.

In an exemplary embodiment and with reference to reference 'C', an electronic control system 400 comprises a low voltage differential signal (LVDS) receiver having an IN+ input (cable 330 pin 3), an IN− input (cable 330 pin 2), and an output 412. The LVDS receiver 406 monitors the operational status of the fetal heart rate transducer 100/200 by generating at output 412 a first logic state corresponding to a logic level high (H) or a second logic state corresponding to a logic level low (L) as follows:

when the difference between the IN+ 424 and the IN− 422 is greater than or equal to 100 mv the output 412 is the first logic state (such as logic high (H));

when the difference between the IN+ 424 and the IN− 422 is less than or equal to 100 mv the output 412 is the second logic state (such as a logic low (L));

when the IN+ 424 is open (not connected) the output 412 is the first logic state (such as logic high (H));

when the IN− 422 is open (not connected) the output 412 is the first logic state (such as logic high (H));

when the IN+ 424 and IN− are connected by a first resistance 414, which is configured as an undriven parallel termination, the output 412 is the first logic state (such as logic high (H));

when IN+ 424 is shorted to the supply voltage (Vcc) 426 or ground 428 the output 412 is the first logic state (such as logic high (H));

when IN− is shorted to Vcc 426 or ground 428 the output 412 is the first logic state (such as logic high (H)); and when IN+ 424 and IN− 422 are shorted together the output 412 is the first logic state (such as logic high (H)).

In operation, the first logic state is either logic level high (H) or logic level low (L) and the second logic state is the opposite of the first logic state. For disclosure purposes and not as a limitation, as illustrated in FIG. 22 and described above the first logic state has been selected as logic level high (H) and the second logic state has been selected as a logic level low (L).

Additionally, the first logic state is latched on output 412, requiring a reset to clear latching of output 412, when the first logic state persists on output 412 for more than a predetermined error condition time period. In this regard, while normal operation 418 sees the difference between IN+ 424 and IN− 422 transitioning 416 between greater than or equal to 100 mv and less than or equal to 100 mv causing output 412 to transition 416 between the first logic state and the second logic state if the output 412 remains at the first logic state for an extended period of time (exceeding the predetermined error condition time period) something is wrong as illustrated in the state table 420 and the output 412 is latched to the first logic state which stops FHR detection until the transducer 100 is reset. A reset can be done by unplugging the transducer 100 from the fetal monitor 302 (removing power temporarily), changing cables, or other suitable reset methods. The predetermined error condition time period can be set in the range of milliseconds to seconds, as may be required and/or desired in a particular embodiment.

An advantage, in the present invention, is that by latching the output 412 when an error condition in the state table 420 is detected, displaying an incorrect FHR is prevented. As one example, the error condition when one of IN+ 424 or IN− 422 is open (not connected) an erroneous waveform can be created that is interpreted by the fetal monitor 302 as an FHR in the range of 220 beats per minute even when the transducer 100 is not connected to a patient 502 or fetus is dead during the monitoring event. The present invention solves this error condition and others by latching output 412 to the first logic state when output 412 has been at the first logic state for a time period that exceeds the predetermined error condition time period preventing incorrect FHR readings from being displayed on the fetal monitor 302 and requiring a technician to remove from service broken cables 330 and/or transducer 100.

Figures 23, 24:
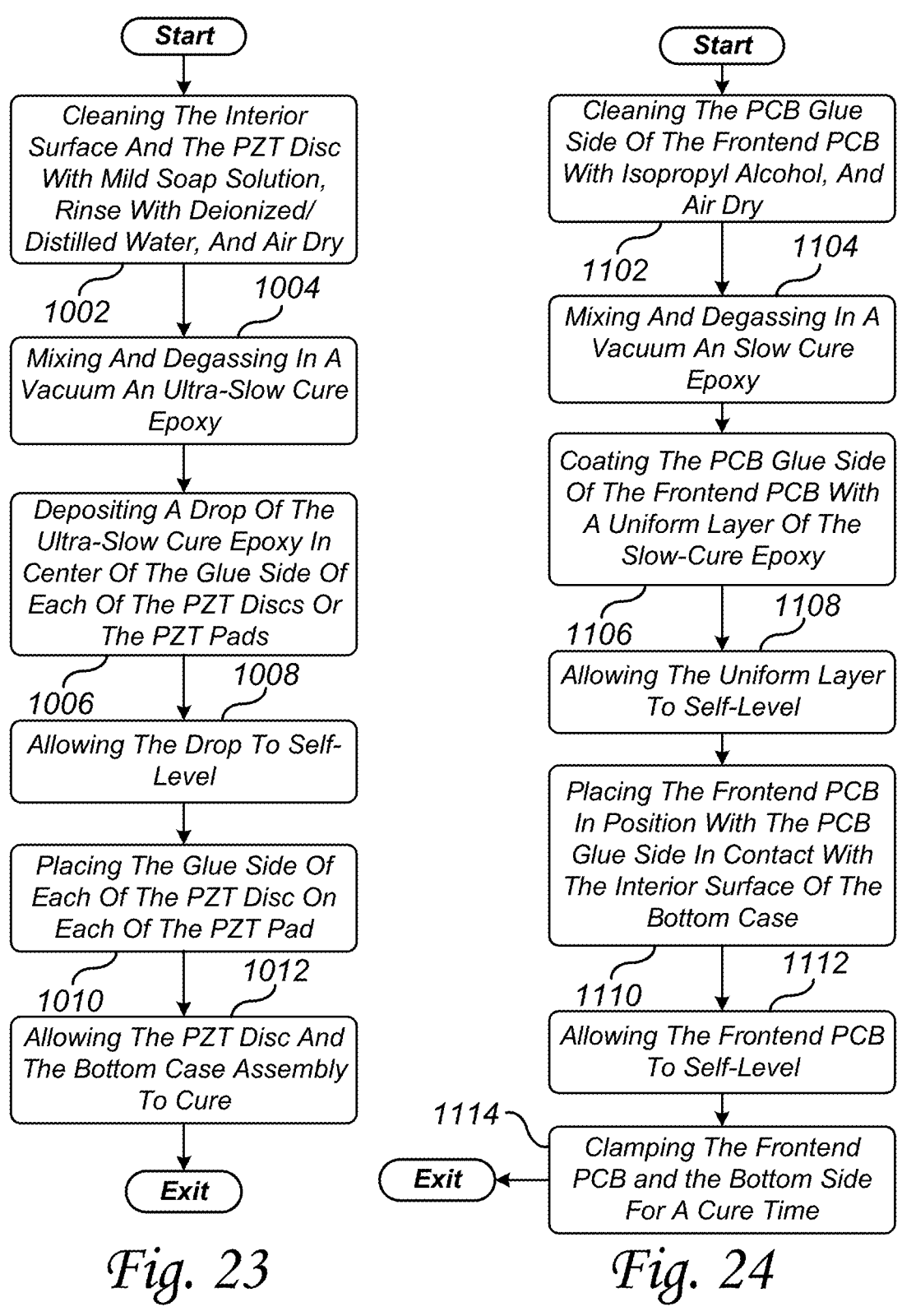
FIG. 23 illustrates one example of a method of adhering PZT discs to PZT pads.
FIG. 24 illustrates one example of a method of adhering the frontend PCB to the interior surface of the bottom case.

Referring to FIG. 23, there is illustrated one example of a method of adhering PZT discs 112/218 to PZT pads 138/232. In an exemplary embodiment, the method begins in step 1002.

In step 1002, the interior surface 156/234 of the bottom case 106/204 and surfaces of the PZT discs 112/218 are cleaned with a mild soap solution, rinsed with deionized/distilled water, and air dried.

In an exemplary embodiment, if the transducer is being reworked, then patches of old epoxy should be removed. Such patches of old epoxy can often be removed by placing them is a multi-frequency ultrasound cleaner until clean. The PZT disc 112/218 and frontend PCB 114 should not be scraped as scratches will not allow uniform bonding film of epoxy and the ultrasound beam profile will deteriorate due to increased diffraction of the wavefront from the scratched area that would result in the ultrasound beam quality parameters to be non-compliant with OEM specifications approved by FDA.

In most cases, it is relatively easy to remove old epoxy from the plastic surface as there are often air pockets. One method is to soak the area with distilled warm water for 15 to 20 minutes and carefully peel off the old glue using forceps with the aid of looking through a 10× magnifier lens or a microscope. In all cases regardless of the method of glue removal used, utmost care should be taken so that the plastic surface is not scratched. The second method of old glue removal can include using isopropyl alcohol or white vinegar. Once the old glue is completely removed, the step of cleaning can proceed.

Once cleaned, the PZT discs 112/218, frontend PCB 114, and plastic substrate of the bottom case 106/204 can be inspected under a 10× magnifier lens/microscope to ensure there are no scratches or dust particles. Care should be taken to avoid touching any bonding surfaces after cleaning is finished to avoid introducing oils or contaminants on the bonding surfaces.

In an exemplary embodiment, the cleaned plastic bottom case 106/204, the PZT discs 112/218, and frontend PCB 114 (surface to be epoxied facing upward) should be placed on a work table that is perfectly horizontally level and has a top surface with mirror finish RA 0.1 μm (micrometer). Care should also be observed by wearing static protection wristband to handle the frontend PCB 114 as CMOS integrated circuits, and other components are susceptible to electrostatic discharge damage. The method moves to step 1004.

In step 1004, an ultra slow-cure epoxy 162 is mixed and degassed in a vacuum, for a first degas time period.

In an exemplary embodiment, the ultra slow-cure epoxy 162 is mixed in four-parts resin, one-part hardener ratio (4:1) by volume in a pot. The pot is then placed in a vacuum chamber to degas for 15 to 20 minutes at 26 in Hg. Once degassed, a 5 ml control sample of the ultra slow-cure epoxy 162 is placed on a 0.1 mm thick polyethylene paper and set aside as a batch quality control sample. The method then moves to step 1006.

In step 1006, a drop of the ultra slow-cure epoxy 162 is deposited in the center of the epoxy side 160/246 of each of the PZT discs 112/218 while the PZT disc 112/218 is resting on a horizontal surface with the epoxy side 160/246 up, or the PZT pad 138/232 while the bottom case 106/204 is resting on a horizontal surface.

In an exemplary embodiment, a 3 ml DYMAX syringe or similar is filled with degassed ultra slow-cure epoxy 162 and placed in a stepper dispenser such as a DYMAX STEPPER, or other suitable stepper dispensers that is configured for 0.2 ml epoxy drops for 10 mm diameter PZT discs and 0.24 ml for 11.9 mm diameter PZT discs. At the start of epoxy dispensing the first epoxy shot is discarded to prepare the stepper dispenser. Each successive epoxy shot is dispensed at the center of each horizontally laid PZT disc. One filling of a 3 ml syringe should deliver approximately 14 shots (plus the first shot unused) to cover 14 PZT discs. In the alternative, the stepper dispenser can place the epoxy drops on the PZT pads instead of the PZT discs and the method continued. The method then moves to step 1008.

In step 1008, the drop of ultra slow-cure epoxy 162 is allowed to self-level for a self-leveling time period. In an exemplary embodiment, the ultra slow-cure epoxy 162 drops are allowed to self-level for 15 to 20 minutes on the PZT disc surface 112/218. In the alternative, when the ultra slow-cure epoxy 162 drops can be placed on the PZT pads 138/232 instead of the PZT discs 112/218, the bottom case 106/204 can be maintained on a level surface for the self-leveling time period and the method continued. The method then moves to step 1010.

In step 1010, the epoxy side 160/246 of each of the PZT discs 112/218 is placed on each of the PZT pads 138/232 while the bottom case 106/204 is resting on a horizontal surface.

In an exemplary embodiment, the PZT discs 112/218 are picked up by holding the edges diagonally and placed on the PZT pads 138/232. In an exemplary embodiment, when the frontend PCB 114 has previously been bonded to the interior surface 156 of the bottom case 106, the PZT discs 112/218 can be placed through the PZT holes 116 in the frontend PCB 114 in the center, and a one-part silicone dots can be placed on the diagonally opposite positions of the PZT disc 112 and frontend PCB 114 proximate the edge of the PZT hole 116 to hold the PZT disc 112 in the center of the PZT hole 116. The method then moves to step 1012.

In step 1012, the PZT disc 112/218 and the bottom case 106/204 assembly are allowed to cure for a cure time period. In an exemplary embodiment, the PZT disc 112/218 self-levels under its own weight during the cure time period. Such a cure time period can be a minimum of 68 hours and/or until the control sample develops a film formed on the polyethylene sheet that does not get pierced with a Shore A hardness durometer needle. The method is then exited.

Referring to FIG. 24, there is illustrated one example of a method of adhering the frontend PCB 114 to the interior surface 156 of the bottom case. In an exemplary embodiment, the method begins in step 1102.

In step 1102, the PCB epoxy side 166 of the frontend PCB 114 is cleaned with isopropyl alcohol, and air dry. The method then moves to step 1104.

In step 1104, a slow-cure epoxy 168 is mixed and degassed in a vacuum, for a degas time period.

In an exemplary embodiment, a slow-cure epoxy 168 is mixed by volume in a pot with two parts resin to one part hardener (2:1). The slow-cure epoxy 168 is then degassed by placing the pot in a vacuum chamber to a degas time period of 8 to 10 minutes at 26 inches of Hg. The method then moves to step 1106.

In step 1106, the PCB epoxy side 166 of the frontend PCB 114 is coated with a uniform layer of the slow-cure epoxy 168 while the frontend PCB is resting on a horizontal surface with the PCB epoxy side 166 up.

In an exemplary embodiment, a Teflon rod can be used to apply degassed slow-cure epoxy 168 to the PCB epoxy side 166 of the frontend PCB forming a uniform thin layer of the slow-cure epoxy 168. The method then moves to step 1108.

In step 1108, the uniform layer of the slow-cure epoxy 168 is allowed to self-level for a self-leveling time period. In an exemplary embodiment, the self-leveling time period can be 10 to 15 minutes. The method then moves to step 1110.

In step 1110, the frontend PCB 114 is placed in position with the PCB epoxy side 166 in contact with the interior surface 156 of the bottom case 102. In an exemplary embodiment, excess slow-cure epoxy 168 around the edges of the frontend PCB 114 can be wiped away prior to placing the frontend PCB 114 in the proper orientation on the interior surface of the bottom case 102. The method then moves to step 1112.

In step 1112, the frontend PCB 114 is allowed to self-level for a self-leveling time period. In this regard, the self-leveling time period can be 10 to 15 minutes allowing the frontend PCB 114 to self-level on its own weight. The method then moves to step 1114.

In step 1114, the frontend PCB 114 and the bottom case 102 can be clamped at more than one pressure point 822/824 for a cure time. The pressure points 822 are symmetrically located on the surface of the top side 164 of the frontend PCB 114.

In an exemplary embodiment, excess slow-cure epoxy 168 can be wiped from the edges of the frontend PCB 114 and/or interior surface 156 of the bottom case 102. The frontend PCB 114 and the bottom case 102 can then be clamped together in at least four spots 822 symmetrically placed on the frontend PCB 114. The slow-cure epoxy 168 cure time can be in the range of 24 to 36 hours depending on the room temperature.

In an exemplary embodiment, the slow-cure epoxy 168 bonding method can also be used for the over-molding polyurethane/elastomer cover on the top case 106 and bottom 106 cases to enhance the durability of the transducer 100.

Referring to FIG. 25, there is illustrated one example of a method of using an improved fetal heart rate transducer 100/200. In an exemplary embodiment, one method of using the improved fetal heart rate transducer 100/200 is in combination with a hydrophone 600 which is better illustrated in at least FIGS. 27 and 28. In this regard, reworked as well as new transducers can be checked to ensure that the PZT discs 112/218 and frontend PCB 114 are properly bonded to the bottom case 106/204. The method begins in step 1202.

In step 1202, an index plate 702 is coupled with an ultrasound coupling jelly 712 to an improved fetal heart rate transducer 100/200. In an exemplary embodiment, the index plate 702 has more than one PZT disc position hole 704 that corresponds to and correlates with the location of each of the more than one PZT disc 112/218 within the fetal heart rate transducer 100/200. The fetal heart rate transducer 100/200 comprises a top case and a bottom case that fastens to the top case. The bottom case comprises an interior surface. The interior surface 156/234 has de-embossed or raised more than one PZT pad 138/232, and more than one standoff 110/228/230. More than one metal insert 108/222/224 is molded into place within the standoff as the bottom case is fabricated. More than one PZT disc 112/218 has a top side 158/244 and an epoxy side 160/246.

Each of the PZT discs 112/218 adheres to the PZT pad 138/232 as follows, cleaning the interior surface 156/234 and the PZT disc 112/218 with mild soap solution, rinsing with deionized/distilled water, and air drying. Mixing and degassing in a vacuum, for a first degas time period, an ultra slow-cure epoxy 162.

Depositing a drop of the ultra slow-cure epoxy 162 in the center of the epoxy side 160/246 of each of the PZT discs 112/218 while the PZT disc 112/218 is resting on a horizontal surface with the epoxy side 160/246 up, or the PZT pad 138/232 while the bottom case 106/204 is resting on a horizontal surface. Allowing the drop of ultra slow-cure epoxy 162 to self-level for a first self-leveling time period. Placing the epoxy side 160/246 of each of the PZT discs 112/218 on each of the PZT pads 138/232 while the bottom case 106/204 is resting on a horizontal surface. And, allowing the PZT disc 112/218 and the bottom case 106/204 assembly to cure for a first cure time period. The method then moves to step 1204.

In step 1204, a transducer PZT disc transmits waveform 808 is recorded for each of the PZT discs 112/218, by way of an oscilloscope 812 that is operationally connected to a hydrophone 600 that is in a receive mode (602/614 connected together by switch 612), by placing a hydrophone PZT disc 604 that is bonded to plastic substrate 606 and operationally related to the hydrophone 600 into one of the PZT disc position hole 704 and recording one of the transducer PZT disc transmit waveform 808 corresponding to one of the PZT disc 112/218, and repeating by moving the hydrophone PZT disc 604 to a different one of the PZT disc position hole 704 until at least one of the transducer PZT disc transmit waveform 808 has been recorded at each of the PZT disc position hole 704. The method then moves to step 1206.

In step 1206, a determination is made as to whether each of the transducer PZT disc transmit waveform 808 is similar in amplitude 806, frequency 808, and repetition rate 810 indicating that the fetal heart rate transducer 100/200 is transmitting properly and that each of the PZT disc 112/218 is uniformly bonded to the interior surface of the bottom case of the fetal heart rate transducer 100/200.

In an exemplary embodiment, transducers 100/200 that are new, reworked, and/or post being drop tested on a concrete floor can be checked with this method to see if any of the PZT discs 112/218 have dislodged partially or completely.

Referring to FIG. 26, there are illustrated exemplary embodiments that can be used interchangeably with the methods of the present invention.

In step 1302, a transducer PZT disc receive waveform 808 is recorded for each of the PZT discs 112, by way of the oscilloscope 812. The oscilloscope 812 is operationally connected to the output of a pre-amp 622 of the fetal heartbeat transducer 100 while the hydrophone 600 is in a transmit mode (602/610 connected by way of switch 612). By placing the hydrophone PZT disc 604 bonded to substrate 606 into one of the PZT disc position hole 704 and recording one of the transducer PZT disc receive waveform 808 corresponding to one of the PZT disc 112, and repeating by moving the hydrophone PZT disc 604/606 to a different one of the PZT disc position hole 704 until at least one of the transducer PZT disc receive waveform 808 has been recorded for each of the PZT disc position hole 704. The method then moves to step 1304.

In step 1304, a determination is made if each of the transducer PZT discs receives waveform 808 is similar in amplitude 806, frequency 808, and repetition rate 810 indicating the fetal heart rate transducer 100 is receiving properly, and that each of the PZT disc 112 is uniformly bonded to the case of the fetal heart rate transducer 100.

In step 1306, while the hydrophone 600 is in the transmit mode (602/610 connected by way of switch 612) of operation, only the PZT disc 112 for which the transducer PZT disc receives waveform 808 is being recorded, is electrically connected within the fetal heart rate transducer 100. The other PZT discs 112 are electrically disconnected.

In step 1308, a water phantom 706/708/710 is placed and coupled on both ends with the ultrasound coupling jelly 712 between the index plate 702 and the fetal heart rate transducer 100. The method then moves to step 1310.

In step 1310, a transducer PZT disc transmits phantom waveform 808 is recorded for each of the PZT discs 112, by way of the oscilloscope 812. The oscilloscope 812 is operationally connected to the hydrophone 600 that is in the receive mode (602/614 connected by way of switch 612), by placing a hydrophone PZT disc 604/606 that is operationally related to the hydrophone 600 into one of the PZT disc position hole 704 and recording one of the transducer PZT disc transmits phantom waveform 808 corresponding to one of the PZT disc 112 and repeating by moving the hydrophone PZT disc 604/606 to a different one of the PZT disc position hole 704 until at least one of the transducer PZT disc transmits phantom waveform 808 has been recorded at each of the PZT disc position hole 704. The method then moves to step 1312.

In step 1312 a determination is made if each of the transducer PZT discs transmit phantom waveform 808 is similar in amplitude 806, frequency 808, and repetition rate 810 through the first water phantom (one of 706/708/710) indicating uniform field strength and ultrasound beam field quality at height of the water phantom.

In an exemplary embodiment, the method of steps 1308, 1310, and 1312 can be repeated with different water phantoms 706, 708, or 710 having different heights 826, 816, and 818 respectively.

For disclosure purposes, the water phantoms 706, 708, and 710 are water-filled cylinders of a diameter 806 that is comparable to the diameter of the PZT discs 112 patterns when bonded to the bottom case 106. The heights 826, 816, and 818 of the water phantoms 706, 708, and 710 vary. In operation, passing ultrasound waves through a water phantom simulates passing ultrasound waves through the human body. In this regard, water phantoms allow methods that simulate the transducer 100 being used on patient 502 so that correct PZT disc 112/218 bonding and transducer operation can be quantitatively established through the use of a hydrophone 600, oscilloscope 812, and transducer 100/200.

Figure 27:
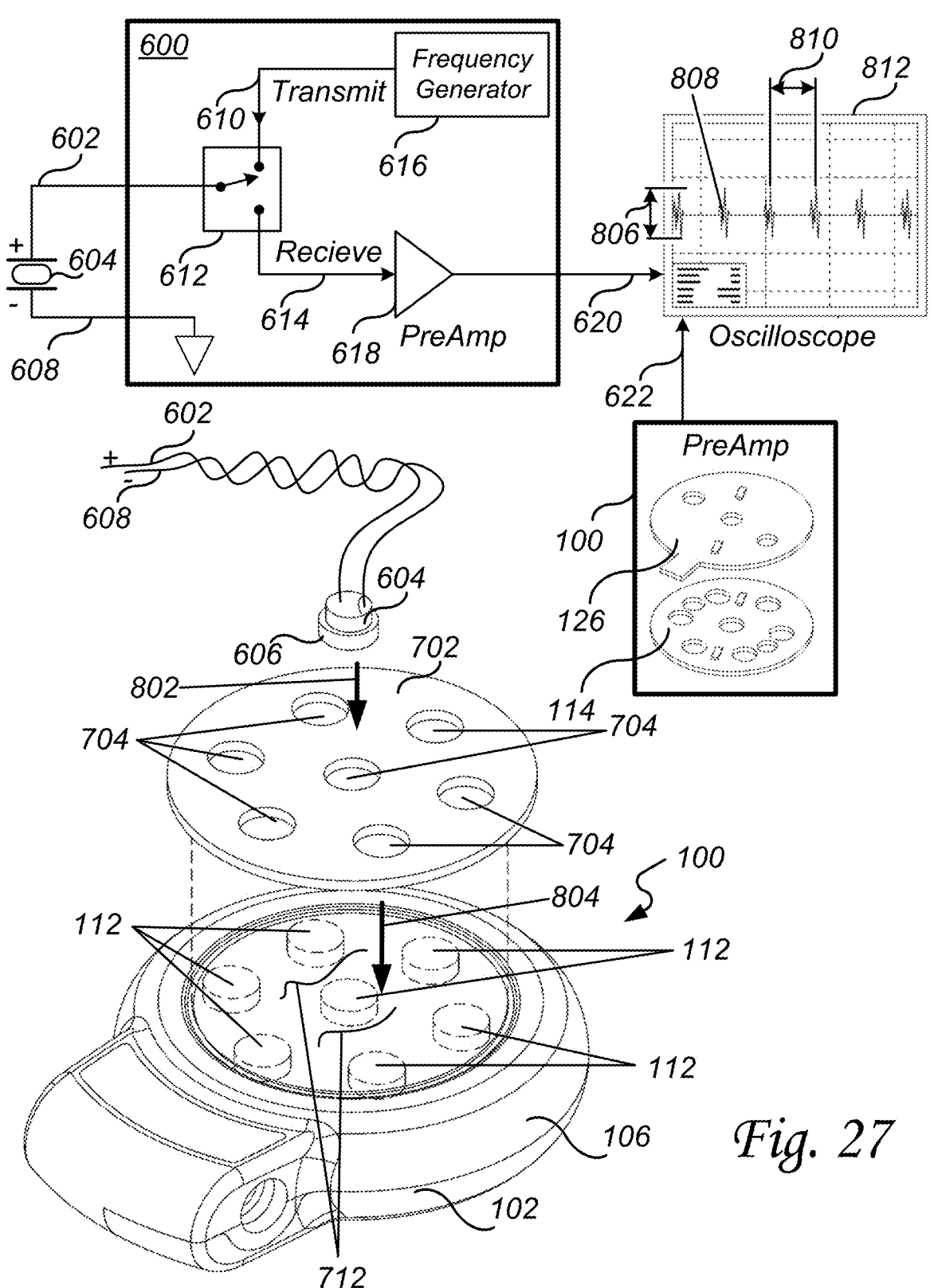
FIG. 27 illustrates one example of a hydrophone.

Referring to FIG. 27, there is illustrated one example of a hydrophone 600. In an exemplary embodiment, an index plate 702 can be fabricated from a 1 mm thick circular acrylic plate of 52.5 mm diameter, or other suitable size diameters with 7 holes of 12.4 mm to mimic the PZT disc 112 patterns of the transducer 100, forming PZT disc position hole 704. A PZT disc 604 can be bonded with the methods of the present invention to a plastic substrate 606 forming the hydrophone PZT disc 604/606. Electrically 602/608 wire leads can be connected to the hydrophone 600. The index plate 702 is coupled 804 to the bottom case 106 by way of ultrasound jelly 712 additionally the plastic substrate 606 when placed into one of the PZT disc position holes 704 is coupled with ultrasound jelly 712.

The hydrophone 600 comprises a frequency generator 616 that is matched to the transducer 100 center frequency of 1 MHZ+/−100 Hz and the pre-amp 618 is also identical to the pre-amp 622 from the transducer 100. The PZT disc 604 used in the hydrophone is also an exact match to the PZT disc 218 from the transducer 100. A toggle switch 612 enables the hydrophone 600 to be placed in a transmit mode of operation where 602 and 610 are connected together by way of switch 612 or a receive mode of operation where 602 and 614 are connected together by way of switch 612.

In the transmit mode of operation, the frequency generator 616 couples the generated frequency to the hydrophone PZT disc 604/606 which broadcast an ultrasound wave that can be detected by the PZT 112 disc with the target transducer 100. The ultrasound wave is received by one or more of the PZT disc 112. The PZT disc 112 is coupled to the frontend PCB 114 which is interconnected with the backend PCB 126. A preamp associated with the PCB 114/126 processes the ultrasound wave from the PZT disc 112 and the preamp output 622 is coupled to the oscilloscope 812 where the transducer PZT disc receives waveform 808 can be observed and recorded.

In a method of using the hydrophone 600, the top case 102 of the transducer 100 can be removed and a 6 to 8-inch long twisted pair cable can be connected to the output of the pre-amplifier 622 on the frontend PCB 114 or backend PCB 126 depending on where the pre-amplifier is located. The other end of the twisted pair cable 622 can be connected to the oscilloscope 812.

All but one of the PZT discs 112 can be disconnected by desoldering +V 194/294 electrode connection on the PZT disc 112 (−V 196/296 can stay connected). Additionally, the oscillator output can be disabled to turn off the transmission mode. The dismantled transducer 100 can be placed face-up on a leveled fixture. The index plate 702 can be coupled with ultrasound coupling jelly 712 to the face of the transducer 100 with the PZT disc position hole 704 aligned with the PZT disc 112. The hydrophone PZT disc 604/606 can be placed in the PZT disc position hole 704 corresponds to the PZT disc that is electrically connected, the plastic substrate 606 is coupled to the surface of the transducer 100 within the selected PZT disc position hole 704 with ultrasound coupling jelly 712.

The switch 612 is positioned in the transmit mode of operation, where 602/610 are connected together by way of the switch 612 and the transducer 100 is connected to power on the fetal monitor 302. The transducer PZT disc receive waveform 808 can then be displayed and recorded on the oscilloscope 812.

The method can be continued by electrically connecting one of the PZT discs 112, one at a time, moving the hydrophone PZT disc 604/606 to the corresponding PZT disc position hole 704, and recording the transducer PZT disc receive waveform 808 for each PZT disc 112 until all readings are complete.

All the readings can then be compared for identical amplitude 806, frequency 808, and repetition rate 810 to confirm the correct bonding of the PZT disc to the interior surface of the bottom case 106, as well as the transducer 100 correct receiving.

In the receive mode of operation, the hydrophone PZT disc 604/606 receives ultrasound waves generated by the PZT disc 112. The received ultrasound wave is coupled to a preamp 618 and the preamp 618 is coupled 620 to an oscilloscope 812.

In a method of using the hydrophone 600, a transducer 100 can be placed on a table with a proper fixture so that its face is up and perfectly leveled horizontally. The indexing plate 702 is coupled with ultrasound coupling jelly 712 to the face of transducer 100. The transducer 100 is connected to the fetal monitor and power is applied. Ultrasound coupling jelly 712 is applied to the plastic surface 606 of hydrophone 600 and placed in one of the PZT disc position holes 704. The toggle switch 612 is set to the receive mode and the pre-amp 618 output 620 transducer PZT disc transmit mode waveform 808 is displayed and recorded on the oscilloscope 812.

Transducer PZT disc transmit waveform 808 measurements can be made for all other positions of PZT discs 112 in the index plate 704 by placing the hydrophone PZT disc 604/606 in a different one of the respective indexing plate hole 704 and recording then verifying that all the seven waveform readings are identical having the same amplitude 806, frequency 808, and repetition rate 810.

Figure 28:
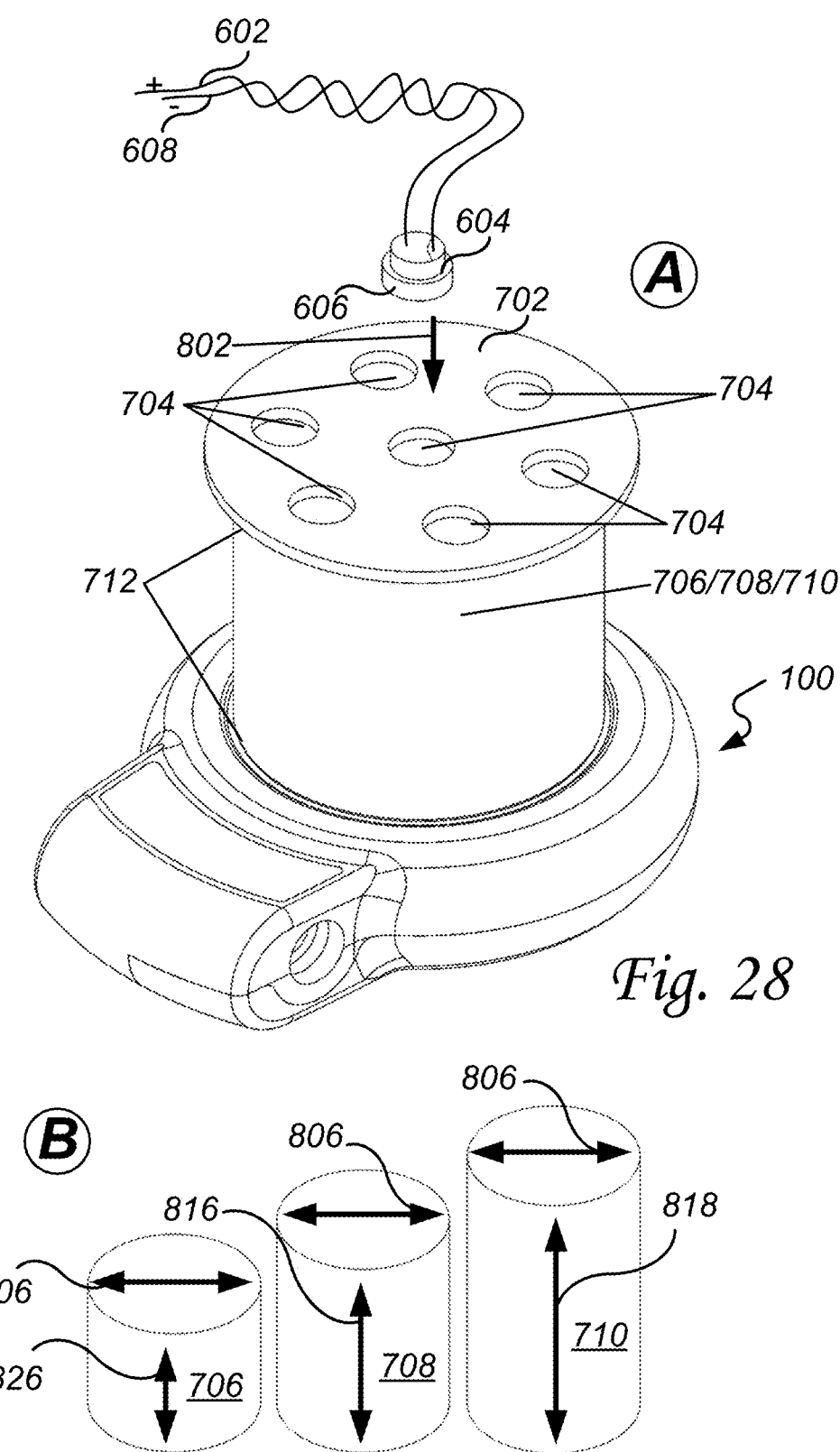
FIG. 28 illustrates one example of a hydrophone used in combination with a plurality of water phantoms.

Referring to FIG. 28, there is illustrated one example of a hydrophone used in combination with a plurality of water phantoms. In an exemplary embodiment, a quantitative test can be used to assess ultrasound beam quality, transmission, and reception characteristics of the PZT disc 112/218 as well as the bond integrity of the PZT disc and frontend PCB 114.

For disclosure purposes, the water phantoms 706, 708, and 710 are water-filled cylinders of a diameter 806 that is comparable to the diameter of the PZT discs 112 patterns when bonded to the bottom case 106. The heights 826, 816, and 818 of the water phantoms 706, 708, and 710 vary. In operation, passing ultrasound waves through a water phantom simulates passing ultrasound waves through the human body. In this regard, water phantoms allow methods that simulate the transducer 100 being used on patient 502 so that correct PZT disc bonding and transducer operation can be quantitatively established through the use of a hydrophone 600, oscilloscope 812, and transducer 100.

In operation, a cylindrical water phantom 706 of 52.5 mm diameter 806, and 35 mm in height 826 can be coupled with ultrasound coupling jelly on one end with the index plate 702 and the other end to the front surface of the transducer 100. The PZT disc position hole 704 is aligned with the PZT disc 112. The hydrophone PZT disc 604/606 is placed into one of the PZT disc position holes 704 and coupled with ultrasound coupling jelly 712 to the phantom 706.

The hydrophone 600 is placed in the receive mode of operation and the transducer PZT disc transmits through phantom waveform 808 corresponding to one of the PZT disc 112 is displayed on the oscilloscope 812 and recorded. The method can be repeated for each PZT disc 112 by moving the hydrophone PZT disc 604/606 to a different one of the PZT disc position hole 704 until at least one of the transducer PZT disc receives phantom waveform 808 has been recorded at each of the PZT disc position hole 704. A determination can then be made if each of the transducer PZT discs receives phantom waveform 808 is similar in amplitude 806, frequency 808, and repetition rate 810 indicating uniform field strength and ultrasound beam field quality at the height of the water phantom.

In an exemplary embodiment, in operation, only one of the transducer PZT disc 112 is connected for transmission at a time and the other PZT disc 112 is an open circuit by removing one of the wire leads when one of the water phantoms is used. When water phantom is not used, meaning the hydrophone PZT disc 604/606 is directly coupled onto the bottom case 102 plastic substrate to measure transmission from one of the PZT disc 112 then all other transducer PZT discs can be connected and continue transmitting as such transmissions do not interfere with results.

Measurements can be repeated for the phantoms with 85 mm height 816 and 150 mm height 818 to confirm the waveform measurements are identical on every transverse plane of the ultrasound beam path.

The functional performance of the transducer units 100/200 after bonding the PZT discs 112/218, 7 PZT discs 112, or 9PZT discs 218 can be carried out the same way.

Figure 29:
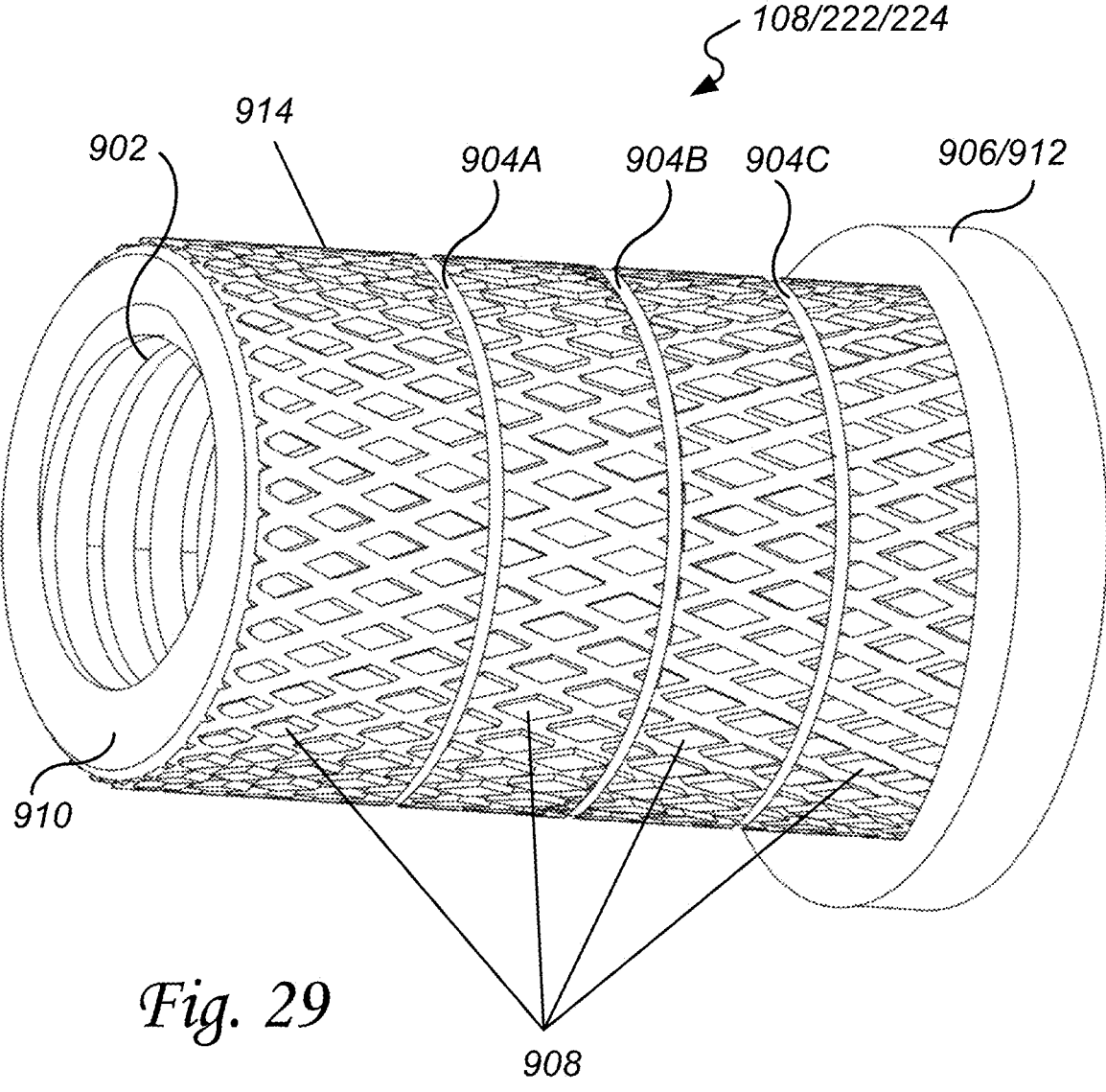
FIG. 29 illustrates one example of an insert.

Referring to FIG. 29, there is illustrated one example of a metal insert 108/222/224. In an exemplary embodiment, the metal insert 108/222/224 is cylindrical having an insert top end 910, an insert bottom end 912, and a cylindrical body 914. A diamond-shaped knurling 908 is present around the circumference of the body 914. A raised ridge 906 extends around the circumference of body 914 at the bottom end 912, and more than one groove 904A-C is spaced along and extends around the circumference of body 914. The metal insert 108/222/224 is molded into the standoff 110/228/230 with the bottom end 912 closest to the inside of the interior surface 156/234 plastic substrate and the top end 910 co-planar with the top of the standoff 110/228/230 in a manner to receive and fasten with the machine screw 134/210/214.

In an exemplary embodiment, the metal insert 108/222/224 can be made of brass, steel, or other suitable metals, as may be required and/or desired in a particular embodiment.

Referring to FIG. 30, there is illustrated one example of Doppler equations for frequency shift calculation.

Figure 31:
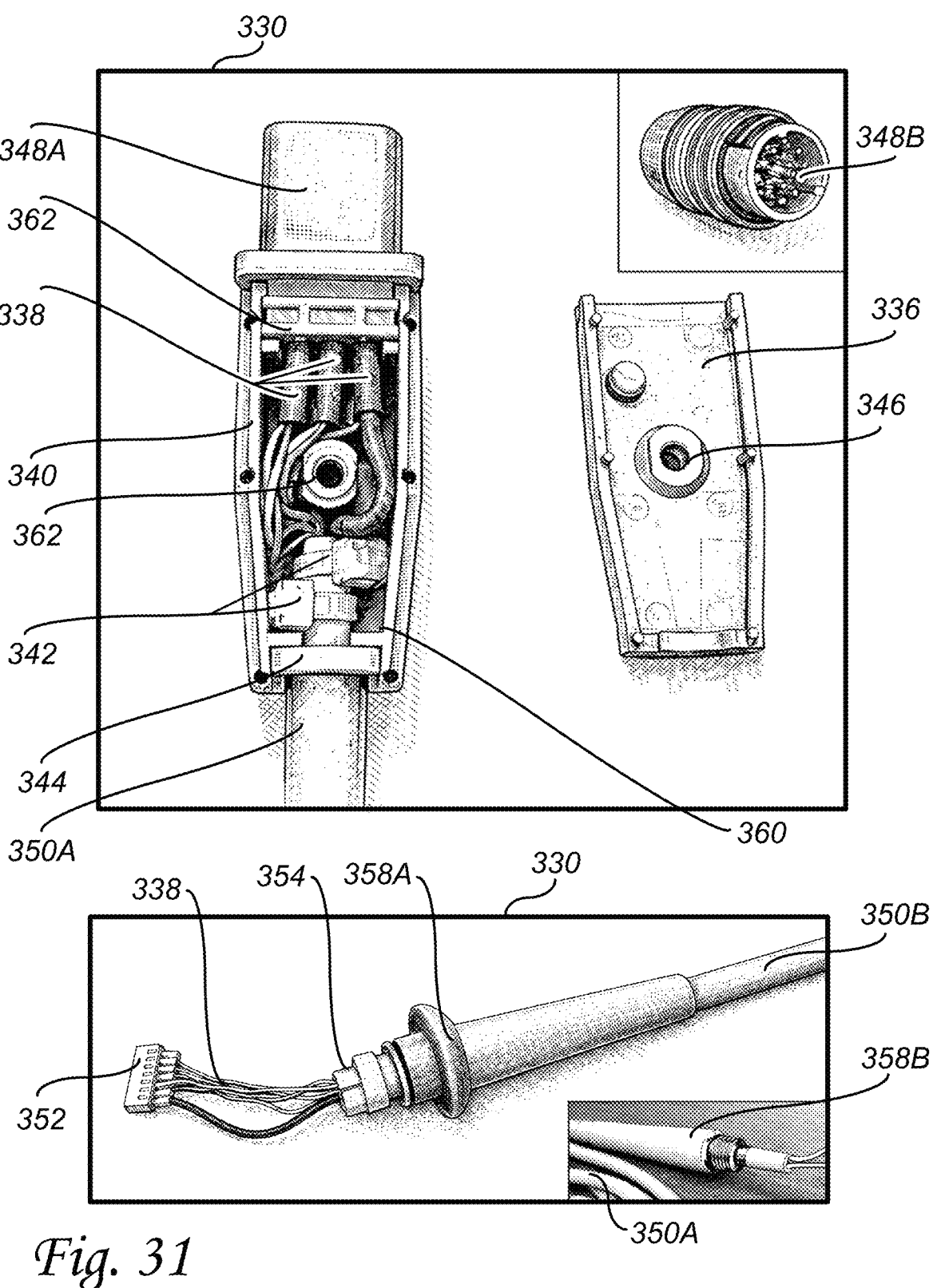
FIG. 31 illustrates one example of a cable assembly.

Referring to FIG. 31, there is illustrated one example of a cable 330 assembly. An advantage, in the present invention, is that, unlike prior cables that connect transducers 100 to fetal monitors 302 and notoriously fail where crimped and over-molded, the present invention, utilizes a fetal monitor end connector 348A/348B that has a hollow rigid body 340 made of plastic and a connector top 336 that can be fastened by way of the screw hole 346 and standoff 362 to the hollow rigid body 340. Additionally, a strain relief 344 made out of 60A shore hardness elastomer can be fitted into an integrally formed groove end 360 to secure cable 350 from pulling out of the hollow ridge body 340.

For disclosure purposes, fetal monitor end connectors 348A/348B are two different styles that interface to different models of fetal monitor 302. Other shaped types and kinds of fetal monitor end connectors 348 can be utilized as may be required and/or desired in a particular embodiment.

In an exemplary embodiment, the hollow rigid body 340 can be filled with silicon. In an alternative approach, the connector top 336 and standoff 362 can be eliminated and the hollow rigid body 340 can be filled and or otherwise sealed with silicon.

Additionally, the use of secondary strain relief 342 inside the hollow rigid body 340 further protects the cable 350 against pulling forces and relieves stress on the individual conductors 338 that are crimped/soldered on contact pins located at the wire connection end 362. In an exemplary embodiment, such secondary strain relief 342 can be at least two tie wraps or other suitable strain relief.

In an exemplary embodiment, electronic-grade silicone can be filled inside to make the connector compliant with IP68 specifications for water ingress. The increased length of the hollow rigid body 340 compared to the length of prior rubber over-molded approaches makes it easier for an operator to grab the hard-plastic connector for connecting and disconnecting from the fetal monitor 302.

In an exemplary embodiment, the transducer connector 352 terminates the individual conductors 338 on the opposite end of cable 350. The transducer connector 352 connects to the frontend PCB 114 or the backend PCB 126. Strain relief 354 and rubber boot 358 secure the cable 350 by way of the cable connector 104/140 entry hole/cavity inside the transducer 100.

In an exemplary embodiment, the improved fetal heart rate transducer 100 can comprise a cable 350 having a first cable end 350A and a second cable end 350B. A fetal monitor connector 348A/348B comprises a hollow rigid body 340 having a wire connection end 362 and an integrally formed grooved end 360. A strain relief 344 is placed over the first cable end 350A and secured within the integrally formed grooved end 360 holding the first cable end 350A from slipping out of the hollow rigid body 340.

In an exemplary embodiment, a secondary strain relief 342 can be fastened around the first cable end 350A within the hollow rigid body 340 proximate to the strain relief 360.

In an exemplary embodiment, such secondary strain relief 342 can be at least two tie wraps fastened in parallel around the first cable end 350A within the hollow rigid body 340 proximate to the strain relief 360.

The secondary strain relief 342 further prevents the first cable end 350A from being pulled out of the hollow rigid body 340. More than one conductor 338 from the first cable end 350A terminates with electrical connections at the wire connection end 362. The fetal monitor connector 348A/

348B plugs into a fetal monitor 302, and the second cable end 350B terminates with a transducer connector 352.

In an exemplary embodiment, an improved fetal heart rate transducer 100/200 comprises a top case 106/210A/210B, and a bottom case 106/204 that fastens to the top case 106/210A/210B, the bottom case 106/204 comprises an interior surface, the interior surface comprises de-embossed or raised more than one piezo-electric crystal (PZT) pad 138/232.

More than one PZT disc 112/218, each PZT disc 112/218 adheres to the PZT pad 138/232, a frontend printed circuit board (PCB) 114/216 is secured to the bottom case 106/204 and is operationally related to the PZT disc 112/218. A cable 330 has a first cable end 350A and a second cable end 350B. A fetal monitor connector 348A/348B comprises a hollow rigid body 340 having a wire connection end 362 and an integrally formed grooved end 360. A strain relief 344 is placed over the first cable end 350 and secured within the integrally formed grooved end 360 holding the first cable end 350A from slipping out of the hollow rigid body 340.

And, a secondary strain relief 342 is fastened around the first cable end 350A within the hollow rigid body 340 proximate to the strain relief 340. Wherein the secondary strain relief 342 further prevents the first cable end 350A from being pulled out of the hollow rigid body 340. More than one conductor 338 from the first cable end 350A terminates with electrical connections 338 at the wire connection end 362. Wherein the fetal monitor connector 348A/348B plugs into a fetal monitor 302, and the second cable end 350B terminates with a transducer connector 352, the transducer connector 352 connects to the frontend PCB 114/216.

In an exemplary embodiment, the secondary strain relief 342 can be at least two tie wraps that are fastened in parallel around the first cable end 350A within the hollow rigid body 340 proximate to the strain relief 340.

In an exemplary embodiment, the hollow rigid body 340 can be filled with silicon, and a connector top 336 can be fastened by way of the screw hole 346 and standoff 362 to seal fetal monitor connector 348A/348B including the hollow rigid body 340.

In an alternative approach, the connector top 336 and standoff 362 can be eliminated, and fetal monitor connector 348A/348B including the hollow rigid body 340 can be filled and or otherwise sealed with silicon.

Figure 32:
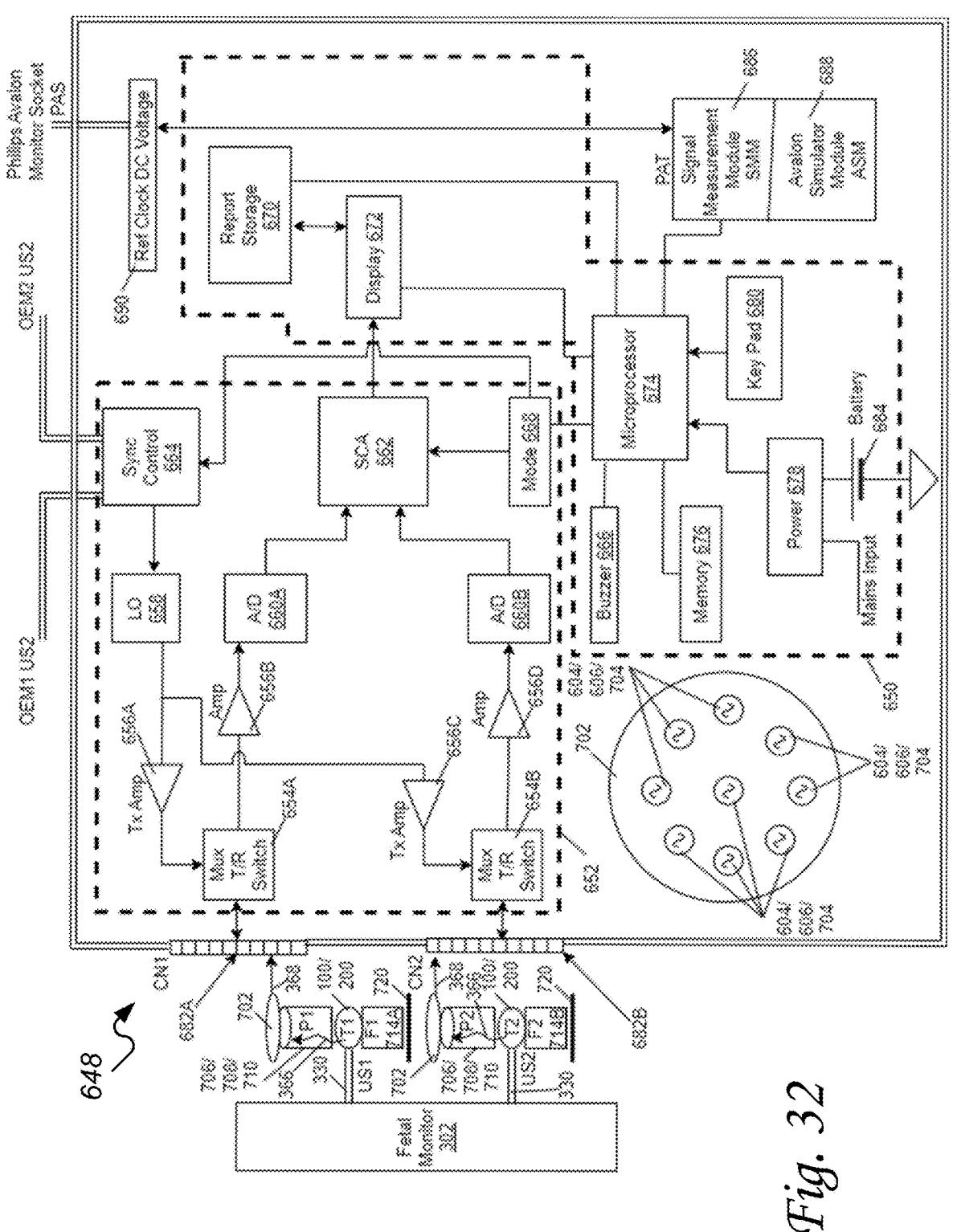
FIGS. 32-34 illustrate examples of an ultrasound beam quality test apparatus.

Referring to FIG. 32, there is illustrated one example of an ultrasound beam quality test apparatus 648. In an exemplary embodiment, the ultrasound beam quality test apparatus 648 can have two identical connectors CN1 682A and CN2 682B with 14 pins to connect to the hydrophone PZT discs 604. In an exemplary embodiment, the hydrophone PZT discs 604 can be permanently installed on the index plate 702 or on the top face of the acrylic water phantoms 706/708/710 of three different lengths. The top face of the acrylic water phantoms 706/708/710 is configured as an index plate 702. The hydrophone PZT discs are preferably bonded to the index plate 702 using the ultra-slow cure bonding process on the present invention. The hydrophone PZT discs 604 are positioned on the index plate 702 in positions that correspond to the locations of the transducer PZT discs 112/218 such that the phantom 706/708/710 and index plate 702 can be aligned when positioned on the fetal heart rate transducer 100/200 such that there is a one-to-one correspondence between one of the hydrophone discs 604 and one of the transducer PZT discs 112/218 so that each transducer PZT disc 112/218 can be independently tested.

In an exemplary embodiment, the index plate 702 can be integrally formed on the surface of the phantom 706/708/710 allowing each of the hydrophone PZT discs 604 to be adhered to the surface of the phantom 706/708/710. The PZT disc bonding techniques of the present invention can be utilized to adhere the hydrophone PZT disc 604 to the integrally formed index plate 702 on the surface of the phantom 706/708/710.

The two CN1 682A and CN2 682B connector in combination with the rest of the beam control circuit 652 allows two fetal heart rate transducers 100/200 to be independently tested at the same time. The two CN1 682A and CN2 682B connectors pass on the electrical signal picked up from the individual hydrophone PZT discs 604 based on the strength of the transducer PZT disc waveform 366 after passing through the phantom 706/708/710. The received transducer PZT disc waveform 368 is received at the multiplexer/transmit-receiver switch (MUX T/R SW) 654A or 654B that selectively processes the signal through the fixed gain amplifiers 656B or 656D followed by Analog to Digital conversion 660A or 660B and stored/captured in signature comparison/analyzer (SCA) 662.

During the production phase of the ultrasound beam quality test apparatus 648, a working OEM-certified fetal heart rate transducer can be used as a reference fetal heart rate transducer by initially connecting it to the CN1 682A connector to acquire reference signal signatures and store the reference signal signatures in the SCA 662 to be used as a reference comparison when testing other fetal heart rate transducers 100/200. The reference base signal signatures can be properly memory tagged with the fetal heart rate transducer's make, model, ultrasound beam quality test apparatus location, phantom length identifier, and other information as may be required and/or desired in a particular embodiment. This process in effect creates a library of reference signal signatures for each kind of fetal heart rate transducer 100/200, each type of phantom 706/708/710 used with the fetal heart rate transducer 100/200, and other relevant test conditions.

The process is repeated using the same reference fetal heart rate transducer 100/200 connected to the CN2 connector 682B. The reference signal signatures captured on channel CN2 682B are compared with the reference signal signatures captured on channel CN1 682A to ensure that both the channels (CN1 682A, CN2 682B) have identical results and either one set of the reference signal signatures (SS) is stored as the default learned/standard signal/reference signature pattern inside the SCA 662. The process can be repeated for various make and models of fetal heart rate transducers 100/200 and the reference signal signatures recorded.

In an exemplary embodiment, in operation, at a hospital for example whenever there is a fetal heart rate transducer tracing in doubt/confusion for spurious fetal heart rate readings, discontinuity or interference on the fetal heart rate tracing, adverse events involving injury/complications/death has occurred or simply the transducer needs to be tested for the ultrasound beam quality as a routine preventive maintenance, the fetal heart rate transducer 100/200 can be connected to the ultrasound beam quality test apparatus.

In this regard, the fetal heart rate transducer 100/200 is prepared for testing by connecting the fetal heart rate transducer 100/200 to the fetal monitor 302, placing the fetal heart rate transducer 100/200 on a steady fixture support F1 714A or F2 714B, horizontally leveling the transducer 100/200 face pointing upward, applying coupling jelly 712 to the surface of the transducer 100/200, placing one of the phantoms 706, 708, or 710 (P1 or P2) with lengths of 816, 818, or 826 on the transducer 100/200 face, aligning the hydrophone PZT discs 604 with the transducer PZT discs 112/218 by rotating the phantom 706/708/710 or index plate 702, connecting the hydrophone PZT discs 604 to either of connector CN1 682A or CN2 682B, and selecting the specific model of transducer in test protocol, enter the serial number of the transducer using the keypad 680 and check that the display 372 shows accurate values with date and time stamps, unique system generated test ID and location/site details.

In an exemplary embodiment, testing begins when the test run key is pressed, a set of signal signatures are captured, and the menu-driven protocol can prompt the user to replace the phantom assembly (P1 or P2) with a different length 816/818/826 phantom 706/708/710. The user can then be prompted to confirm the placement of the phantom 706/708/710 and press test run. The signal signatures are captured for the second phantom. The user is then prompted to place a third phantom 706/708/710 assembly of different lengths 816/818/826. The test resumes and a third set of signal signatures is captured. The ultrasound beam quality report can then be generated showing a hydrophone map with marking that indicate which transducer PZT discs 112/218 locations inside the transducer 100/200 head have faults that caused ultrasound beam deterioration and/or spurious fetal heart rate readings. The ultrasound beam quality report can also indicate the percentage deviation of signal amplitude compared to the learned/stored standard signal signature hydrophone location-wise. The learned/stored reference signal signature can also be referred to as a predetermined reference signal signature. The ultrasound beam quality report can be stored by the computer system 650 in a manner that cannot be modified but is available for retrieval and printing or sharing through serial/USB port, or other suitable methods.

The software program can allow the user to run the test for two units of the same model of fetal ultrasound transducer at the same time by connecting to CN1 682A and CN2 682B connectors and running the preset test protocol. Reports can be generated as a standard using factory default predetermined reference signal signature comparison as well as a comparison between the signal signatures obtained from both the fetal heart rate transducers 100/200 by assigning one of them as a reference transducer unit in the test protocol set up.

The aforementioned testing process can be used for all makes and models of fetal heart ultrasound transducers using model-specified phantom 706/708/710 assemblies of three specified lengths 816/818/826. In the case of Philips Avalon fetal ultrasound transducer models M2736A, M2736AA, and Ref #867246, additional tests can be performed using an LVDS input fault test protocol. In this regard, a phantom 706/708/710 assembly with length 816/818/826 is placed properly on the transducer 100/200 face and connected to CN1 682A or CN2 682B the test can begin. During this test, all the 7 inputs to MUX T/R SW 654A or 654B are connected to the fixed gain amplifier 656B or 656D, and the signal is monitored inside SCA 662 for the expected transmit—receive pattern. If there is a permanent open circuit of one of the LVDS inputs inside the transducer 100/200, there will not be any transmission of the ultrasound beam and the buzzer 666 will continuously sound indicating that either transducer cable 350 or Main CPU (Backend PCB) board is faulty.

If an open circuit is not detected then the test continues by prompting the users to flex the cables to determine if there are any intermittent shorts or open connections. In this regard, the user starts carefully flexing the cable near the connector end on fetal monitor 302 and slowly moves towards the strain relief end of the transducer head 100/200 without causing mechanical disturbance to the transducer head. Should an open wire connection be detected whether temporary or continuous the buzzer 666 will sound and an LVDS fault will be reported on the display 672. The user can continue flexing the cable to re-confirm the intermittent break and terminate the test whenever satisfied. The report will tell how long the LVDS fault test lasted and at what time intervals the fault occurred while the user manually flexed the cable.

In an exemplary embodiment, when the test is performed on a fetal transducer to acquire signal signatures in proportion to ultrasound beam intensity, as sensed by each hydrophone PZT disc 606 using the phantom 706/708/710 assembly, the MUX T/R SW 654A or 654B turns on each input line switch for about 650 micro-seconds in sequence. That means the actual time taken to acquire a set of 7 signal signatures using a single phantom 706/708/710 for a Philips Avalon transducer 100/200 with 7 PZT discs 112/218, would take 4550 micro-seconds or 0.455 milliseconds. This signal signature acquisition time can be reduced if the MUX T/R SW 654A or 654B switching is synchronized with the transmission waveform obtained from the fetal monitor's second (free) ultrasound transducer socket by connecting to the appropriate plug OEM1 US2/OEM2 US2 and using the sync control 664 and local oscillator (LO) 658 for the transducers models that do not contain any active signal processing circuit inside the head assembly. Such transducer models (e.g. GE Corometrics NAUTILUS 5700LAX/HAX series) would take about 15 to 20 minutes to complete the full testing with 3 sets of signal signature acquisitions with three different phantoms 706/708/710 assemblies. If both channels are used at a time, about 40 to 50 transducer units can be tested in an eight-hour period. Transducers with LVDS amp circuits such as Philips Avalon models M2736A, M2736AA and Ref #867246, about 15 to 30 transducer units can be tested in eight hours as LVDS input fault test with manual cable flexing would require an additional 5 to 15 minutes.

In an exemplary embodiment, once a fetal heart rate transducer 100/200 is confirmed to be faulty by the present invention testing methods it can be sent physically intact, without the need to open the head assembly, to an accredited lab for the second confirmatory testing if that particular unit is associated with adverse event of injury/complications/stillbirth or death.

In an exemplary embodiment, the ultrasound beam quality test apparatus for ultrasound beam transmission quality assessment of fetal heart rate transducer can be configured to have the capability to set the mode 668 as transmitter so that the local oscillator LO 658 output can be set for ultrasound transducer OEM model-specific frequency and amplitude voltage to be applied to all the hydrophone PZT discs 604 through TX Amplifier buffer 656A or 656C in order to make the hydrophone assembly continuously transmit the transducer PZT disc waveform 366 to OEM specifications. This transmission mode 668 feature is useful to troubleshoot the OEM transducer performance in ultrasound beam reception mode in case of failure to detect the received Doppler signal and hence useful as a service tool. This transmission mode selection feature is useful to troubleshoot the fetal heart rate transducer performance in ultrasound beam reception mode in case of failure to detect the received Doppler signal, spurious signal or artifact pick up with error in FHR readings due to autocorrelation FHR detection algorithm firmware/software mechanism failure, permanent or intermittent fault in signal processing circuit and hence useful as a versatile service tool.

In an exemplary embodiment, the ultrasound beam quality test apparatus can also have a specific 8-pin receptacle socket labeled PAS to directly connect with the red colored 8-pin transducer socket labeled 'Fetal Sensors' on Philips Avalon series fetal monitor models FM20/FM30/FM40/FM50 and check DC supply voltage as well as all other IN-OUT signals from the fetal monitor to transducer in order to quickly determine if the fetal monitor is faulty or a particular socket on the fetal monitor is faulty after measurements are carried out by connecting PAS to all the fetal monitor sockets one by one. Internal to the ultrasound beam quality test apparatus, the PAS socket is connected to the circuit block labeled as Reference clock DC Voltage 690 and Philips Avalon monitor tester (PAT). The PAT tester comprises two individual functional blocks, Signal Measurement Module (SMM) 686 to assess all the electrical signal parameters such as voltage, frequency, signal stability, and Avalon Simulator Module (ASM) 688 which acts as a patient simulator to outputs FHR, FHR Doppler Signal Level, Toco contraction waveform, Intra Uterine Pressure (IUP) waveform, Maternal ECG (MECG), Maternal Pulse (MP), Fetal ECG (FECG) through a CAN controller by way of simulation test cycle default or manually selectable program. The Avalon simulator module 688 can act as a maternal/fetal patient parameter simulator and will help to test the Philips Avalon fetal monitors independent of fetal transducers for all the monitoring functions such as low/high FHR alarm, Doppler signal level, MHR to FHR/FHR1 to FHR2 coincidence detection, etc. Before the Avalon fetal monitor simulation testing is started, the test protocol software can generate Pseudo transducer serial numbers for testing and recording on the strip chart paper of the fetal monitor to replicate the real-life patient fetal/CTG tracing for extended hours' monitoring event in order to confirm that all the parameters, FHR, Toco contraction waveform profile (amplitude/frequency), IUP, MP, MECG/FECG waveform etc., are accurately captured on the fetal monitor display as well as the strip chart recorder without any unwanted signal interference or the 'artifacts'.

In an exemplary embodiment, an ultrasound beam quality test apparatus 648 for testing fetal heart rate transducers 100/200 can comprise a phantom 706/708/710, a fetal monitor 302, and a computer system 650. The computer system 650 comprises a microprocessor 674, a memory 676, and a beam control circuit 652. The microprocessor 674 is operationally related to the memory 676, and the beam control circuit 652. The beam control circuit 652 comprises at least one of a multiplexer 654A and/or 654B, and a signal comparison and analyzer (SCA) 662.

The ultrasound beam quality test apparatus 648 further comprises a fetal heart rate transducer 100/200. The fetal heart rate transducer 100/200 comprises more than one transducer piezo-electric crystal (PZT) disc 112/218. The fetal heart rate transducer 100/200 is electrically interconnected with the fetal monitor 302 which causes each of the transducer PZT discs 112/218 to generate a transducer PZT disc waveform 366.

The ultrasound beam quality test apparatus 648 further comprises an index plate 702. The index plate 702 comprises more than one of a hydrophone PZT disc 604. In some embodiments, the index plate 702 can be integrally formed on the top surface of the phantom 706/708/710. Phantom 706/708/710 can be placed between the fetal heart rate transducer 100/200 and the index plate 702, and each of the hydrophone PZT disc 604 can adhere to the index plate 702 in positions that align with and correspond to the locations of each of the transducer PZT disc 112/218 within the fetal heart rate transducer 100/200. Each of the hydrophone PZT disc 604 can be electrically interconnected with the beam control circuit 652.

In operation, the memory 676 can be encoded with instructions that when executed by the microprocessor 674 perform the steps of placing the multiplexer 654A and/or 654B in receive mode for one of the hydrophone PZT disc 604 and electrically disconnecting the other of the hydrophone PZT disc 604. At the signal comparison and analyzer SCA 662, a received transducer PZT disc waveform 368 is received from the selected one of the hydrophone PZT disc 604. The received transducer PZT disc waveform 368 is the transducer PZT disc waveform 366 from the transducer PZT disc 112/218 that is positioned directly opposite the selected one of the hydrophone PZT disc 604 after passing through the phantom 706/708/710.

In an exemplary embodiment, it is possible to configure the ultrasound beam quality test apparatus to acquire signal signatures simultaneously from all the hydrophone PZT discs by implementing multiple channels of fixed gain amplifier with dedicated A/D converter at its output and configuring the test software instruction protocol in the memory.

Processing then continues by generating, by way of the signal comparison and analyzer 662, a signal signature based on the received transducer PZT disc waveform 368, and recording, at the computer system 650, the signal signature for the selected one of the hydrophone PZT disc 604, wherein the selected one of the hydrophone PZT disc 604 corresponds to one of the transducer PZT disc 112/218.

Processing then continues by returning to the step of placing the multiplexer 654A and/or 654B in receive mode, and selecting a different one of the hydrophone PZT disc 604 until the signal signature has been recorded for each of the hydrophone PZT disc 604.

Processing continues by generating, by way of the computer system 650, an ultrasound beam quality report, wherein the ultrasound beam quality report compares one or more of a predetermined reference signal signature with the signal signature recorded for each one of the hydrophone PZT disc 604 to determine ultrasound beam quality of the fetal heart rate transducer 100/200, wherein each one of the hydrophone PZT disc 604 corresponds to one of the transducer PZT disc 112/218.

For disclosure purposes, the predetermined reference signal signatures are signal signatures captured from a known good transducer 100/200, factory configured reference signal signatures, a known good transducer 100/200 tested side-by-side with a test transducer 100/200 (i.e. one plugged into CN1 682A and one plugged into CN2 682B) or otherwise normal/anticipated signal signatures that can be used as comparison to test recorded signal signatures to determine if the transducer PZT discs 112/218 under test are operating correctly.

In this regard, in an exemplary embodiment, the ultrasound beam quality test apparatus 648 can comprise a second phantom 706/708/710, and a second fetal heart rate transducer 100/200. The second fetal heart rate transducer 100/200 can comprise more than one of a second transducer piezo-electric crystal (PZT) disc 112/218. The second fetal heart rate transducer 100/200 can be electrically interconnected with the fetal monitor 302 which causes each of the second transducer PZT discs 112/218 to generate a second transducer PZT disc waveform 366.

The ultrasound beam quality test apparatus 648 can comprise a second index plate 702. The second index plate 702 can comprise more than one of a second hydrophone PZT disc 604. The second phantom 706/708/710 can be placed between the second fetal heart rate transducer 100/200 and the second index plate 702. Each of the second hydrophone PZT disc 604 can be adhered to the second index plate 702, by the methods of the present invention, in positions that align with and correspond to locations of each of the second transducer PZT disc 112/218 within the second fetal heart rate transducer 100/200, each of the second hydrophone PZT disc is electrically interconnected with the beam control circuit.

The beam control circuit 652 can comprise a second multiplexer 654B. The microprocessor is operationally related to the second multiplexer 654B. The memory 676 can be encoded with instructions that when executed by the microprocessor 674 perform the steps of placing the second multiplexer 654B in receive mode, in a mutually exclusive manner from the (first) multiplexer 654A, for one of the second hydrophone PZT disc 604 and electrically disconnecting other of the second hydrophone PZT disc 604.

Processing then continues by receiving at the signal comparison and analyzer 662, from the selected one of the second hydrophone PZT disc 604, a second received transducer PZT disc waveform 368. The second received transducer PZT disc waveform 368 is the second transducer PZT disc waveform 366 from the second transducer PZT disc 112/218 that is positioned directly opposite selected one of the second hydrophone PZT disc 604 after passing through the second phantom 706/708/710.

Processing then continues by generating, by way of the signal comparison and analyzer 662 a second signal signature based on the second received transducer PZT disc waveform 368, and recording, at the computer system 650, the second signal signature for the selected one of the second hydrophone PZT disc 604, wherein the selected one of the second hydrophone PZT disc 604 corresponds to one of the second transducer PZT disc 112/218.

Processing then continues by returning to the step of placing the second multiplexer 654B in receive mode and selecting a different one of the second hydrophone PZT disc 604 until the second signal signature has been recorded for each of the second hydrophone PZT disc 604.

Processing then continues by generating, by way of the computer system 650, a second ultrasound beam quality report, wherein the second ultrasound beam quality report compares one or more of the predetermined reference signal signatures with the second signal signature recorded for each one of the second hydrophone PZT disc 604 to determine the ultrasound beam quality of the second fetal heart rate transducer 100/200, wherein each one of the second hydrophone PZT disc 604 corresponds to one of the second transducer PZT disc 112/218.

In operation, the fetal heart rate transducer 100/200 and the second fetal heart rate transducer 100/200 can be simultaneously tested for the ultrasound beam quality, in a mutually exclusive manner, using a single ultrasound beam quality test apparatus.

In an exemplary embodiment, an ultrasound coupling jelly 712, better illustrated in at least FIGS. 27 and 28, can be used to ultrasonically couple the index plate 702 to the phantom 706/708/710 and the surface of the fetal heart rate transducer 100/200 to the phantom 706/708/710.

In an exemplary embodiment, each of the hydrophone PZT discs 604 can have a top side and an epoxy side. Each of the hydrophone PZT discs 604 can be adhered to the index plate 702 as follows:

cleaning the surface and the index plate 702;

mixing and degassing in a vacuum, for a first degas time period, an ultra slow-cure epoxy;

depositing a drop of the ultra slow-cure epoxy in the center of the epoxy side of each of the hydrophone PZT discs 604 while the hydrophone PZT discs 604 are resting on a horizontal surface with the epoxy side up, or on the index plate 702 while the index plate 702 is resting on a horizontal surface;

allowing the drop to self-level for a first self-leveling time period;

placing the epoxy side of each of the hydrophone PZT discs 604 on the index plate 702 at the predetermined locations while the index plate 702 is resting on a horizontal surface; and allowing the hydrophone PZT discs 604 and the index plate 702 assembly to cure for a first cure time period.

In an exemplary embodiment, the first degas time period can be 15 to 20 minutes, the first self-leveling time period can be 15 to 20 minutes, the first cure time period can be a minimum of 68 hours, the ultra slow-cure epoxy can be mixed as four parts resin to one part hardener, and the size of the drop can be in the range of 0.2 ml.

In an exemplary embodiment, the received transducer PZT disc waveform 368 from selected one of the hydrophone PZT disc 604 can be converted from analog-to-digital representation of the received transducer PZT disc waveform 368 prior to reaching the signal comparison and analyzer 662 by way of analog-to-digital converter 660A or 660B.

Figure 33:
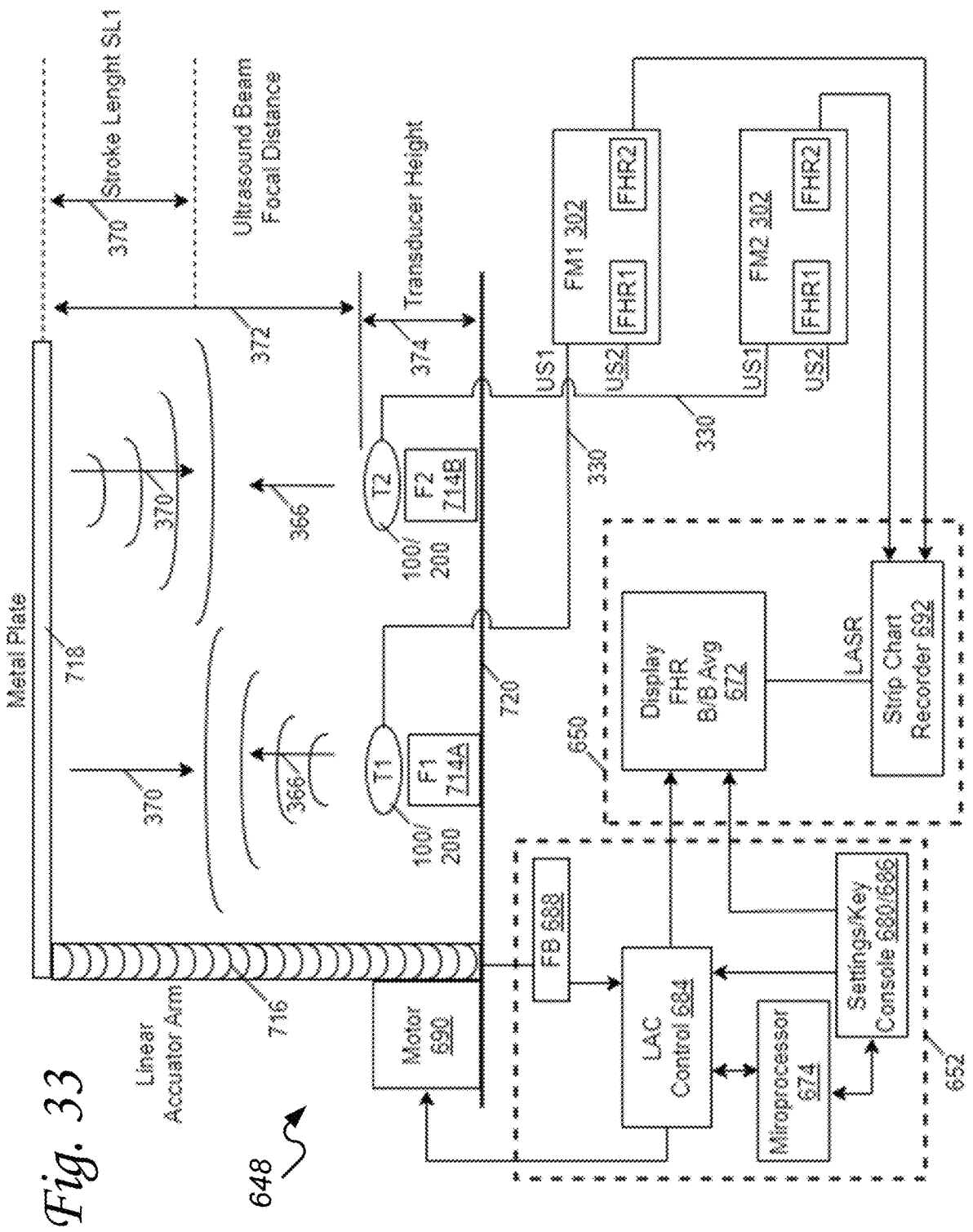

Referring to FIG. 33, there is illustrated one example of an ultrasound beam quality test apparatus. In an exemplary embodiment, a linear actuator 716 has a vertical rack with a horizontal metal plate 718 attached to the top end. The vertical rack can be driven by a motor 690 or other suitable actuator mechanism to move the metal plate 718 up and down with programmable travel stroke length 370 and programmable speed which is equal to the time it takes to travel distance of full stroke length 370. The metal plate 718 can be either rectangular or circular with a sufficiently large area to cover the transmitting surface of at least two fetal heart rate transducers 100/200 (T1, T2) that are horizontally on raised platforms (F1 714A and/or F2 714B) whose heights can be adjusted to make sure that movement of the metal plate 718 is within the ultrasound beam focus range 372 specified for the corresponding transducer 100/200 model. The transducers 100/200 T1 and T2 can be of the same or different models and connected to either the same fetal monitor 302 or independently to two different fetal monitor 302 from either the same manufacturer or two different manufacturers depending on the test result comparison desired. The linear actuator 716 has a setting console 686, that can be operationally related to microprocessor 674, where either programmed test cycle protocols can be recalled or manually programmed as fetal heart rate variations with respect to time as a beat-to-beat measurement mode or averaged mode and that is displayed on linear actuator display 672 as well as recorded on strip chart recorder LASR 692. The linear actuator controller (LAC) 684 drives the motor 690 as well as processes the vertical arm movement feedback 688 from an optical encoder or any suitable feedback (FB) 688 control circuit implementation to ensure the actual arm/metal plate 718 movement with stroke length 370 per unit time is as per the fetal heart rate setting cycle. In other words, the up-down movement of the metal plate 718 with respect to time simulates the fetal heart beating motion with set fetal heart rate values.

In an exemplary embodiment, for example, and not a limitation, one or two transducers T1 and T2 100/200 of the same model can be connected to a single fetal monitor FM1 302 or different FM2 302. The test cycle can be started, by way of the linear actuator, moving the metal plate 718 up and down corresponding to a selected simulated fetal heartbeats per minute such as the lowest fetal heart rate, such as 40 to 60 beats per minute (bpm) (depending on OEM specifications). The motion of the metal plate 718 can remain constant for 30 seconds or other desired time intervals and then the selected simulated fetal heartbeats per minute can be increased or otherwise changed in preset steps, such as 5, 10, 15, 20, or other bpm increments, and tested. This can repeat every 30 seconds or other desired time intervals until the maximum OEM-specified measurement fetal heart rate value is reached which is generally around 240 bpm though the transducer 100/200 can be simulated tested to around 350 bpm for accuracy.

Readings between the selected simulated fetal heartbeats per minute desired and the fetal heart rate readings recorded on the fetal monitor(s) 302 for each of the transducers 100/200 can be compared. Ideally, the selected simulated fetal heartbeats per minute and the fetal heart recorded by each of the transducers 100/200 should match very closely within +/−2 bpm with the selected simulated fetal heartbeats per minute.

A reference transducer 100/200 such as a brand new or certified transducer 100/200 from the OEM factory or other known good transducer 100/200 can be used to calibrate and/or verify correct simulated fetal heartbeats per minute metal plate 718 motion and ultrasound beam quality test apparatus operation.

In an exemplary embodiment, to test the used/old transducers 100/200, a reference transducer 100/200 T1 can be connected to a fetal monitor FM1 302 socket US1, and a used/old transducer 100/200 T2 connected to a fetal monitor FM2 302 US1 and the above reference protocol or a variation thereof executed. If the readings from the old/used transducer 100/200 don't match closely within +/−2 bpm with the selected simulated fetal heartbeats per minute, as well as the reference transducer 100/200 or behave sporadically, it means the used/old transducer T2 100/200 has problem with the autocorrelation detection block hardware and software and that would be the case with Philips Avalon fetal monitors as the ultrasound transducer's head has the complete analog and digital signal processing circuit block incorporated with microcontroller unit (MCU).

More vigorous repeat checks/tests can be performed with specific selected simulated fetal heartbeats per minute settings on the linear actuator set up for a longer test cycle time period once a transducer 100/200 or a fetal monitor 302 is found to have sporadic error issues with the autocorrelation fetal heart rate detection.

In an exemplary embodiment, the varying DC voltage signals corresponding to the fetal heart rate from transduce T1 100/200, the fetal heart rate from transduce T2 100/200, and from both the fetal monitors FM1 and FM2 302 can be fed to multi-channel strip chart recorder LASR 692 for easier facilitation of comparison between the selected simulated fetal heartbeats per minute and actual fetal heart rate values obtained from the fetal monitor/transducer(s) 100/200 under test and as a permanent test record report.

In an exemplary embodiment, an ultrasound beam quality test apparatus 648 for testing fetal heart rate transducers 100/200 can comprise a fetal monitor 302 and a computer 650. The computer system 650 can comprise a microprocessor 674, a memory 676, and a linear actuator controller 684. The microprocessor 674 is operationally related to the memory 676 and linear actuator controller 684.

The ultrasound beam quality test apparatus 648 can further comprise a fetal heart rate transducer 100/200. The fetal heart rate transducer 100/200 comprises more than one transducer piezo-electric crystal (PZT) disc 112/218. The fetal heart rate transducer 100/200 can be electrically interconnected with the fetal monitor 302 which causes each of the transducer PZT discs 112/218 to generate a transducer PZT disc waveform 366.

The ultrasound beam quality test apparatus 648 can further comprise a linear actuator 716. The linear actuator 716 comprises a metal plate 718. The metal plate 718 is movably attached to the linear actuator 716 and is vertically adjustable by way of the linear actuator 716. The metal plate extends across the top surface of the fetal heart rate transducer 100/200.

A linear actuator controller 684 is operationally related to the microprocessor 674 and operates the linear actuator 716. The microprocessor is operationally related to the linear actuator controller 684. The memory is encoded with instructions that when executed by the microprocessor 674 perform the steps of setting the height of the metal plate 718 to an ultrasound beam focal distance 372, by way of the linear actuator 716, wherein the top surface of the fetal heart rate transducer 100/200 and the metal plate 718 are opposed with only an air gap therebetween.

Processing then continues by oscillating along a stroke length 370, by way of the linear actuator 716, the metal plate 718 between closer to and further from the top surface of the fetal heart rate transducer 100/200 to generate a selected simulated fetal heartbeats per minute, wherein the transducer PZT disc waveform 366 is reflected off of the metal plate 718 and received Doppler shifted at the transducer PZT disc 112/218.

Processing then continues by determining, by way of the fetal monitor 302, if the fetal heart rate transducer 110/200 is recording a fetal heart rate that is substantially the same as the selected simulated fetal heartbeats per minute.

In an exemplary embodiment, memory 676 can be encoded with instructions that when executed by the microprocessor 674 perform the step of changing the selected simulated fetal heartbeats per minute and returning to the step of oscillating until the fetal heart rate transducer 100/200 has been tested in incremental step amounts of the selected simulated fetal heartbeats per minute between a minimum simulated fetal heartbeats per minute and a maximum simulated fetal heartbeats per minute.

In an exemplary embodiment, each of the selected simulated fetal heartbeats per minute is tested for at least 30 seconds, the minimum simulated fetal heartbeat is in range of 40 heartbeats per minute to 60 heartbeats per minute, and the maximum simulated fetal heartbeat is in range of 240 heartbeats per minute though the transducer 100/200 can be simulated tested to around 350 bpm for accuracy.

In an exemplary embodiment, the ultrasound beam quality test apparatus 648 can further comprise a raised platform 714A and/or 714B that is also mechanically stable. The fetal heart rate transducer 100/200 can be placed on the raised platform 714A/714B that is mechanically stable during simulated fetal heartbeats per minute testing.

Figure 34:
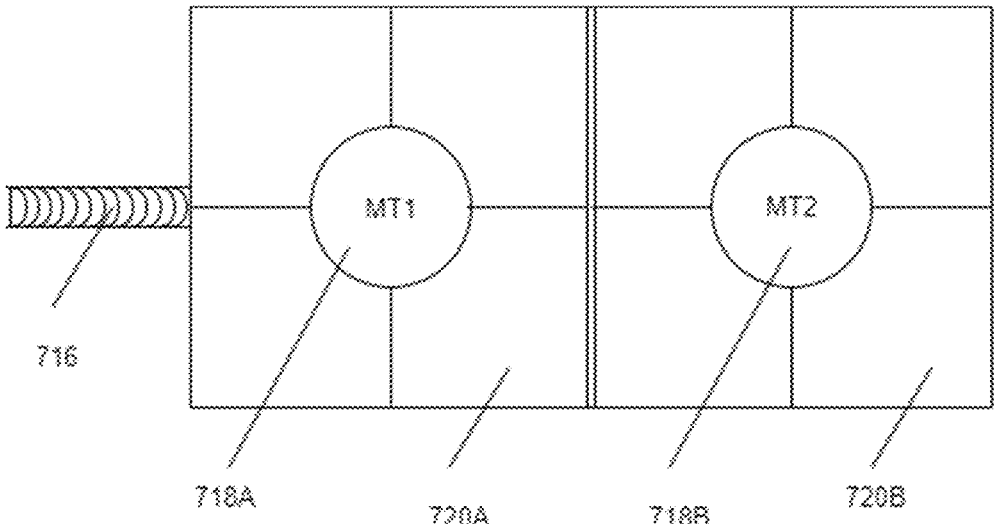

Referring to FIG. 34, there is illustrated one example of an ultrasound beam quality test apparatus. In an exemplary embodiment, the metal plate 718 can be formed from a non-metallic material 720A/720B, wherein the metal plate 718A/718B fits into orifices cut through the non-metallic material 720A/720B. In this regard, the non-metallic material 720A/720B can be plastic or other suitable non-metallic material, and the metal plate(s) 718A-718B can be fitted into the non-metallic material 720A/720B. Additionally, empty space/air gaps can be cut, in the non-metallic material 720A/720B, around the metal plates 718A/718B to minimize ultrasound beam reflection from the area between metal plates 718A/718B. Furthermore, the non-metallic frame 720A/720B material can be fabricated from an ultrasound absorbing material. An advantage of this construction technique, in the present invention, is that the non-metallic material 720A/720B can reduce the weight as well as isolate the metal plate(s) 718A/718B over the transducers 100/200 reducing the chance of reflected wave interference.

Figure 35:
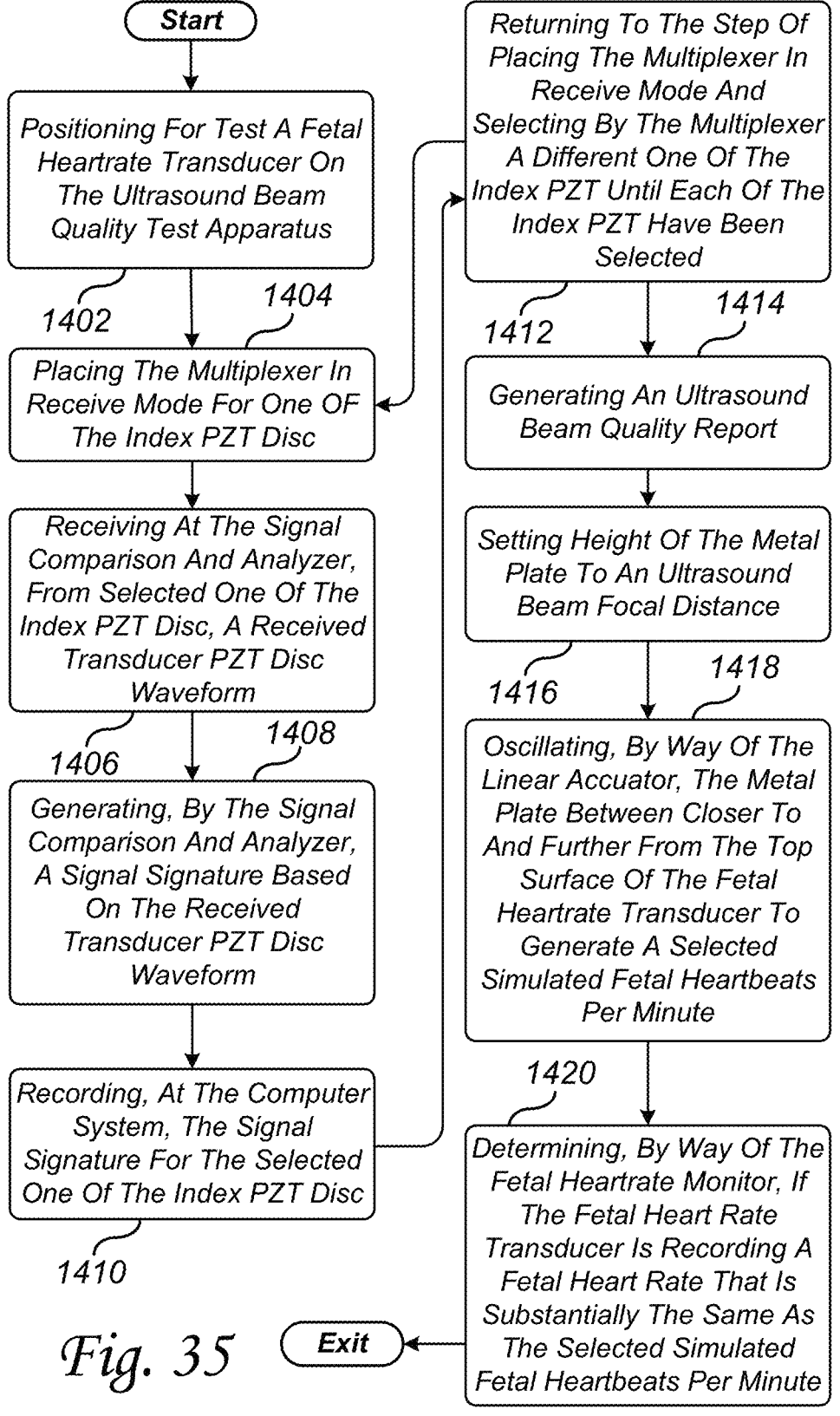
FIG. 35 illustrates one example of a method of using an ultrasound beam quality test apparatus.

Referring to FIG. 35, there is illustrated one example of a method of using an ultrasound beam quality test apparatus 648 to test fetal heart rate transducer 100/200. In an exemplary embodiment, the method begins in step 1402.

In step 1402, a fetal heart rate transducer 100/200 is positioned for test on the ultrasound beam quality test apparatus 648 test surface 720 or on a raised platform 714 which is placed on the test surface 720, as required based on the type of testing being undertaken.

A computer system 650 comprises a microprocessor 674, a memory 676, a beam control circuit 652, and a linear actuator controller 684. The microprocessor 674 is operationally related to the memory 676, the beam control circuit 652, and the linear actuator controller 684. The beam control circuit 652 comprises at least one of a multiplexer 654A-B, at least one of an analog-to-digital converter 660A-B, and a signal comparison and analyzer 662. Other circuitry can include buffers and amplifiers 656A-D, other control circuitry 658, 664, and 668, a buzzer 666, and other circuits as may be required and/or desired in a particular embodiment.

A fetal heart rate transducer 100/200 can comprise more than one transducer piezo-electric crystal (PZT) disc 112/218. The fetal heart rate transducer 100/200 can be electrically interconnected with a fetal monitor 302 which causes each of the transducer PZT discs 112/218 to generate a transducer PZT disc waveform 366.

An index plate 702 comprises more than one of a hydrophone PZT disc 604. Phantom 706/708/710 can be placed between the fetal heart rate transducer 100/200 and the index plate 702. Each of the hydrophone PZT discs 604 can adhere to the index plate 702 in positions that align with and correspond to locations of each of the transducer PZT discs 112/218 within the fetal heart rate transducer 100/200. The index plate 702 can have a flat surface, have holes that can be used for alignment, be integrally formed on the top surface of phantom 706/708/710, or be configured in other ways, as may be required and/or desired in an embodiment. The hydrophone PZT disc 604 can be adhered to the index plate 702 in a similar manner as the transducer PZT disc 112/218 is adhered to the enclosure in the present invention. In this regard, receiving the transducer PZT disc waveform by the hydrophone PZT disc 604 can be improved when the hydrophone PZT disc 604 is adhered to the index plate 702 in accordance with the methods of the present invention.

Each of the hydrophone PZT disc 604 can be electrically interconnected, by way of connectors CN1 or CN2, to the beam control circuit 652. A linear actuator 716 has a motor 690, and a metal plate 718 that is attached to the linear actuator 716. The metal plate 718 is vertically adjustable by way of the motor 690, by way of the linear actuator 716. The metal plate 718 extends across the top surface of the fetal heart rate transducer 100/200. The linear actuator controller 684 operates the linear actuator 716 by way of the motor 690.

The method continues in step 1404 by placing the multiplexer 654A-B in a receive mode of operation for one of the hydrophone PZT disc 604 and electrically disconnecting the other of the hydrophone PZT disc 604 so that the signal comparison and analyzer 662 receives only one received transducer PZT disc waveform 368 to analyze at a time. The method then moves to step 1406. For disclosure purposes, two separate channels can be used for testing and as such multiplexer 654A can be dedicated to one channel and multiplexer 654B can be dedicated to the other channel.

In step 1406, a received transducer PZT disc waveform 368 is received at the signal comparison and analyzer 662, from the selected one of the hydrophone PZT disc 604. The received transducer PZT disc waveform 368 is the transducer PZT disc waveform 366 from the transducer PZT disc that is positioned directly opposite selected one of the hydrophone PZT disc 112/218 after passing through the phantom 706/708/710.

In operation, when index plate with all 7 PZT discs is placed directly on the transducer face, each hydrophone PZT on the index plate picks up the transmitted wave exclusively from the PZT disc directly opposite inside the transducer. When Phantoms with length 706/708/710 are used, the signal pick up by the hydrophone PZT is a cumulative effect of transmission by all the transducer discs but the majority contribution is by the PZT disc directly opposite inside the transducer when the transducer is connected to the fetal monitor without opening the transducer. The method then moves to step 1408.

In step 1408, a signal signature is generated, by way of the signal comparison and analyzer 662 based on the received transducer PZT disc waveform 662 The method then moves to step 1410.

In step 1410, at the computer system 650, the signal signature is recorded for the selected one of the hydrophone PZT disc 604, wherein the selected one of the hydrophone PZT disc 604 corresponds to one of the transducer PZT disc 112/218. The method then moves to step 1412.

In step 1412, the method then returns to the step of placing and selecting by the multiplexer 654A-B and selecting a different one of the hydrophone PZT disc 604 until each signal signature has been recorded for each of the hydrophone PZT disc 604. In this regard, each one of the hydrophone PZT discs corresponds to one of the transducer PZT discs 112/218. So, by testing and recording a signal signature 368 for each of the hydrophone PZT disc 604 you are testing each of the transducer PZT disc 112/218.

The method then continues in step 1414 by generating, by way of the computer system 650, an ultrasound beam quality report, wherein the ultrasound beam quality report compares one or more of a predetermined reference signal signature with the signal signature recorded for each one of the hydrophone PZT disc 604 to determine ultrasound beam quality of the fetal heart rate transducer 100/200, wherein each one of the hydrophone PZT disc 604 corresponds to one of the transducer PZT disc 112/218. The method then continues in step 1416.

In step 1416, the height of the metal plate 718 is set to an ultrasound beam focal distance 372, by way of the linear actuator 716. In operation, in this configuration, the phantom 706/708/710 and the index plate 702 are repositioned away from the top surface of the fetal heart rate transducer 100/200 so that the top surface of the fetal heart rate transducer 100/200 and the metal plate 718 are opposed with only an air gap therebetween. The method then moves to step 1418.

In step 1418, by way of the linear actuator 716, the metal plate 718 is oscillated, between closer to and further from the top surface of the fetal heart rate transducer 100/200 to generate a selected simulated fetal heartbeats per minute. In operation, the transducer PZT disc waveform 366 is reflected 370 off of the metal plate 718 and received at the transducer PZT disc 112/218. The oscillating motion of the metal plate 718 simulates the mechanical motion of the infant (fetus) heart and the reflected wave 370 when received by the fetal heart rate transducer 100/200 is interrupted as a fetal heartbeat. The selected simulated fetal heartbeats per minute can range from 20 beats per minute to 240 beats (though the transducer 100/200 can be simulated tested to around 350 bpm for accuracy) which corresponds to the boundaries and range of a fetal heart rate and/or fetal heart rate equipment such as the fetal heart rate transducer 100/200, the fetal monitor 302, or other types and kind of fetal heart rate equipment, as may be required and/or desired in a particular embodiment. The method then moves to step 1420.

In step 1420, by way of the fetal monitor 302, it is determined if the fetal heart rate transducer 100/200 is recording a fetal heart rate that is substantially the same as the selected simulated fetal heartbeats per minute which is an indication that the fetal heart rate transducer 100/200 is operating correctly.

Referring to FIG. 36, there are illustrated exemplary embodiments that can be used interchangeably with the methods of the present invention.

In an exemplary embodiment, in step 1608, a raised platform 714A-B can be placed under the fetal heart rate transducer 100/200 to elevate the transducer by a fixed distance. In this regard, during simulated fetal heartbeat testing and as better illustrated in at least FIG. 33, a raised platform 714 can be placed under the fetal heart rate transducer 100/200 to better isolate the transducer by mitigating the effects the test surface 720 might have on the transducer 100/200.

In an exemplary embodiment, in step 1610, during testing the selected simulated fetal heartbeats per minute can be changed and the method returned to the step of oscillating until the fetal heart rate transducer 100/200 has been tested in incremental step amounts of the selected simulated fetal heartbeats per minute between a minimum simulated fetal heartbeats per minute and a maximum simulated fetal heartbeats per minute. In this regard, the testing can be accomplished over a range of simulated fetal heartbeats per minute range to ensure the correct operation of the fetal heart rate transducer 100/200 over a predetermined operating range and maximum beat-to beat variation as per fetal monitor-transducer set design specifications.

Additionally, selectively, in certain exemplary embodiments, a selected allowable beat-to-beat variation can be changed. The selected allowable beat-to-beat variation is the variation in the actual read fetal heart rate from beat-to-beat. Such variation can be in the range of 1 bpm to 40 bpm, or other suitable range, as may be required and or desired in a particular embodiment.

In an exemplary embodiment, in step 1612, each of the selected simulated fetal heartbeats per minute can be tested for a duration of at least 30 seconds to validate the fetal heart rate transducer 100/200 stability of accuracy at the selected simulated fetal heartbeats per minute over a predetermined time period. In other exemplary embodiments, other testing durations can be selected, as may be required and/or desired in a particular embodiment.

In an exemplary embodiment, in step 1614, the minimum simulated fetal heartbeat can be in the range of 40 heartbeats per minute to 60 heartbeats per minute, or other selected range, as may be required and/or desired in a particular embodiment.

In an exemplary embodiment, in step 1616, the maximum simulated fetal heartbeat is in the range of 240-350 heartbeats per minute, or other selected range, as may be required and/or desired in a particular embodiment.

In step 1602, the height of the metal plate 718 is set to an ultrasound beam focal distance 372, by way of the linear actuator 716. In operation, in this configuration, phantom 706/708/710 and the index plate 702 are repositioned away from the top surface of the fetal heart rate transducer 100/200 so that the top surface of the fetal heart rate transducer 100/200 and the metal plate 718 are opposed with only an air gap therebetween. The method then moves to step 1604.

In step 1604, by way of the linear actuator 716, the metal plate 718 is oscillated, between closer to and further from the top surface of the fetal heart rate transducer 100/200 to generate a selected simulated fetal heartbeats per minute. In operation, the transducer PZT disc waveform 366 is reflected 370 off of the metal plate 718 and received at the transducer PZT disc 112/218. The oscillating motion of the metal plate 718 simulates the mechanical motion of the infant heart and the reflected wave 370 when received by the fetal heart rate transducer 100/200 is interpreted as a fetal heartbeat. The selected simulated fetal heartbeats per minute can range from 20 beats per minute to 240-350 beats which corresponds to the boundaries and range of a fetal heart rate and/or fetal heart rate equipment such as the fetal heart rate transducer 100/200, the fetal monitor 302, or other types and kind of fetal heart rate equipment, as may be required and/or desired in a particular embodiment. The method then moves to step 1606.

In step 1606, by way of the fetal monitor 302, it is determined if the fetal heart rate transducer 100/200 is recording a fetal heart rate that is substantially the same as the selected simulated fetal heartbeats per minute which is an indication that the fetal heart rate transducer 100/200 is operating correctly.

Referring to FIG. 37, there are illustrated exemplary embodiments that can be used interchangeably with the methods of the present invention.

In an exemplary embodiment, in step 1502, the multiplexer 654A-B is placed in a receive mode of operation for one of the hydrophone PZT disc 604 and electrically disconnected the other of the hydrophone PZT disc 604 so that the signal comparison and analyzer 662 receives only one received transducer PZT disc waveform 368 to analyze at a time. For disclosure purposes, two separate channels can be used for testing and as such multiplexer 654A can be dedicated to one channel and multiplexer 654B can be dedicated to the other channel. The method then moves to step 1504.

In step 1504, a received transducer PZT disc waveform 368 is received at the signal comparison and analyzer 662, from the selected one of the hydrophone PZT disc 604. The received transducer PZT disc waveform 368 is the transducer PZT disc waveform 366 from the transducer PZT disc that is positioned directly opposite selected one of the hydrophone PZT disc 112/218 after passing through the phantom 706/708/710. The method then moves to step 1506.

In step 1506, a signal signature is generated, by way of the signal comparison and analyzer 662 based on the received transducer PZT disc waveform 662 The method then moves to step 1508.

In step 1508, at the computer system 650, the signal signature is recorded for the selected one of the hydrophone PZT disc 604, wherein the selected one of the hydrophone PZT disc 604 corresponds to one of the transducer PZT disc 112/218. The method then moves to step 1510.

In step 1510, the method then returns to the step of placing and selecting by the multiplexer 654A-B, and selecting a different one of the hydrophone PZT disc 604 until each of the signal signatures has been recorded for each of the hydrophone PZT disc 604. In this regard, each one of the hydrophone PZT discs corresponds to one of the transducer PZT discs 112/218. So, by testing and recording a signal signature 368 for each of the hydrophone PZT disc 604 you are testing each of the transducer PZT discs 112/218.

In an exemplary embodiment, in step 1512, by way of the user, phantom 706/708/710 can be changed to a phantom of a different height, and the testing repeated by returning to the step of placing. In this regard, the fetal heart rate transducer 100/200 can be tested with more than one phantom 706/708/710 height.

In step 1514, a fetal heart rate transducer 100/200 is positioned for testing on the ultrasound beam quality test apparatus 648 test surface 720 or on a raised platform 714 which is placed on the test surface 720, as required based on the type of testing being undertaken.

If the FHR tracing shows absolutely normal pattern for some period while the actual fetal heart rate is either very high above 180 bpm (tachycardia) or very low below 100 bpm or goes through late decelerations compared to contraction Toco waveform, it would cause significant fetus injury or even death before the clinical staff would realize it.

Enormously large FHR reading errors occur due to wrong clock frequency on API/Busmaster circuit boards in some affected Philips Avalon fetal monitor units if they are not corrected as per Philips Field Change Order FCO Ref. No. FCO86201672 dated 1 Oct. 2015. The Philips Avalon fetal monitors, irrespective of the model and serial numbers affected as per the aforementioned field service order FCO86201672, if the 1 MHz clock differential output signal is not stable or has jitter or noise, it being input to low voltage differential signaling (LVDS) amplifier inside the fetal heart rate transducer (model M2736A, M2736AA, Ref #867246) which finally translates it into reference clock signal for the autocorrelation FHR detection algorithm mechanism, the huge FHR error of the order of 30 to 200 percent is common.

As an example, let us say the actual base line FHR is normal at 132 bpm but due to wrong reference clock frequency, the autocorrelation algorithm detects it as 220 bpm then it could be interpreted as fetus under stress and unnecessary intervention can happen. On the other hand, let us consider a patient categorized as high risk pregnancy being monitored, the fetus heart rate is continuously around 150 bpm with normal variability in the base line but at some stage shoots up more than 200 bpm because of issues with umbilical cord/placenta but due to wrong reference clock frequency signal to autocorrelation detection block, the FHR readings hoovers around 120 to 130, there will not be low or high alarm activation on the fetal monitor and hence fetus under stress wouldn't be detected for timely intervention leading to adverse event of injury or death in some cases.

A very large frequency variation and distortion in reference clock signal from the Philips Avalon fetal monitor to the inputs of LVDS amp inside the ultrasound transducer, produces spurious FHR signal output patterns that appear on the strip chart paper as 'artifacts' and 'drop out' (gaps) in recording obviously has nothing to do with the limitations of Doppler technology or limitations of the autocorrelation algorithm detection process. If one of the differential input line from Philips Avalon fetal monitor to input to LVDS Amp inside the transducer is not electrically driven or a single connection/copper trace/conductor from API/Busmaster board inside the fetal monitor to contacts on socket on front panel, is open or any of the conductor wires from the fetal monitor socket to LVDS amp input on Main CPU board inside the transducers is intermittently/continuously open circuit, then the LVDS amp produces random noise output that gets translated into spurious FHR readings without transmission of ultrasound beam from the transducer. In other words, it means the fetal heart rate ultrasound transducer gives spuriously and totally false FHR readings without sensing any organ inside the patient's belly. This is the reason why it is extremely vital to check the 1 MHz reference clock signal for OEM specified frequency stability within +/−100 Hz (0.01% or better) at fetal monitor socket.

In an exemplary embodiment, the ultrasound beam quality test apparatus can have multiple channels with multiples PAS sockets for testing Philips Avalon monitor receptacle sockets simultaneously and simulate twin/triplet monitoring event. The Philips Avalon fetal transducer models Ultrasound M2736A, M2736AA, 867246, Toco M2734A, Toco MP M2734B, Toco+ M2735A, Toco MP 867245, ECG/IUP 867247, Toco MP 867248, all share the same type of cable-connector assembly and if the balanced twisted pair conductors carrying reference clock signal are physically stressed anywhere from the contacts pins inside the over molded connector to the transducer head where it terminates in flat connector on Main CPU board, the change in impedance cause noise pick up resulting LVDS amp output distortion that ultimately leads to enormous FHR errors and also has nothing to do with the limitations of the autocorrelation algorithm detection system.

When these cables are replaced with non-OEM aftermarket part by third party service companies, leakage current between pins of over molded connector and impedance imbalance result reference clock distortion ultimately resulting very large spurious FHR readings. Some of these repaired Philips Avalon fetal Toco and ultrasound transducers with non-OEM cable parts are on USFDA recall and whenever adverse event occurs after use of such Philips Avalon transducer with non-OEM cables/parts, the only way for the hospital to counteract vendor's (service company's) rebuttal is by way of testing the transducer with ultrasound beam quality tool with fetal simulation function and have second confirmatory testing done by the accredited laboratory.

The capabilities of the present invention can be implemented in software, firmware, hardware, or some combination thereof.

The flow diagrams depicted herein are just examples. There may be many variations to these diagrams or the steps (or operations) described therein without departing from the spirit of the invention. For instance, the steps may be performed in a differing order, or steps may be added, deleted, or modified. All of these variations are considered a part of the claimed invention.

While the preferred embodiment of the invention has been described, it will be understood that those skilled in the art, both now and in the future, may make various improvements and enhancements which fall within the scope of the claims which follow. These claims should be construed to maintain the proper protection for the invention first described.

What is claimed is:

1. A method of using an ultrasound beam quality test apparatus for testing fetal heart rate transducers, the method comprising the steps of:

positioning, for testing, a fetal heart rate transducer on the ultrasound beam quality test apparatus, a computer system comprises a microprocessor, a memory, a beam control circuit, and a linear actuator controller, the microprocessor is operationally related to the memory, the beam control circuit, and the linear actuator controller, the beam control circuit comprises at least one of a multiplexer, and a signal comparison and analyzer, a fetal heart rate transducer comprises more than one of a transducer piezo-electric crystal (PZT) disc, the fetal heart rate transducer is electrically interconnected with a fetal monitor which causes each of the transducer PZT disc to generate a transducer PZT disc waveform, an index plate comprises more than one of a hydrophone PZT disc, a phantom is placed between the fetal heart rate transducer and the index plate, each of the hydrophone PZT disc is adhered to the index plate in positions that align with and correspond to locations of each of the transducer PZT disc within the fetal heart rate transducer, each of the hydrophone PZT disc is electrically interconnected with the beam control circuit, a linear actuator comprises a metal plate, the metal plate is attached to the linear actuator and is vertically adjustable by way of the linear actuator, the metal plate extends across top surface of the fetal heart rate transducer, the linear actuator controller operates the linear actuator;

placing the multiplexer in receive mode for one of the hydrophone PZT disc, and electrically disconnecting other of the hydrophone PZT disc;

receiving at the signal comparison and analyzer, from selected one of the hydrophone PZT disc, a received transducer PZT disc waveform, the received transducer PZT disc waveform is the transducer PZT disc waveform from the transducer PZT disc that is positioned directly opposite selected one of the hydrophone PZT disc after passing through the phantom;

generating, by way of the signal comparison and analyzer, a signal signature based on the received transducer PZT disc waveform;

recording, at the computer system, the signal signature for selected one of the hydrophone PZT disc, wherein selected one of the hydrophone PZT disc corresponds to one of the transducer PZT disc;

returning to the step of placing the multiplexer in receive mode, and selecting different one of the hydrophone PZT disc until the signal signature has been recorded for each of the hydrophone PZT disc;

generating, by way of the computer system, an ultrasound beam quality report, wherein the ultrasound beam quality report compares one or more of a predetermined reference signal signature with the signal signature recorded for each one of the hydrophone PZT disc to determine ultrasound beam quality of the fetal heart rate transducer, wherein each one of the hydrophone PZT disc corresponds to one of the transducer PZT disc;

setting height of the metal plate to an ultrasound beam focal distance, by way of the linear actuator, wherein in this configuration the phantom and the index plate are repositioned away from top surface of the fetal heart rate transducer so that top surface of the fetal heart rate transducer and the metal plate are opposed with only an air gap therebetween;

oscillating, by way of the linear actuator, the metal plate between closer to and further from top surface of the fetal heart rate transducer to generate a selected simulated fetal heartbeats per minute, wherein the transducer PZT disc waveform is reflected off of the metal plate and received at the transducer PZT disc; and determining, by way of the fetal monitor, if the fetal heart rate transducer is recording a fetal heart rate that is substantially same as the selected simulated fetal heartbeats per minute.

2. The method in accordance with claim 1, further comprising the step of:

recording, prior to testing, at least one of a predetermined reference signal signature using a known good fetal heartrate transducer.

3. The method in accordance with claim 1, further comprising the step of:

changing, by way of a user, to different height one of the phantom and redoing test by returning to the step of placing the multiplexer in receive mode.

4. The method in accordance with claim 1, further comprising the step of:

changing the selected simulated fetal heartbeats per minute and returning to the step of oscillating until the fetal heart rate transducer has been tested in incremental step amounts of the selected simulated fetal heartbeats per minute between a minimum simulated fetal heartbeats per minute and a maximum simulated fetal heartbeats per minute; and changing the selected allowable beat-to-beat variation.

5. The method in accordance with claim 4, further comprising the step of:

testing each of the selected simulated fetal heartbeats per minute for at least 30 seconds, the minimum simulated fetal heartbeat is in range of 40 heartbeats per minute to 60 heartbeats per minute, and the maximum simulated fetal heartbeat is in range of 350 heartbeats per minute.

6. The method in accordance with claim 4, further comprising the step of:

placing a raised platform under the fetal heart rate transducer.

7. An ultrasound beam quality test apparatus for testing fetal heart rate transducers, the ultrasound beam test apparatus comprising:

a phantom;

a fetal monitor;

a computer system comprises a microprocessor, a memory, and a beam control circuit, the microprocessor is operationally related to the memory, and the beam control circuit, the beam control circuit comprises at least one of a multiplexer, and a signal comparison and analyzer;

a fetal heart rate transducer comprises more than one of a transducer piezo-electric crystal (PZT) disc, the fetal heart rate transducer is electrically interconnected with the fetal monitor which causes each of the transducer PZT disc to generate a transducer PZT disc waveform; and an index plate comprises more than one of a hydrophone PZT disc, the phantom is placed between the fetal heart rate transducer and the index plate, each of the hydrophone PZT disc is adhered to the index plate in positions that align with and correspond to locations of each of the transducer PZT disc within the fetal heart rate transducer, each of the hydrophone PZT disc is electrically interconnected with the beam control circuit;

the memory is encoded with instructions that when executed by the microprocessor perform the steps of:

placing the multiplexer in receive mode for one of the hydrophone PZT disc and electrically disconnecting other of the hydrophone PZT disc;

receiving at the signal comparison and analyzer, from selected one of the hydrophone PZT disc, a received transducer PZT disc waveform, the received transducer PZT disc waveform is the transducer PZT disc waveform from the transducer PZT disc that is positioned directly opposite selected one of the hydrophone PZT disc after passing through the phantom;

generating, by way of the signal comparison and analyzer, a signal signature based on the received transducer PZT disc waveform;

recording, at the computer system, the signal signature for selected one of the hydrophone PZT disc, wherein selected one of the hydrophone PZT disc corresponds to one of the transducer PZT disc;

returning to the step of placing the multiplexer in receive mode, and selecting different one of the hydrophone PZT disc until the signal signature has been recorded for each of the hydrophone PZT disc; and generating, by way of the computer system, an ultrasound beam quality report, wherein the ultrasound beam quality report compares one or more of a predetermined reference signal signature with the signal signature recorded for each one of the hydrophone PZT disc to determine ultrasound beam quality of the fetal heart rate transducer, wherein each one of the hydrophone PZT disc corresponds to one of the transducer PZT disc.

8. The ultrasound beam quality test apparatus in accordance with claim 7, further comprising:

an ultrasound coupling jelly is used to ultrasonically couple the index plate to the phantom and surface of the fetal heart rate transducer to the phantom.

9. The ultrasound beam quality test apparatus in accordance with claim 7, further comprising the step of:

changing, by way of a user, to different height one of the phantom and redoing test by returning to the step of placing.

10. The ultrasound beam quality test apparatus in accordance with claim 7, the index plate is integrally formed on surface of the phantom allowing each of the hydrophone PZT discs to be adhered to surface of the phantom.

11. The ultrasound beam quality test apparatus in accordance with claim 7, further comprises:

a second phantom;

a second fetal heart rate transducer comprises more than one of a second transducer piezo-electric crystal (PZT) disc, the second fetal heart rate transducer is electrically interconnected with the fetal monitor which causes each of the second transducer PZT disc to generate a second transducer PZT disc waveform; and a second index plate comprises more than one of a second hydrophone PZT disc, the second phantom is placed between the second fetal heart rate transducer and the second index plate, each of the second hydrophone PZT disc is adhered to the second index plate in positions that align with and correspond to locations of each of the second transducer PZT disc within the second fetal heart rate transducer, each of the second hydrophone PZT disc is electrically interconnected with the beam control circuit;

the beam control circuit comprises a second multiplexer, the microprocessor is operationally related to the second multiplexer, the memory is encoded with instructions that when executed by the microprocessor perform the steps of:

placing the second multiplexer in receive mode, in a mutually exclusive manner from the multiplexer, for one of the second hydrophone PZT disc and electrically disconnecting other of the second hydrophone PZT disc;

receiving at the signal comparison and analyzer, from selected one of the second hydrophone PZT disc, a second received transducer PZT disc waveform, the second received transducer PZT disc waveform is the second transducer PZT disc waveform from the second transducer PZT disc that is positioned directly opposite selected one of the second hydrophone PZT disc after passing through the second phantom;

generating, by way of the signal comparison and analyzer a second signal signature based on the second received transducer PZT disc waveform;

recording, at the computer system, the second signal signature for selected one of the second hydrophone PZT disc, wherein selected one of the second hydrophone PZT disc corresponds to one of the second transducer PZT disc; and returning to the step of placing the second multiplexer in receive mode, and selecting different one of the second hydrophone PZT disc until the second signal signature has been recorded for each of the second hydrophone PZT disc; and generating, by way of the computer system, a second ultrasound beam quality report, wherein the second ultrasound beam quality report compares one or more of the predetermined reference signal signature with the second signal signature recorded for each one of the second hydrophone PZT disc to determine ultrasound beam quality of the second fetal heart rate transducer, wherein each one of the second hydrophone PZT disc corresponds to one of the second transducer PZT disc;

wherein the fetal heart rate transducer and the second fetal heart rate transducer can be simultaneously tested for the ultrasound beam quality, in a mutually exclusive manner, using a single one of the ultrasound beam quality test apparatus.

12. The ultrasound beam quality test apparatus in accordance with claim 7, each of the hydrophone PZT disc having a top side and an epoxy side, each of the hydrophone PZT disc adheres to the index plate as follows:

cleaning surface and the index plate;

mixing and degassing in a vacuum, for a first degas time period, an ultra slow-cure epoxy;

depositing a drop of the ultra slow-cure epoxy in center of the epoxy side of each of the hydrophone PZT disc while the hydrophone PZT disc is resting on horizontal surface with the epoxy side up, or on the index plate while the index plate is resting on horizontal surface;

allowing the drop to self-level for a first self-leveling time period;

placing the epoxy side of each of the hydrophone PZT disc on the index plate at predetermined locations while the index plate is resting on horizontal surface; and allowing the hydrophone PZT disc and the index plate assembly to cure for a first cure time period.

13. The ultrasound beam quality test apparatus in accordance with claim 12, the first degas time period is 15 to 20 minutes, the first self-leveling time period is 15 to 20 minutes, the first cure time period is a minimum of 68 hours, the ultra slow-cure epoxy is mixed as four parts resin to one part hardener, and the size of the drop is in the range of 0.2 ml.

14. The ultrasound beam quality test apparatus in accordance with claim 7, the received transducer PZT disc waveform from selected one of the hydrophone PZT disc is converted from analog-to-digital representation of the received transducer PZT disc waveform prior to reaching the signal comparison and analyzer.

15. The ultrasound beam quality test apparatus in accordance with claim 7, further comprising:

a linear actuator comprises a metal plate, the metal plate is attached to the linear actuator and is vertically adjustable by way of the linear actuator, the metal plate extends across top surface of the fetal heart rate transducer; and a linear actuator controller is operationally related to the microprocessor and operates the linear actuator, the microprocessor is operationally related to the linear actuator controller, the memory is encoded with instructions that when executed by the microprocessor perform the steps of:

setting height of the metal plate to an ultrasound beam focal distance, by way of the linear actuator, wherein in this configuration the phantom and the index plate are repositioned away from top surface of the fetal heart rate transducer so that top surface of the fetal heart rate transducer and the metal plate are opposed with only an air gap therebetween;

oscillating, by way of the linear actuator, the metal plate between closer to and further from top surface of the fetal heart rate transducer to generate a selected simulated fetal heartbeats per minute, wherein the transducer PZT disc waveform is reflected off of the metal plate and received at the transducer PZT disc; and determining, by way of the fetal monitor, if the fetal heart rate transducer is recording a fetal heart rate that is substantially same as the selected simulated fetal heartbeats per minute.

16. The ultrasound beam quality test apparatus in accordance with claim 15, the memory is encoded with instructions that when executed by the microprocessor perform the step of:

changing the selected simulated fetal heartbeats per minute and returning to the step of oscillating until the fetal heart rate transducer has been tested in incremental step amounts of the selected simulated fetal heartbeats per minute between a minimum simulated fetal heartbeats per minute and a maximum simulated fetal heartbeats per minute.

17. The ultrasound beam quality test apparatus in accordance with claim 16, each of the selected simulated fetal heartbeats per minute is tested for at least 30 seconds, the minimum simulated fetal heartbeat is in range of 40 heartbeats per minute to 60 heartbeats per minute, and the maximum simulated fetal heartbeat is in range of 350 heartbeats per minute.

18. The ultrasound beam quality test apparatus in accordance with claim 15, further comprising:

a raised platform, the fetal heart rate transducer is placed on the raised platform during simulated fetal heartbeats per minute testing.

19. An ultrasound beam quality test apparatus for testing fetal heart rate transducers, the ultrasound beam test apparatus comprising:

a fetal monitor;

a computer system comprises a microprocessor and a memory and linear actuator controller, the microprocessor is operationally related to the memory and the linear actuator controller;

a fetal heart rate transducer comprises more than one of a transducer piezo-electric crystal (PZT) disc, the fetal heart rate transducer is electrically interconnected with the fetal monitor which causes each of the transducer PZT disc to generate a transducer PZT disc waveform;

a linear actuator comprises a metal plate, the metal plate is movably attached to the linear actuator and is vertically adjustable by way of the linear actuator, the metal plate extends across top surface of the fetal heart rate transducer, the linear actuator controller operates the linear actuator; and the memory is encoded with instructions that when executed by the microprocessor perform the steps of:

setting height of the metal plate to an ultrasound beam focal distance, by way of the linear actuator, wherein top surface of the fetal heart rate transducer and the metal plate are opposed with only an air gap therebetween;

oscillating, by way of the linear actuator, the metal plate between closer to and further from top surface of the fetal heart rate transducer to generate a selected simulated fetal heartbeats per minute, wherein the transducer PZT disc waveform is reflected off of the metal plate and received at the transducer PZT disc; and determining, by way of the fetal monitor, if the fetal heart rate transducer is recording a fetal heart rate that is substantially same as the selected simulated fetal heartbeats per minute.

20. The ultrasound beam quality test apparatus in accordance with claim 19, the memory is encoded with instructions that when executed by the microprocessor perform the step of:

changing the selected simulated fetal heartbeats per minute and returning to the step of oscillating until the fetal heart rate transducer has been tested in incremental step amounts of the selected simulated fetal heartbeats per minute between a minimum simulated fetal heartbeats per minute and a maximum simulated fetal heartbeats per minute.

21. The ultrasound beam quality test apparatus in accordance with claim 20, each of the selected simulated fetal heartbeats per minute is tested for at least 30 seconds, the minimum simulated fetal heartbeat is in range of 40 heartbeats per minute to 60 heartbeats per minute, and the maximum simulated fetal heartbeat is in range of 350 heartbeats per minute.

22. The ultrasound beam quality test apparatus in accordance with claim 19, further comprising:

a raised platform, the fetal heart rate transducer is placed on the raised platform.

23. The ultrasound beam quality test apparatus in accordance with claim 19, further comprising:

a phantom;

a beam control circuit, the computer system, comprises the beam control circuit, the beam control circuit comprises at least one of a multiplexer, and a signal comparison and analyzer; and an index plate comprises more than one of a hydrophone PZT disc, the phantom is placed between the fetal heart rate transducer and the index plate, each of the hydrophone PZT disc is adhered to the index plate in positions that align with and correspond to locations of each of the transducer PZT disc within the fetal heart rate transducer, each of the hydrophone PZT disc is electrically interconnected with the beam control circuit;

the memory is encoded with instructions that when executed by the microprocessor perform the steps of:

placing the multiplexer in receive mode for one of the hydrophone PZT disc and electrically disconnecting other of the hydrophone PZT disc;

receiving at the signal comparison and analyzer, from selected one of the hydrophone PZT disc, a received transducer PZT disc waveform, the received transducer PZT disc waveform is the transducer PZT disc waveform from the transducer PZT disc that is positioned directly opposite selected one of the hydrophone PZT disc after passing through the phantom;

recording, at the computer system, the signal signature for selected one of the hydrophone PZT disc, wherein selected one of the hydrophone PZT disc corresponds to one of the transducer PZT disc;

determining, at the computer system, the signal signature for selected one of the hydrophone PZT disc;

returning to the step of placing the multiplexer in receive mode, and selecting different one of the hydrophone PZT disc until the signal signature has been recorded for each of the hydrophone PZT disc; and generating, by way of the computer system, an ultrasound beam quality report, wherein the ultrasound beam quality report compares one or more of a predetermined reference signal signature with the signal signature recorded for each one of the hydrophone PZT disc to determine ultrasound beam quality of the fetal heart rate transducer, wherein each one of the hydrophone PZT disc corresponds to one of the transducer PZT disc.

24. The ultrasound beam quality test apparatus in accordance with claim 23, further comprising the step of:

changing, by way of a user, to different height one of the phantom and redoing test by returning to the step of placing the multiplexer in receive mode.

* * * * *